United States Patent
Takahashi et al.

(10) Patent No.: US 6,919,349 B2
(45) Date of Patent: Jul. 19, 2005

(54) SPIRO COMPOUNDS AND ADHESION MOLECULE INHIBITORS CONTAINING THE SAME AS THE ACTIVE INGREDIENT

(75) Inventors: Toshiya Takahashi, Fujisawa (JP); Takeshi Ishigaki, Kamakura (JP); Miyuki Funahashi, Fujisawa (JP); Koji Taniguchi, Kamakura (JP); Masayuki Kaneko, Kamakura (JP); Mie Kainoh, Fujisawa (JP); Hiroyuki Meguro, Kamakura (JP)

(73) Assignee: Toray Industries, Inc., Tokyo (JP)

(*) Notice: Subject to any disclaimer, the term of this patent is extended or adjusted under 35 U.S.C. 154(b) by 0 days.

(21) Appl. No.: 10/381,367
(22) PCT Filed: Sep. 25, 2001
(86) PCT No.: PCT/JP01/08290
§ 371 (c)(1),
(2), (4) Date: Mar. 25, 2003
(87) PCT Pub. No.: WO02/24697
PCT Pub. Date: Mar. 28, 2002

(65) Prior Publication Data
US 2004/0087574 A1 May 6, 2004

(30) Foreign Application Priority Data
Sep. 25, 2000 (JP) .................................. 2000-289658

(51) Int. Cl.$^7$ ................... C07D 471/10; A61K 31/438; A61P 29/00; A61P 19/02
(52) U.S. Cl. .................. 514/278; 546/20; 540/543; 544/231
(58) Field of Search ............................ 546/20; 514/278

(56) References Cited

U.S. PATENT DOCUMENTS 5,760,029 A    6/1998   Jadhav et al. ............... 514/211

FOREIGN PATENT DOCUMENTS

| JP | 8-337569 | 12/1996 |
|---|---|---|
| WO | WO 95/7294 A1 | 3/1995 |
| WO | WO 99/10312 A1 | 3/1999 |
| WO | WO 00/61545 A1 | 10/2000 |
| WO | WO 01/21584 A1 | 3/2001 |

*Primary Examiner*—Mark L. Berch
*Assistant Examiner*—Kahsay Habte
(74) *Attorney, Agent, or Firm*—Birch, Stewart, Kolasch & Birch, LLP

(57) ABSTRACT

Disclosed are novel spiro derivatives and their medical uses, especially as adhesion molecule inhibitors useful for therapies of inflammatory diseases. The spiro derivative according to the present invention has the chemical structure, for example, represented by the following Formula (31):

(31)

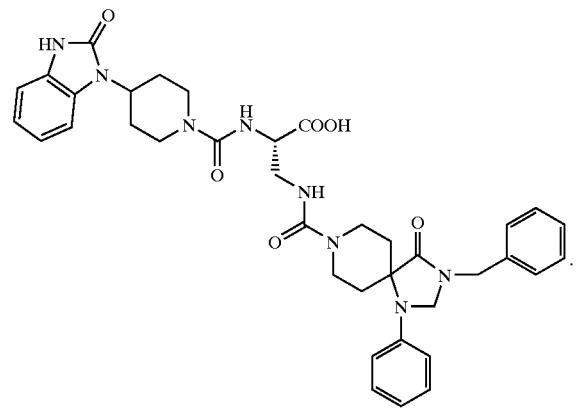

12 Claims, No Drawings

SPIRO COMPOUNDS AND ADHESION MOLECULE INHIBITORS CONTAINING THE SAME AS THE ACTIVE INGREDIENT

This application is the national phase under 35 U.S.C. § 371 of PCT International Application No. PCT/JP01/08290 which has an International filing date of Sep. 25, 2001, which designated the United States of America.

TECHNICAL FIELD

The present invention relates to a novel spiro derivative or a pharmaceutically acceptable salt thereof, useful as an adhesion molecule inhibitor, especially VLA-4 inhibitor, to an adhesion molecule inhibitor, especially VLA-4 inhibitor, containing the same, and to a therapeutic agent against inflammatory diseases containing the same.

BACKGROUND ART

Adhesion molecules participate in adhesion between cells and cells, and between cells and cell matrix. Adhesion molecules include a number of families such as integrin family and immunoglobulin super family. The adhesion molecules belonging to integrin family are those expressed on leukocytes such as lymphocytes, monocytes, basophils and eosinophils. These adhesion molecules have heterodimer structure, in which an α chain and a β chain are non-covalently bound, and are classified into some subfamilies depending on the species of the β chain. VLA-4 (very late antigen-4) also called α4β1 or CD49d/CD29, a member of the integrin family, participates in the interactions between leukocytes and vascular endothelial cells or extracellular matrix, and participates in infiltration of leukocytes into inflammatory site. VCAM-1 (vascular cell adhesion molecule-1) and fibronectin are known as the adhesion molecules which interact with VLA-4.

The binding site on fibronectin, which binds to VLA-4 is a fibronectin fragment called CS-1. It has been reported that the minimum unit required for the binding in this fragment consists of 3 amino acid residues, that is, Leucine-Aspartic acid-Valine.

Linear or cyclic peptidic VLA-4 adhesion inhibitor compounds based on the 3 amino acid residues, Leucine-Aspartic acid-Valine have been reported (WO/15973).

On the other hand, it is known that the expression level of VCAM-1 which is another adhesion molecule that also interacts with VLA-4, is increased by stimulation by a cytokine such as IL-1, TNF-α or IL-4, and that VCAM-1 interacts with VLA-4 existing on cells such as lymphocytes, NK cells, monocytes and eosinophils. VLA-4 and VCAM-1 participate in the infiltration of leukocytes into inflammatory sites through blood vessels. From this view point, the interaction between VLA-4 and VCAM-1 is very important in inflammatory reaction.

Among the adhesion molecules, VCAM-1 belongs to the immunoglobulin super family, and 7-Ig-like-domain VCAM-1 and 6-Ig-like-domain VCAM-1 are known. Mutation experiments of VCAM-1 revealed that the binding sites on VCAM-1 for binding to VLA-4 are located in domain 1 and domain 4, and that the amino acid sequence of glutamine-isoleucine-aspartic acid-serine-proline on the CD loop is important for the binding to VLA-4 (e.g., J. Cell Biol., 124, 601(1994)). J. H. WANG et al. reported a cyclic peptide Cys*GlnIleAspSerProCys* (Cys*Cys* represents disulfide bond) which has an inhibitory activity against adhesion of VLA-4, which cyclic peptide is based on the glutamine-isoleucine-aspartic acid-serine-proline (Proc. Natl. Acad. Sci. USA, 92, 5714 (1995)). Low molecular compounds having VLA-4-inhibitory activity have also been reported (e.g., U.S. Pat. No. 5,770,573, U.S. Pat. No. 5,821,231 and WO99/6436).

The fact that VLA-4 plays an important role in inflammatory reaction has been proved by experiments using anti-VLA-4 antibody in animal models such as contact hypersensitivity, delayed type hypersensitivity models (mouse and rat), experimental autoimmune encephalomyelitis models (mouse and rat), nephrotic nephritis (rat), passive cutaneous anaphylaxis model (guinea pig), immunocomplex-induced pulmonary injury model (rat), spontaneous colitis model (monkey), asthma model (sheep) and adjuvant arthritis model.

DISCLOSURE OF THE INVENTION

It has been proved that the cause of development of chronic inflammatory diseases such as allergic inflammation and chronic rheumatoid arthritis is the repetition of accumulation of leukocytes at the inflammatory site. However, as the drugs for the therapies of these diseases, drugs having activities to inhibit actions of chemical mediators, drugs having activities to inhibit production of chemical mediators, and drugs having activities to inhibit production of active oxygen are conventionally used. Drugs which inhibit activation of leukocytes, such as steroid drugs, are also used. Since these drugs do not have an activity to inhibit accumulation of leukocytes to the inflammatory site as their main actions, they cannot inhibit development of inflammation. In contrast, since adhesion molecules VLA-4 and VCAM-1 mainly participate in the process of accumulation of the leukocytes to the inflammatory site, a novel compound having an activity to inhibit the adhesion of VLA-4 and VCAM-1 is thought to inhibit the accumulation of the leukocytes to the inflammatory site. Thus, the probability that such a compound is an effective therapeutic drug against the above-mentioned diseases is high.

An object of the present invention is to discover a compound which inhibits cell infiltration via adhesion molecules, especially, adhesion molecule VLA-4, thereby making it possible to prevent and cure inflammatory diseases caused by infiltration of leukocytes such as monocytes, lymphocytes and eosinophils.

The present inventors intensively studied to discover that specific novel spiro derivatives and pharmaceutically acceptable salts thereof have activities to inhibit cell adhesion via adhesion molecules, especially adhesion molecule VLA-4, thereby completing the present invention.

That is, the present invention provides a spiro derivative represented by the Formula I:

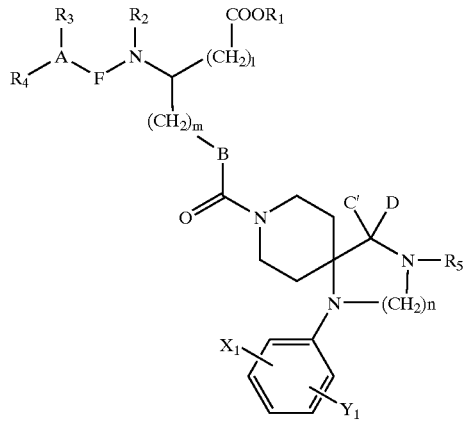

[wherein l and m independently represent integers of 0 to 2; n represents an integer of 1 to 3; A represents an oxygen atom, carbon atom or a nitrogen atom (with the proviso that when A is an oxygen atom, $R_3$ does not exist); B represents a carbon atom or a nitrogen atom; C' and D represent hydrogen, or C' and D cooperatively represent carbonyl; $X_1$ and $Y_1$ independently represent hydrogen, halogen, $C_1$–$C_8$ alkyl, $C_1$–$C_8$ alkoxy, cyano, nitro, hydroxyl, amino or tetrazole; $R_1$ and $R_2$ independently represent hydrogen or $C_1$–$C_6$ linear alkyl; $R_3$ and $R_4$ independently represent hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole; F represents —$CH_2$— or —C(O)—;

when A is a nitrogen atom, $R_3$, A and $R_4$ may cooperatively represent (i) Formula II:

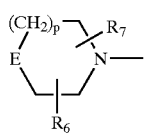

(wherein p represents an integer of 0 to 4; E represents a carbon atom or a nitrogen atom; $R_6$ and $R_7$ independently represent hydrogen, $C_1$–$C_6$ linear alkyl, $C_3$–$C_8$ branched alkyl, $C_1$–$C_6$ linear alkylacyl, $C_3$–$C_8$ branched alkylacyl, pyrrolidinecarbonyl, peperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, $C_1$–$C_8$ alkyl, $C_1$–$C_8$ alkoxy, cyano, nitro, hydroxyl, amino and tetrazole, or Formula III:

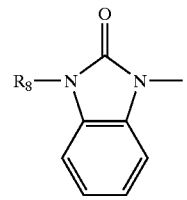

(wherein $R_8$ represents hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole), (ii) Formula IV:

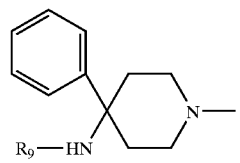

(wherein $R_9$ represents $C_1$–$C_6$ linear alkyl, $C_3$–$C_8$ branched alkyl, $C_1$–$C_6$ linear alkylacyl, $C_3$–$C_8$ branched alkylacyl, $C_5$–$C_7$ cycloalkylacyl, $C_1$–$C_6$ linear alkylsulfonyl, $C_3$–$C_8$ branched alkylsulfonyl, or benzoyl, phenylsulfonyl or benzyl, this benzoyl, phenylsulfonyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole)

(iii) Formula V:

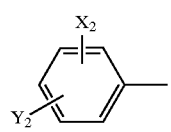

(wherein $R_{10}$ represents hydrogen, $C_1$–$C_6$ linear alkyl, $C_3$–$C_8$ branched alkyl, $C_6$–$C_{10}$ alkylcycloalkyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole);

When A is a carbon atom, $R_3$, A and $R_4$ may cooperatively form adamantyl, Formula VI:

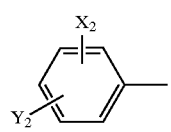

(wherein definitions of $X_2$ and $Y_2$ are the same as those of $X_1$ and $Y_1$, respectively) or Formula VII:

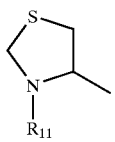

(wherein definition of $R_{11}$ is the same as that of $R_9$);
$R_5$ represents hydrogen, $C_1$–$C_6$ linear alkyl, $C_3$–$C_8$ branched alkyl, allyl, homoallyl, $C_6$–$C_{10}$ alkylcycloalkyl, or phenyl, benzyl, phenethyl, styryl or naphthylmethyl, this phenyl, benzyl, phenethyl, styryl or naphthylmethyl being substituted with 0 to 2 substituents selected from the group consisting of halogen, $C_1$–$C_8$ alkyl, $C_1$–$C_8$ alkoxy, cyano, nitro, hydroxyl, amino and tetrazole]
or a pharmaceutically acceptable salt thereof.

The present invention also provides an adhesion molecule inhibitor comprising the spiro derivative or a pharmaceutically acceptable salt thereof according to the present invention. The present invention further provides a medical use of the spiro derivative or a pharmaceutically acceptable salt thereof according to the present invention, and especially, a therapeutic agent for inflammatory diseases. The present invention still further provides a method for inhibiting an adhesion molecule, comprising administering an effective amount of the spiro derivative or a pharmaceutically acceptable salt thereof according to the present invention. The present invention still further provides a use of the spiro derivative or a pharmaceutically acceptable salt thereof according to the present invention for the production of a pharmaceutical. The present invention still further provides a use of the spiro derivative or a pharmaceutically acceptable salt thereof according to the present invention for the production of an adhesion molecule inhibitor.

By the present invention, novel substances having activities to inhibit cell adhesion via adhesion molecules, especially adhesion molecule VLA-4, were provided. By the present invention, prevention and therapy of the inflammatory diseases caused by infiltration of leukocytes such as monocytes, lymphocytes and eosinophils can be attained.

Best Mode for Carrying Out the Invention

As mentioned above, the spiro derivatives according to the present invention are represented by the above-described Formula I. In Formula I, 1 represents an integer of 0 to 2; m represents an integer of 0 to 2; n represents an integer of 1 to 3; A represents an oxygen atom, carbon atom or a nitrogen atom (with the proviso that when A is an oxygen atom, $R_3$ does not exist); B represents a carbon atom or a nitrogen atom; C' and D represent hydrogen, or C' and D cooperatively represent carbonyl; $X_1$ and $Y_1$ independently represent hydrogen, halogen, $C_1$–$C_8$ alkyl such as methyl, ethyl, n-propyl or isopropyl, $C_1$–$C_8$ alkoxy such as methoxy, ethoxy, n-propyloxy or isopropyloxy, cyano, nitro, hydroxyl, amino or tetrazole; $R_1$ and $R_2$ represent hydrogen or $C_1$–$C_6$ linear alkyl, that is, methyl, ethyl, n-propyl, n-butyl, n-pentyl or n-hexyl; $R_3$ and $R_4$ independently represent hydrogen, $C_1$–$C_6$ linear alkyl, that is, methyl, ethyl, n-propyl, n-butyl, n-pentyl or n-hexyl, $C_3$–$C_8$ branched alkyl such as 1-methylethyl, 1-methylpropyl, 2-methylpropyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 3,5-dimethylhexyl, 3,6-dimethylhexyl or 4,5-dimethylhexyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole, such as phenyl, 2-cyanophenyl, 2-hydroxyphenyl, 2-chlorophenyl, 2-nitrophenyl, 2-aminophenyl, 2-bromophenyl, 2-fluorophenyl, 2-tetrazoylphenyl, 2,6-dihydroxyphenyl, 2,6-diemthoxyphenyl, 2,6-dichlorophenyl, 2,6-dinitrophenyl, 2,6-dimethylphenyl, benzyl, 2-cyanobenzyl, 2-hydroxybenzyl, 2-chlorobenzyl, 2-nitrobenzyl, 2-aminobenzyl, 2-bromobenzyl, 2-fluorobenzyl, 2-tetrazoylbenzyl, 2,6-dihydroxybenzyl, 2,6-dimethoxybenzyl, 2,6-dichlorobenzyl, 2,6-dinitrobenzyl or 2,6-dimethylbenzyl; F represents —$CH_2$— or —C(O)—;
when A is a nitrogen atom, $R_3$, A and $R_4$ may cooperatively represent
(i) Formula II:

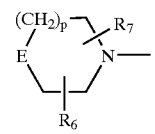

(wherein p represents an integer of 0 to 4, E represents a carbon atom or a nitrogen atom; $R_6$ and $R_7$ independently represent hydrogen, $C_1$–$C_6$ linear alkyl, that is, methyl, ethyl, n-propyl, n-butyl, n-pentyl or n-hexyl, $C_3$–$C_8$ branched alkyl such as 1-methylethyl, 1-methylpropyl, 2-methylpropyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 3,5-dimethylhexyl, 3,6-dimethylhexyl or 4,5-dimethylhexyl, $C_1$–$C_6$ linear alkylacyl such as acetyl, ethyloxy or n-propyloxy, $C_3$–$C_8$ branched alkylacyl such as isopropyloxy, isobutyloxy, isopentyloxy or isohexyloxy, pyrrolidinecarbonyl, peperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, $C_1$–$C_8$ alkyl, $C_1$–$C_8$ alkoxy, cyano, nitro, hydroxyl, amino and tetrazole, such as phenyl, 2-cyanophenyl, 2-hydroxyphenyl, 2-chlorophenyl, 2-nitrophenyl, 2-aminophenyl, 2-bromophenyl, 2-fluorophenyl, 2-tetrazoylphenyl, 2,6-dihydroxyphenyl, 2,6-dimethoxyphenyl, 2,6-dichlorophenyl, 2,6-dinitrophenyl, 2,6-dimethylphenyl, benzoyl, 2-cyanobenzoyl, 2-hydroxybenzoyl, 2-chlorobenzoyl, 2-nitrobenzoyl, 2-aminobenzoyl, 2-bromobenzoyl, 2-fluorobenzoyl, 2-tetrazoylbenzoyl, 2,6-dihydroxybenzoyl, 2,6-dimethoxybenzoyl, 2,6-dichlorobenzoyl, 2,6-dinitrobenzoyl, 2,6-dimethylbenzoyl, benzyl, 2-cyanobenzyl, 2-hydroxybenzyl, 2-chlorobenzyl, 2-nitrobenzyl, 2-amionobenzyl, 2-bromobenzyl, 2-fluorobenzyl, 2-tetrazoylbenzyl, 2,6-dihydroxybenzyl, 2,6-dimethoxybenzyl, 2,6-dichlorobenzyl, 2,6-dinitrobenzyl, 2,6-dimethylbenzyl, phenylsulfonyl, 2-cyanophenylsulfonyl, 2-hydroxyphenylsulfonyl, 2-chlorophenylsulfonyl, 2-nitrophenylsulfonyl, 2-aminophenylsulfonyl, 2-bromophenylsulfonyl, 2-fluorophenylsulfonyl, 2-tetrazoylphenylsulfonyl, 2,6-dihydroxyphenylsulfonyl, 2,6-dimethoxyphenylsulfonyl, 2,6-dichlorophenylsulfonyl, 2,6-dinitrophenylsulfonyl, 2,6-dimethylphenylsulfonyl, N-phenylcarboxamide, N-(2-cyanophenyl)carboxamide, N-(2-cyanophenyl) carboxamide, N-(2-hydroxyphenyl)carboxamide, N-(2-chlorophenyl)carboxamide, N-(2-nitrophenyl) carboxamide, N-(2-aminophenyl)carboxamide, N-(2-bromophenyl)carboxamide, N-(2-fluorophenyl) carboxamide, N-(2-tetrazoylphenyl)carboxamide, N-(2,6-dihydroxyphenyl)carboxamide, N-(2,6-dimethoxyphenyl)carboxamide, N-(2,6-dichlorophenyl) carboxamide, N-(2,6-dinitrophenyl)carboxamide or N-(2,6-dimethylphenyl)carboxamide, or Formula III:

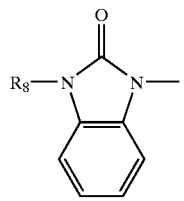

III (wherein $R_8$ represents hydrogen, $C_1-C_6$ linear alkyl, that is, methyl, ethyl, n-propyl, n-butyl, n-pentyl or n-hexyl, $C_3-C_8$ branched alkyl such as 1-methylethyl, 1-methylpropyl, 2-methylpropyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 3,5-dimethylhexyl, 3,6-dimethylhexyl or 4,5-dimethylhexyl, or phenyl or benzyl, this phenyl or benzyl being substituted with 0 to 2 substituents selected from the group consisting of halogen, $C_1-C_8$ alkyl, $C_1-C_8$ alkoxy, cyano, nitro, hydroxyl, amino and tetrazole, such as phenyl, 2-cyanophenyl, 2-hydroxyphenyl, 2-chlorophenyl, 2-nitrophenyl, 2-aminophenyl, 2-bromophenyl, 2-fluorophenyl, 2-tetrazoylphenyl, 2,6-dihydroxyphenyl, 2,6-dimethoxyphenyl, 2,6-dichlorophenyl, 2,6-dinitrophenyl, 2,6-dimethylphenyl, benzyl, 2-cyanobenzyl, 2-hydroxybenzyl, 2-chlorobenzyl, 2-nitrobenzyl, 2-aminobenzyl, 2-bromobenzyl, 2-fluorobenzyl, 2-tetrazoylbenzyl, 2,6-dihydroxybenzyl, 2,6-dimethoxybenzyl, 2,6-dichlorobenzyl, 2,6-dinitrobenzyl or 2,6-dimethylbenzyl), (ii) Formula IV:

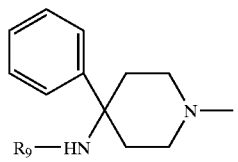

IV (wherein $R_9$ represents hydrogen, $C_1-C_6$ linear alkyl, that is, methyl, ethyl, n-propyl, n-butyl, n-pentyl or n-hexyl, $C_3-C_8$ branched alkyl such as 1-methylethyl, 1-methylpropyl, 2-methylpropyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 3,5-dimethylhexyl, 3,6-dimethylhexyl or 4,5-dimethylhexyl, $C_1-C_6$ linear alkylacyl, that is, acetyl, propionyl, butyryl, valeryl, pentanoyl or hexanoyl, $C_3-C_8$ branched alkylacyl such as isopropionyl, isobutyryl, pivaloyl, isopentanoyl, isohexanoyl or isoheptanoyl, $C_5-C_7$ cycloalkylacyl such as cyclopentylcarbonyl or cyclohexylcarbonyl, $C_1-C_6$ linear alkylsulfonyl such as mesyl, ethanesulfonyl, n-propansulfonyl, n-butanesulfonyl, n-pentanesulfonyl or n-hexanesulfonyl, $C_3-C_8$ branched alkylsulfonyl such as isopropanesulfonyl, isobutanesulfonyl, t-butanesulfonyl, isopentanesulfonyl, isohexanesulfonyl or isoheptanesulfonyl; or benzoyl, phenylsulfonyl or benzyl, this benzoyl, phenylsulfonyl or benzyl being substituted with 0 to 2 substituents selected from the group consisting of halogen, $C_1-C_8$ alkyl, $C_1-C_8$ alkoxy, cyano, nitro, hydroxyl, amino and tetrazole, such as benzoyl, 2-cyanobenzoyl, 2-hydroxybenzoyl, 2-chlorobenzoyl, 2-nitrobenzoyl, 2-aminobenzoyl, 2-bromobenzoyl, 2-fluorobenzoyl, 2-tetrazoylbenzoyl, 2,6-dihydroxybenzoyl, 2,6-dimethoxybenzoyl, 2,6-dichlorobenzoyl, 2,6-dinitrobenzoyl, 2,6-dimethylbenzoyl, phenylsulfonyl, 2-cyanophenylsulfonyl, 2-hydroxyphenylsulfonyl, 2-chlorophenylsulfonyl, 2-nitrophenylsulfonyl, 2-aminophenylsulfonyl, 2-bromophenylsulfonyl, 2-fluorophenylsulfonyl, 2-tetrazoylphenylsulfonyl, 2,6-dihydroxyphenylsulfonyl, 2,6-dimethoxyphenylsulfonyl, 2,6-dichlorophenylsulfonyl, 2,6-dinitrophenylsulfonyl, 2,6-dimethylphenylsulfonyl, benzyl, 2-cyanobenzyl, 2-hydroxybenzyl, 2-chlorobenzyl, 2-nitrobenzyl, 2-aminobenzyl, 2-bromobenzyl, 2-fluorobenzyl, 2-tetrazoylbenzyl, 2,6-dihydroxybenzyl, 2,6-dimethoxybenzyl, 2,6-dichlorobenzyl, 2,6-dinitrobenzyl or 2,6-dimethylbenzyl)

(iii) Formula V:

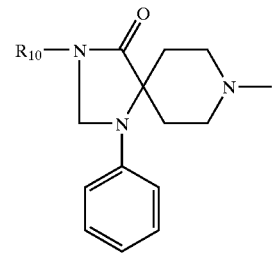

V (wherein $R_{10}$ represents hydrogen, $C_1-C_6$ linear alkyl, that is, methyl, ethyl, n-propyl, n-butyl, n-pentyl or n-hexyl, $C_3-C_8$ branched alkyl such as 1-methylethyl, 1-methylpropyl, 2-methylpropyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 3,5-dimethylhexyl, 3,6-dimethylhexyl or 4,5-dimethylhexyl, $C_6-C_{10}$ alkylcycloalkyl such as cyclopentylmethyl, cyclohexylmethyl or cycloheptylmethyl, or phenyl or benzyl, this phenyl or benzyl being substituted with 0 to 2 substituents selected from the group consisting of halogen, $C_1-C_8$ alkyl, $C_1-C_8$ alkoxy, cyano, nitro, hydroxyl, amino and tetrazole, such as phenyl, 2-cyanophenyl, 2-hydroxyphenyl, 2-chlorophenyl, 2-nitrophenyl, 2-aminophenyl, 2-bromophenyl, 2-fluorophenyl, 2-tetrazoylphenyl, 2,6-dihydroxyphenyl, 2,6-dimethoxyphenyl, 2,6-dichlorophenyl, 2,6-dinitrophenyl, 2,6-dimethylphenyl, benzyl, 2-cyanobenzyl, 2-hydroxybenzyl, 2-chlorobenzyl, 2-nitrobenzyl, 2-aminobenzyl, 2-bromobenzyl, 2-fluorobenzyl, 2-tetrazoylbenzyl, 2,6-dihydroxybenzyl, 2,6-dimethoxybenzyl, 2,6-dichlorobenzyl, 2,6-dinitrobenzyl or 2,6-dimethylbenzyl);

When A is a carbon atom, $R_3$, A and $R_4$ may cooperatively form adamantyl, Formula VI:

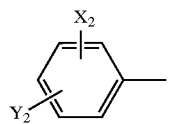

(wherein definitions of $X_2$ and $Y_2$ are the same as those of $X_1$ and $Y_1$, respectively) or Formula VII:

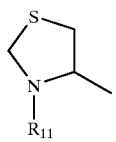

(wherein definition of $R_{11}$ is the same as that of $R_9$);
$R_5$ represents hydrogen, $C_1$–$C_6$ linear alkyl, that is, methyl, ethyl, n-propyl, n-butyl, n-pentyl or n-hexyl, $C_3$–$C_8$ branched alkyl such as 1-methylethyl, 1-methylpropyl, 2-methylpropyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 3,5-dimethylhexyl, 3,6-dimethylhexyl or 4,5-dimethylhexyl, allyl, homoallyl, $C_6$–$C_{10}$ alkylcycloalkyl such as cyclopentylmethyl, cyclohexylmethyl or cycloheptylmethyl, or phenyl, benzyl, phenethyl, styryl or naphthyl, this phenyl, benzyl, phenethyl, styryl or naphthyl being substituted with 0 to 2 substituents selected from the group consisting of halogen, $C_1$–$C_8$ alkyl, $C_1$–$C_8$ alkoxy, cyano, nitro, hydroxyl, amino and tetrazole, such as phenyl, 2-cyanophenyl, 2-hydroxyphenyl, 2-chlorophenyl, 2-nitrophenyl, 2-aminophenyl, 2-bromophenyl, 2-fluorophenyl, 2-tetrazoylphenyl, 2,6-dihydroxyphenyl, 2,6-dimethoxyphenyl, 2,6-dichlorophenyl, 2,6-dinitrophenyl, 2,6-dimethylphenyl, benzyl, 2-cyanobenzyl, 2-hydroxybenzyl, 2-chlorobenzyl, 2-nitrobenzyl, 2-aminobenzyl, 2-bromobenzyl, 2-fluorobenzyl, 2-tetrazoylbenzyl, 2,6-dihydroxybenzyl, 2,6-dimethoxybenzyl, 2,6-dichlorobenzyl, 2,6-dinitrobenzyl, 2,6-dimethylbenzyl, phenethyl, 2-cyanophenethyl, 2-hydroxyphenethyl, 2-chlorophenethyl, 2-nitrophenethyl, 2-aminophenethyl, 2-bromophenethyl, 2-fluorophenethyl, 2-tetrazoylphenethyl, 2,6-dihydroxyphenethyl, 2,6-dimethoxyphenethyl, 2,6-dichlorophenethyl, 2,6-dinitrophenethyl, 2,6-dimethylphenethyl, styryl, 2-cyanostyryl, 2-hydroxystyryl, 2-chlorostyryl, 2-nitrostyryl, 2-aminostyryl, 2-bromostyryl, 2-fluorostyryl, 2-tetrazoylstyryl, 2,6-dihydroxystyryl, 2,6-dimethoxystyryl, 2,6-dichlorostyryl, 2,6-dinitrostyryl, 2,6-dimethylstyryl, naphthyl, 2-cyanonaphthyl, 2-hydroxynaphthyl, 2-chloronaphthyl, 2-nitronaphthyl, 2-aminonaphthyl, 2-bromonaphthyl, 2-fluoronaphthyl, 2-tetrazoylnaphthyl, 2,8-dihydroxynaphthyl, 2,8-dimethoxynaphthyl, 2,8-dichloronaphthyl, 2,8-dinitronaphthyl or 2,8-dimethylnaphthyl.

Among the compounds represented by said Formula I, those wherein F represents —C(O)—; A and B independently represent carbon atom or nitrogen atom; C' and D represent hydrogen or C' and D cooperatively represent carbonyl; X and Y independently represent hydrogen, halogen, methyl, methoxy, cyano, nitro, hydroxyl, amino or tetrazole; $R_1$ and $R_2$ independently represent hydrogen or $C_1$–$C_6$ linear alkyl; $R_3$ and $R_4$ independently represent hydrogen, $C_1$–$C_6$ linear alkyl or $C_3$–$C_8$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole;

when A is a nitrogen atom, $R_3$, A and $R_4$ may cooperatively represent (i) said Formula II (wherein p represents an integer of 0 to 4; E represents a carbon atom or a nitrogen atom; $R_6$ and $R_7$ independently represent hydrogen, $C_1$–$C_6$ linear alkyl, $C_3$–$C_8$ branched alkyl, $C_1$–$C_6$ linear alkylacyl, $C_3$–$C_8$ branched alkylacyl, pyrrolidinecarbonyl, piperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, methyl, methoxy, cyano, nitro, hydroxyl, amino and tetrazole, or said Formula III (wherein $R_8$ represents hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole), (ii) said Formula IV (wherein $R_9$ represents $C_1$–$C_6$ linear alkyl, $C_3$–$C_8$ branched alkyl, $C_1$–$C_6$ linear alkylacyl, $C_3$–$C_8$ branched alkylacyl, $C_5$–$C_7$ cycloalkylacyl, $C_1$–$C_6$ linear alkylsulfonyl, $C_3$–$C_8$ branched alkylsulfonyl, or benzoyl, phenylsulfonyl or benzyl, this benzoyl, phenylsulfonyl or benzyl being substituted with 0 to 2 substituents selected from the group consisting of halogen, methyl, methoxy, cyano, nitro, hydroxyl, amino and tetrazole), (iii) said Formula V:

(wherein $R_{10}$ represents hydrogen, $C_1$–$C_6$ linear alkyl, $C_3$–$C_8$ branched alkyl, $C_6$–$C_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole);

when A is a carbon atom, $R_3$, A and $R_4$ may cooperatively represent adamantyl or said Formula VI (wherein $X_2$ and $Y_2$ represent the same definitions as described above); $R_5$ represents hydrogen, $C_1$–$C_6$ linear alkyl, $C_3$–$C_8$ branched alkyl, allyl, homoallyl, $C_6$–$C_{10}$ alkylcycloalkyl, or phenyl, benzyl, phenethyl, styryl or naphthylmethyl, this phenyl, benzyl, phenethyl, styryl or naphthylmethyl being substituted with 0 to 2 substituents selected from the group consisting of halogen, methyl, methoxy, cyano, nitro, hydroxyl, amino and tetrazole, are also preferred.

Specific examples of the compounds according to the present invention include 3-((2,4,8-triaza-1-oxo-4-phenylspiro[4.5]dec-8-yl) carbonylamino)-2-((2,6-dimethoxyphenyl) carbonylamino)propanoic acid, 3-((2,4,8-triaza-1-oxo-4-phenylspiro[4.5]dec-8-yl) carbonylamino)-2-((2,6-dimethylphenyl)carbonylamino) propanoic acid, 3-((2,4,8-triaza-1-oxo-4-phenylspiro[4.5]dec-8-yl) carbonylamino)-2-((2,6-dichlorophenyl)carbonylamino) propanoic acid, 3-((2,4,8-triaza-1-oxo-4-phenylspiro[4.5]dec-8-yl) carbonylamino)-2-((2,6-difulorophenyl)carbonylamino) propanoic acid, 3-((2,4,8-triaza-1-oxo-4-phenylspiro[4.5]dec-8-yl) carbonylamino)-2-((2-bromo-6-methylphenyl) carbonylamino)propanoic acid, 3-((2,4,8-triaza-1-oxo-4-phenylspiro[4.5]dec-8-yl)carbonylamino)-2-((2-methyl-5-nitrophenyl)carbonylamino)propanoic acid, 2-((2,6-dichlorophenyl)carbonylamino)-3-((2,4,8-triaza-2-methyl-1-oxo-4-phenylspiro[4.5]dec-8-yl)carbonylamino)propanoic acid, 2-((2,6-dimethylphenyl)carbonylamino)-3-((2,4,8-triaza-2-methyl-1-oxo-4-phenylspiro[4.5]dec-8-yl)carbonylamino)propanoic acid, 2-((2,6-dimethoxyphenyl)carbonylamino)-3-((2,4,8-triaza-2-methyl-1-oxo-4-phenylspiro[4.5]dec-8-yl)carbonylamino)propanoic acid, 2-((2,6-difluorophenyl)carbonylamino)-3-((2,4,8-triaza-2-methyl-1-oxo-4-phenylspiro[4.5]dec-8-yl)carbonylamino)propanoic acid, 2-((2-bromo-6-methylphenyl)carbonylamino)-3-((2,4,8-triaza-2-methyl-1-oxo-4-phenylspiro[4.5]dec-8-yl)carbonylamino)propanoic acid, 2-((2-methyl-5-nitrophenyl)carbonylamino)-3-((2,4,8-triaza-2-methyl-1-oxo-4-phenylspiro[4.5]dec-8-yl)carbonylamino)propanoic acid, 2-((2,6-dichlorophenyl)carbonylamino)-3-((2,4,8-triaza-2-ethyl-1-oxo-4-phenylspiro[4.5]dec-8-yl)carbonylamino)propanoic acid, 2-((2,6-dimethylphenyl)carbonylamino)-3-((2,4,8-triaza-2-ethyl-1-oxo-4-phenylspiro[4.5]dec-8-yl)carbonylamino)propanoic acid, 2-((2,6-dimethoxyphenyl)carbonylamino)-3-((2,4,8-triaza-2-ethyl-1-oxo-4-phenylspiro[4.5]dec-8-yl)carbonylamino)propanoic acid, 2-((2,6-difluorophenyl)carbonylamino)-3-((2,4,8-triaza-2-ethyl-1-oxo-4-phenylspiro[4.5]dec-8-yl)carbonylamino)propanoic acid, 2-((2-bromo-6-methylphenyl)carbonylamino)-3-((2,4,8-triaza-2-ethyl-1-oxo-4-phenylspiro[4.5]dec-8-yl)carbonylamino)propanoic acid, 2-((2-methyl-5-nitrophenyl)carbonylamino)-3-((2,4,8-triaza-2-ethyl-1-oxo-4-phenylspiro[4.5]dec-8-yl)carbonylamino)propanoic acid, 2-((2,6-dichlorophenyl)carbonylamino)-3-((2,4,8-triaza-1-oxo-4-phenyl-2-propylspiro[4.5]dec-8-yl)carbonylamino)propanoic acid, 2-((2,6-dimethylphenyl)carbonylamino)-3-((2,4,8-triaza-1-oxo-4-phenyl-2-propylspiro[4.5]dec-8-yl)carbonylamino)propanoic acid, 2-((2,6-dimethoxyphenyl)carbonylamino)-3-((2,4,8-triaza-1-oxo-4-phenyl-2-propylspiro[4.5]dec-8-yl)carbonylamino)propanoic acid, 2-((2,6-difluorophenyl)carbonylamino)-3-((2,4,8-triaza-1-oxo-4-phenyl-2-propylspiro[4.5]dec-8-yl)carbonylamino)propanoic acid, 2-((2-bromo-6-methylphenyl)carbonylamino)-3-((2,4,8-triaza-1-oxo-4-phenyl-2-propylspiro[4.5]dec-8-yl)carbonylamino)propanoic acid, 2-((2-methyl-5-nitrophenyl)carbonylamino)-3-((2,4,8-triaza-1-oxo-4-phenyl-2-propylspiro[4.5]dec-8-yl)carbonylamino)propanoic acid, 2-((2,6-dimethoxyphenyl)carbonylamino)-3-((2,4,8-triaza-2-(methylethyl)-1-oxo-4-phenylspiro[4.5]dec-8-yl)carbonylamino)propanoic acid, 2-((2,6-dimethylphenyl)carbonylamino)-3-((2,4,8-triaza-2-(methylethyl)-1-oxo-4-phenylspiro[4.5]dec-8-yl)carbonylamino)propanoic acid, 2-((2,6-dichlorophenyl)carbonylamino)-3-((2,4,8-triaza-2-(methylethyl)-1-oxo-4-phenylspiro[4.5]dec-8-yl)carbonylamino)propanoic acid, 2-((2,6-difluorophenyl)carbonylamino)-3-((2,4,8-triaza-2-(methylethyl)-1-oxo-4-phenylspiro[4.5]dec-8-yl)carbonylamino)propanoic acid, 2-((2-bromo-6-methylphenyl)carbonylamino)-3-((2,4,8-triaza-2-(methylethyl)-1-oxo-4-phenylspiro[4.5]dec-8-yl)carbonylamino)propanoic acid, 2-((2-methyl-5-nitrophenyl)carbonylamino)-3-((2,4,8-triaza-2-(methylethyl)-1-oxo-4-phenylspiro[4.5]dec-8-yl)carbonylamino)propanoic acid, 2-((2,6-dimethoxyphenyl)carbonylamino)-3-((2,4,8-triaza-2-(2-methylpropyl)-1-oxo-4-phenylspiro[4.5]dec-8-yl)carbonylamino)propanoic acid, 2-((2,6-dimethylphenyl)carbonylamino)-3-((2,4,8-triaza-2-(2-methylpropyl)-1-oxo-4-phenylspiro[4.5]dec-8-yl)carbonylamino)propanoic acid, 2-((2,6-dichlorophenyl)carbonylamino)-3-((2,4,8-triaza-2-(2-methylpropyl)-1-oxo-4-phenylspiro[4.5]dec-8-yl)carbonylamino)propanoic acid, 2-((2-methyl-5-nitrophenyl)carbonylamino)-3-((2,4,8-triaza-2-(2-methylpropyl)-1-oxo-4-phenylspiro[4.5]dec-8-yl)carbonylamino)propanoic acid, 2-((2-bromo-6-methylphenyl)carbonylamino)-3-((2,4,8-triaza-2-(2-methylpropyl)-1-oxo-4-phenylspiro[4.5]dec-8-yl)carbonylamino)propanoic acid, 2-((2,6-difluorophenyl)carbonylamino)-3-((2,4,8-triaza-2-(2-methylpropyl)-1-oxo-4-phenylspiro[4.5]dec-8-yl)carbonylamino)propanoic acid, 2-((2,6-dimethoxyphenyl)carbonylamino)-3-((2,4,8-triaza-1-oxo-4-phenyl-2-benzylspiro[4.5]dec-8-yl)carbonylamino)propanoic acid, 2-((2,6-dimethylphenyl)carbonylamino)-3-((2,4,8-triaza-1-oxo-4-phenyl-2-benzylspiro[4.5]dec-8-yl)carbonylamino)propanoic acid, 2-((2,6-dichlorophenyl)carbonylamino)-3-((2,4,8-triaza-1-oxo-4-phenyl-2-benzylspiro[4.5]dec-8-yl)carbonylamino)propanoic acid, 2-((2,6-difluorophenyl)carbonylamino)-3-((2,4,8-triaza-1-oxo-4-phenyl-2-benzylspiro[4.5]dec-8-yl)carbonylamino)propanoic acid, 2-((2-bromo-6-methylphenyl)carbonylamino)-3-((2,4,8-triaza-1-oxo-4-phenyl-2-benzylspiro[4.5]dec-8-yl)carbonylamino)propanoic acid, 2-((2-methyl-5-nitrophenyl)carbonylamino)-3-((2,4,8-triaza-1-oxo-4-phenyl-2-benzylspiro[4.5]dec-8-yl)carbonylamino)propanoic acid, 2-((2,6-dimethoxyphenyl)carbonylamino)-3-((2,4,8-triaza-2-((2,6-dimethylphenyl)methyl)-1-oxo-4-phenylspiro[4.5]dec-8-yl)carbonylamino)propanoic acid, 2-((2,6-dimethylphenyl)carbonylamino)-3-((2,4,8-triaza-2-((2,6-dimethylphenyl)methyl)-1-oxo-4-phenylspiro[4.5]dec-8-yl)carbonylamino)propanoic acid, 2-((2,6-dichlorophenyl)carbonylamino)-3-((2,4,8-triaza-2-((2,6-dimethylphenyl)methyl)-1-oxo-4-phenylspiro[4.5]dec-8-yl)carbonylamino)propanoic acid, 2,3-di((2,4,8-triaza-1-oxo-4-phenylspiro[4.5]dec-8-yl)carbonylamino)propanoic acid, 2,3-di((2,4,8-triaza-2-methyl-1-oxo-4-phenylspiro[4.5]dec-8-yl)carbonylamino)propanoic acid, 2,3-di((2,4,8-triaza-1-oxo-4-phenyl-2-benzylspiro[4.5]dec-8-yl)carbonylamino)propanoic acid, 2,3-di((2,4,8-triaza-1-oxo-4-phenyl-2-propylspiro[4.5]dec-8-yl)carbonylamino)propanoic acid, 2,3-di((2,4,8-triaza-2-(2-methylpropyl)-1-oxo-4-phenylspiro[4.5]dec-8-yl)carbonylamino)propanoic acid, 2,3-di((2,4,8-triaza-2-(2-methylethyl)-1-oxo-4-phenylspiro[4.5]dec-8-yl)carbonylamino)propanoic acid, 3-((2,4,8-triaza-2-methyl-1-oxo-4-phenylspiro[4.5]dec-8-yl)carbonylamino)-2-((2,4,8-triaza-1-oxo-4-phenylspiro[4.5]dec-8-yl)carbonylamino)propanoic acid, 3-((2,4,8-triaza-2-(2-methylpropyl)-1-oxo-4-phenylspiro[4.5]dec-8-yl)carbonylamino)-2-((2,4,8-triaza-1-oxo-4-phenylspiro[4.5]dec-8-yl)carbonylamino)propanoic acid, 3-((2,4,8-triaza-2-(2-methylethyl)-1-oxo-4-phenylspiro[4.5]dec-8-yl)carbonylamino)-2-((2,4,8-triaza-1-oxo-4-phenylspiro[4.5]dec-8-yl)carbonylamino)propanoic acid, 3-((2,4,8-triaza-1-oxo-4-phenyl-2-benzylspiro[4.5]dec-8-yl)carbonylamino)-2-((2,4,8-triaza-1-oxo-4-phenylspiro[4.5]dec-8-yl)carbonylamino)propanoic acid, 2-((4-(2-methylpropanoylamino)-4-phenylpiperidyl)carbonylamino)-3-((2,4,8-triaza-1-oxo-4-phenylspiro[4.5]dec-8-yl)carbonylamino)propanoic acid, 2-((4-(2-methylpropanoylamino)-4-phenylpiperidyl)carbonylamino)-3-((2,4,8-triaza-2-(2-methylpropyl)-1-oxo-4-phenylspiro[4.5]dec-8-yl)carbonylamino)propanoic acid, 2-((4-(2-methylpropanoylamino)-4-phenylpiperidyl)carbonylamino)-3-((2,4,8-triaza-2-methyl-1-oxo-4-phenylspiro[4.5]dec-8-yl)carbonylamino)propanoic acid, 2-((4-(2-methylpropanoylamino)-4-phenylpiperidyl)carbonylamino)-3-((2,4,8-triaza-2-ethyl-1-oxo-4-phenylspiro[4.5]dec-8-yl)carbonylamino)propanoic acid, 2-((4-(2-methylpropanoylamino)-4-phenylpiperidyl)carbonylamino)-3-((2,4,8-triaza-1-oxo-4-phenyl-2-propylspiro[4.5]dec-8-yl)carbonylamino)propanoic acid, 2-((4-(2-methylpropanoylamino)-4-phenylpiperidyl)carbonylamino)-3-((2,4,8-triaza-1-oxo-4-phenyl-2-benzylspiro[4.5]dec-8-yl)carbonylamino)propanoic acid, 2-((4-(acetylamino)-4-phenylpiperidyl)carbonylamino)-3-((2,4,8-triaza-2-(2-methylpropyl)-1-oxo-4-phenylspiro[4.5]dec-8-yl)carbonylamino)propanoic acid, 2-((4-(acetylamino)-4-phenylpiperidyl)carbonylamino)-3-((2,4,8-triaza-2-methyl-1-oxo-4-phenylspiro[4.5]dec-8-yl)carbonylamino)propanoic acid, 2-((4-(acetylamino)-4-phenylpiperidyl)carbonylamino)-3-((2,4,8-triaza-2-ethyl-1-oxo-4-phenylspiro[4.5]dec-8-yl)carbonylamino)propanoic acid, 2-((4-(acetylamino)-4-phenylpiperidyl)carbonylamino)-3-((2,4,8-triaza-1-oxo-4-phenyl-2-propylspiro[4.5]dec-8-yl)carbonylamino)propanoic acid, 2-((4-(acetylamino)-4-phenylpiperidyl)carbonylamino)-3-((2,4,8-triaza-1-oxo-4-phenyl-2-benzylspiro[4.5]dec-8-yl)carbonylamino)propanoic acid, 2-((4-phenyl-4-(propanoylamino)piperidyl)carbonylamino)-3-((2,4,8-triaza-2-(2-methylpropyl)-1-oxo-4-phenylspiro[4.5]dec-8-yl)carbonylamino)propanoic acid, 2-((4-phenyl-4-(propanoylamino)piperidyl)carbonylamino)-3-((2,4,8-triaza-2-methyl-1-oxo-4-phenylspiro[4.5]dec-8-yl)carbonylamino)propanoic acid, 2-((4-phenyl-4-(propanoylamino)piperidyl)carbonylamino)-3-((2,4,8-triaza-2-ethyl-1-oxo-4-phenylspiro[4.5]dec-8-yl)carbonylamino)propanoic acid, 2-((4-phenyl-4-(propanoylamino)piperidyl)carbonylamino)-3-((2,4,8-triaza-1-oxo-4-phenyl-2-propylspiro[4.5]dec-8-yl)carbonylamino)propanoic acid, 2-((4-phenyl-4-(propanoylamino)piperidyl)carbonylamino)-3-((2,4,8-triaza-1-oxo-4-phenyl-2-benzylspiro[4.5]dec-8-yl)carbonylamino)propanoic acid, 2-((4-(2-oxo(3-hydrobenzimidazolyl))piperidyl)carbonylamino)-3-(2,4,8-triaza-1-oxo-4-phenylspiro[4.5]dec-8-yl)carbonylamino)propanoic acid, 2-((4-(2-oxo(3-hydrobenzimidazolyl))piperidyl)carbonylamino)-3-(2,4,8-triaza-1-oxo-4-phenyl-2-benzylspiro[4.5]dec-8-yl)carbonylamino)propanoic acid, 2-((4-(2-oxo(3-hydrobenzimidazolyl))piperidyl)carbonylamino)-3-(2,4,8-triaza-1-oxo-4-phenyl-2-propylspiro[4.5]dec-8-yl)carbonylamino)propanoic acid, 2-((4-(2-oxo(3-hydrobenzimidazolyl))piperidyl)carbonylamino)-3-(2,4,8-triaza-2-methyl-1-oxo-4-phenylspiro[4.5]dec-8-yl)carbonylamino)propanoic acid, 2-((4-(2-oxo(3-hydrobenzimidazolyl))piperidyl)carbonylamino)-3-(2,4,8-triaza-2-ethyl-1-oxo-4-phenylspiro[4.5]dec-8-yl)carbonylamino)propanoic acid, 2-((4-(2-oxo(3-hydrobenzimidazolyl))piperidyl)carbonylamino)-3-(2,4,8-triaza-2-(2-methylpropyl)-1-oxo-4-phenylspiro[4.5]dec-8-yl)carbonylamino)propanoic acid, 2-(adamantan-2-ylcarbonylamino)-3-((2,4,8-triaza-1-oxo-4-phenylspiro[4.5]dec-8-yl)carbonylamino)propanoic acid, 2-(adamantan-2-ylcarbonylamino)-3-((2,4,8-triaza-1-oxo-4-phenyl-2-benzylspiro[4.5]dec-8-yl)carbonylamino)propanoic acid, 2-(adamantan-2-ylcarbonylamino)-3-((2,4,8-triaza-1-oxo-4-phenyl-2-propylspiro[4.5]dec-8-yl)carbonylamino)propanoic acid, 2-(adamantan-2-ylcarbonylamino)-3-((2,4,8-triaza-2-methyl-1-oxo-4-phenylspiro[4.5]dec-8-yl)carbonylamino)propanoic acid, 2-(adamantan-2-ylcarbonylamino)-3-((2,4,8-triaza-2-ethyl-1-oxo-4-phenylspiro[4.5]dec-8-yl)carbonylamino)propanoic acid, 2-(adamantan-2-ylcarbonylamino)-3-((2,4,8-triaza-2-(2-methylpropyl)-1-oxo-4-phenylspiro[4.5]dec-8-yl)carbonylamino)propanoic acid, 2-((2,6-dichlorophenyl)amino)carbonylamino)-3-((2,4,8-triaza-1-oxo-4-phenylspiro[4.5]dec-8-yl)carbonylamino)propanoic acid, 2-((2,6-dimethylphenyl)amino)carbonylamino)-3-((2,4,8-triaza-1-oxo-4-phenylspiro[4.5]dec-8-yl)carbonylamino)propanoic acid, 2-((2,6-dimethoxyphenyl)amino)carbonylamino)-3-((2,4,8-triaza-1-oxo-4-phenylspiro[4.5]dec-8-yl)carbonylamino)propanoic acid, 2-((2,6-dichlorophenyl)amino)carbonylamino)-3-((2,4,8-triaza-1-oxo-4-phenyl-2-benzylspiro[4.5]dec-8-yl)carbonylamino)propanoic acid, 2-((2,6-dimethylphenyl)amino)carbonylamino)-3-((2,4,8-triaza-1-oxo-4-phenyl-2-benzylspiro[4.5]dec-8-yl)carbonylamino)propanoic acid, 2-((2,6-dimethoxyphenyl)amino)carbonylamino)-3-((2,4,8-triaza-1-oxo-4-phenyl-2-benzylspiro[4.5]dec-8-yl)carbonylamino)propanoic acid, 2-((2,6-dichlorophenyl)amino)carbonylamino)-3-((2,4,8-triaza-2-(2-methylpropyl)-1-oxo-4-phenylspiro[4.5]dec-8-yl)carbonylamino)propanoic acid, 2-((2,6-dimethylphenyl)amino)carbonylamino)-3-((2,4,8-triaza-2-(2-methylpropyl)-1-oxo-4-phenylspiro[4.5]dec-8-yl)carbonylamino)propanoic acid, and 2-((2,6-dimethoxyphenyl)amino)carbonylamino)-3-((2,4,8-triaza-2-(2-methylpropyl)-1-oxo-4-phenylspiro[4.5]dec-8-yl)carbonylamino)propanoic acid, The processes for producing the compounds represented by Formula I (hereinafter, for example, "the compounds represented by Formula I" may also be indicated simply as "Formula I") will now be described. However, the process for producing each of the compounds is not restricted to that described herein. In the various production processes, the reaction conditions may be appropriately selected from those described below.

Among the compounds represented by Formula I, those wherein l=0, m=1, n=1, A is a carbon atom, B is a nitrogen atom, C' and D cooperatively form carbonyl, F is —C(O)—, $R_1$ and $R_2$ are hydrogen atoms, and $R_3$, A and $R_4$ cooperatively form Formula VI, that is, those represented by Formula VIII, or cooperatively form Formula VII, that is, those represented by Formula IX, or A is an oxygen atom, that is, those represented by Formula X:

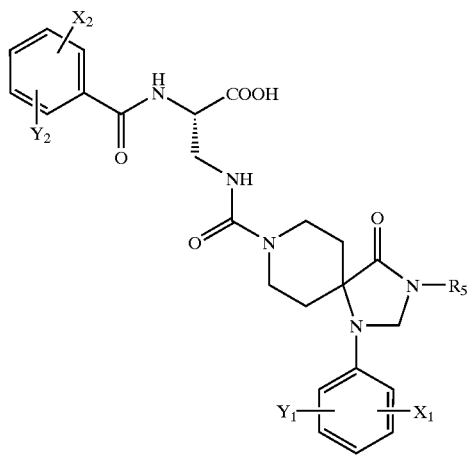

VIII

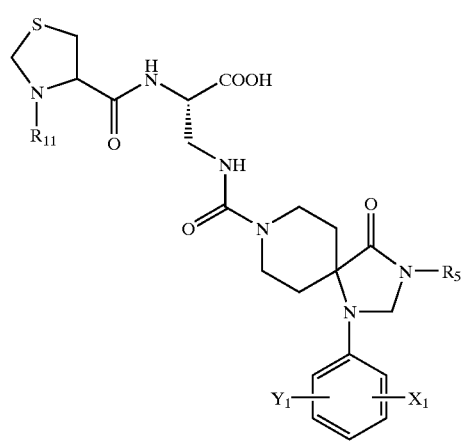

IX

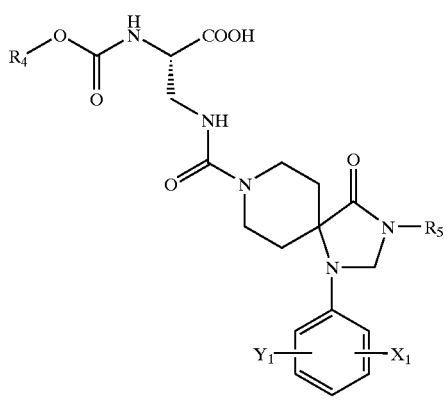

X (wherein $X_1$, $X_2$, $Y_1$, $Y_2$, $R_4$, $R_5$ and $R_{11}$ represent the same meanings as described above) may be produced by hydrolyzing Formula XI, XII or XIII:

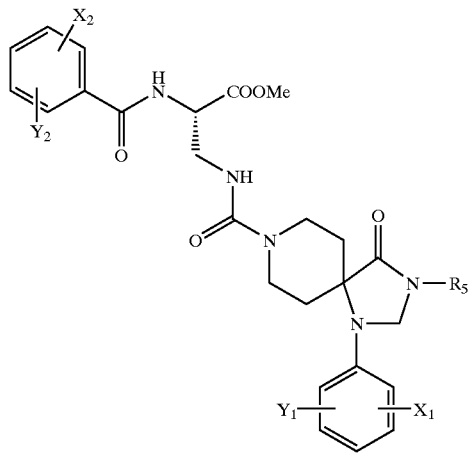

XI

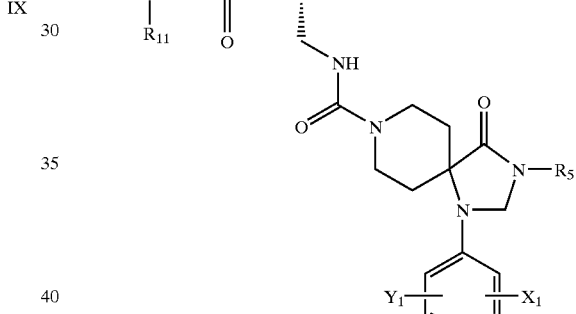

XII

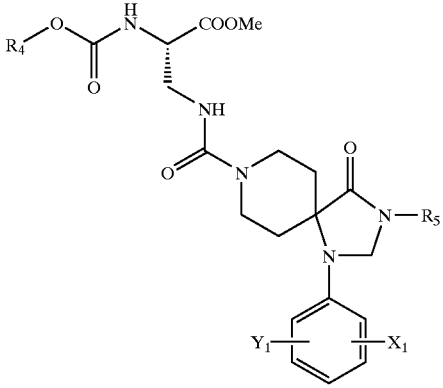

XIII (wherein $X_1$, $X_2$, $Y_1$, $Y_2$, $R_4$, $R_5$ and $R_{11}$ represent the same meanings as described above) by a base such as aqueous sodium hydroxide solution or aqueous barium hydroxide solution in an alcoholic solvent such as methanol. The hydrolysis by the base such as aqueous sodium hydroxide solution or aqueous barium hydroxide solution may usually be carried out at about 0° C. to room temperature for about 1 hour to 24 hours, although the reaction conditions are not restricted thereto. The amount of the base to be added is not restricted, and may usually be about 1 to 4 equivalents with respect to Formula XI, XII or XIII.

Formula XI, XII and XIII may be produced from Formula XIV, XV and XVI:

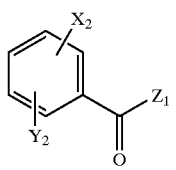
XIV

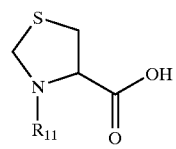
XV

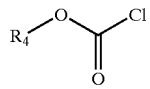
XVI (wherein $X_2$, $Y_2$, $R_4$, and $R_{11}$ represent the same meanings as described above, $Z_1$ represents chloro, bromo or hydroxyl), respectively, and Formula XVII:

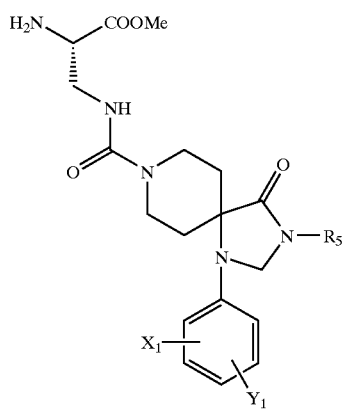
XVII (wherein $X_1$, $Y_1$ and $R_5$ represent the same meanings as described above).

In cases where one represented by Formula XIV wherein $Z_1$ is chloro or bromo, or one represented by Formula XVI is used, the desired product may be produced by reacting Formula XIV or Formula XVI with Formula XVII in a solvent such as tetrahydrofuran, dimethylformamide, chloroform, dichloromethane or 1,4-dioxane in the presence of a tertiary amine such as triethylamine or diisopropylamine. The reaction between Formula XIV or XVI and XVII may usually be carried out at about 0° C. to room temperature for about 1 hour to 24 hours, although the reaction conditions are not restricted thereto. The mixing ratio (molar ratio; unless otherwise specified, the term "mixing ratio" means molar ratio in the description below) of Formula XIV or XVI to Formula XVII may be, although not restricted, about 1:1 to 2:1, and the amount of the tertiary amine to be added is, although not restricted, about 1 to 4 equivalents with respect to Formula XIV or XVI.

In cases where a compound of Formula XIV wherein $Z_1$ is hydroxyl, or Formula XV is used, usually, a condensing agent such as dicyclohexylcarbodiimide (DCC), benzotriazol-1-yloxytris(dicyclopentylamino) phosphoniumhexafluoro phosphite salt (PyBOP), benzotriazol-1-yloxytris(dimethylamino)phosphonium-hexafluoro phosphite salt (BOP), diphenylphosphoryl azide (DPPA) or 1-ethyl-3-[3-(dimethylamino))propyl] carbodiimide (WSC) is used in a solvent such as tetrahydrofuran, dimethylformamide, chloroform or dichloromethane in the presence of a tertiary amine such as triethylamine, diisopropylamine or N-methylmorpholine. The amount of such a condensing agent to be added is not restricted, and usually about 1 to 3 equivalents with respect to Formula XIV or XV. Addition of an additive such as 1-hydroxybenzotriazole (HOBT) may be advantageous in the proceeding of the reaction in some cases.

Formula XI, XII and XIII may also be produced by treating Formula XVIII

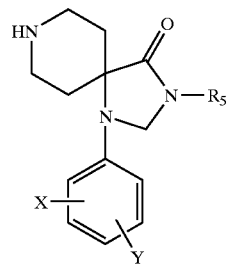
XVIII

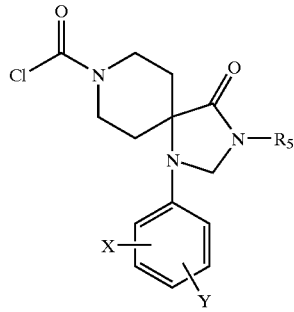
XIX (wherein $X_1$, $Y_1$, and $R_5$ represent the same meanings as described above)

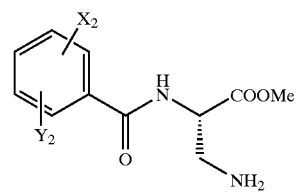
XX

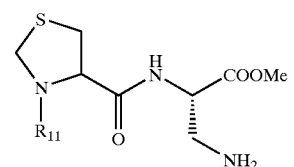
XXI

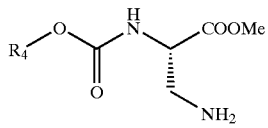

XXII with usually 0.5 to 2 equivalents of diphosgene, triphosgene, 1,1-carbonyldiimidazole or the like in a solvent such as dichloromethane or chloroform, in the presence of a tertiary amine such as triethylamine or diisopropylamine, and by reacting the obtained product with Formula XX, XXI and XXII, respectively. The mixing ratio of Formula XVIII to Formula XX, XXI or XXII may usually be, although not restricted, about 1:1 to 2:1, and the reaction may usually be carried out at about 0° C. to room temperature for about 1 hour to 24 hours. The amount of the tertiary amine is not restricted, and is usually about 1 to 4 equivalents with respect to diphosgene, triphosgene or 1,1-carbonyldiimidazole. Alternatively, the desired product may be obtained by reacting Formula XX, XXI or XXII with Formula XIX in a solvent such as dimethylformamide, tetrahydrofuran or dimethoxyethane at about 0° C. to room temperature for about 1 to 24 hours. The mixing ratio of Formula XX, XXI or XXII to XIX is not restricted, and usually about 1:1 to 1:3. Alternatively, the desired product may be obtained by reacting Formula XX, XXI or XXII with p-nitrophenyl chloroformate or phenyl chloroformate in a solvent such as acetonitrile, dichloromethane or dimethoxyethane, in the presence of a base such as sodium hydrogen carbonate or tribenzylamine (first step); and then reacting the obtained product with Formula XVIII in a solvent such as acetonitrile, dichloromethane or dimethoxyethane, in the presence of a tertiary amine such as triethylamine or diisopropylamine (second step). In this method, the amount of the base such as sodium hydrogen carbonate or tribenzylamine used in the reaction is not restricted, and usually about 1 to 4 equivalents with respect to p-nitrophenyl chloroformate or phenyl chloroformate. The amount of the tertiary amine to be added is not restricted, and usually about 1 to 4 equivalents with respect to Formula XVIII.

In the first step, the reaction temperature of the reaction between Formula XX, XXI or XXII and p-nitrophenyl chloroformate or phenyl chloroformate is not restricted, and usually about 0° C. to room temperature. The reaction temperature in the second step may usually be about 0° C. to 50° C. when p-nitrophenyl chloroformate is used, and may usually be about room temperature to refluxing temperature when phenyl chloroformate is used.

Formula XVII may be produced by the following steps:

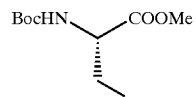

XXIII

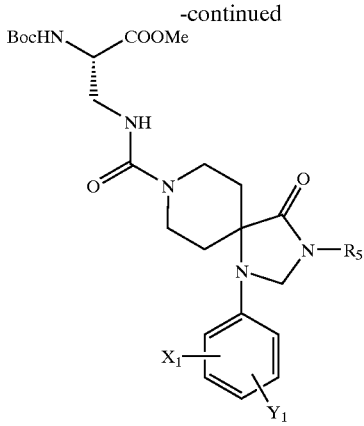

XXIV

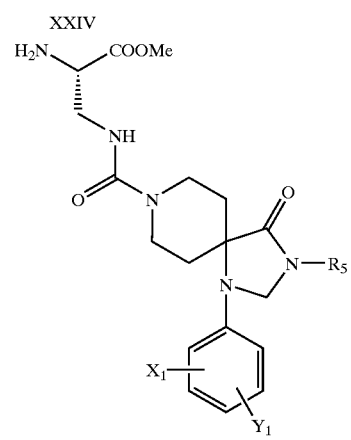

XVII (wherein $X_1$, $Y_1$ and $R_5$ represent the same meanings as described above).

Step 1 may be carried out in the same manner as in the reaction between Formula XVIII or XIX and XX, XXI or XXII.

Step 2 is the step of removing t-butoxycarbonyl group (referred to as "Boc" for short) on the nitrogen atom. This step may be carried out by usually using trifluoroacetic acid, hydrochloric acid, hydrobromic acid or the like in a halogen-containing solvent such as chloroform or dichloromethane. Alternatively, this step may be carried out by using trifluoroacetic acid alone. The reaction temperature is not restricted, and usually a temperature between 0° C. and room temperature is selected. The reaction time may be appropriately selected depending on the reaction temperature and the like, and usually, the reaction time may be about 1 to 24 hours.

Formula XX may be produced by the following step using commercially available asparagine XXV as a starting material:

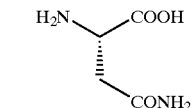

XXV

-continued

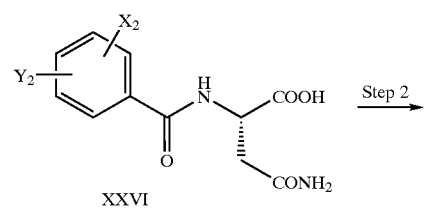

XXVI

Step 2

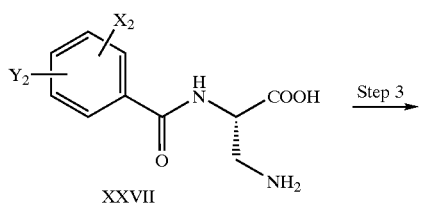

XXVII

Step 3

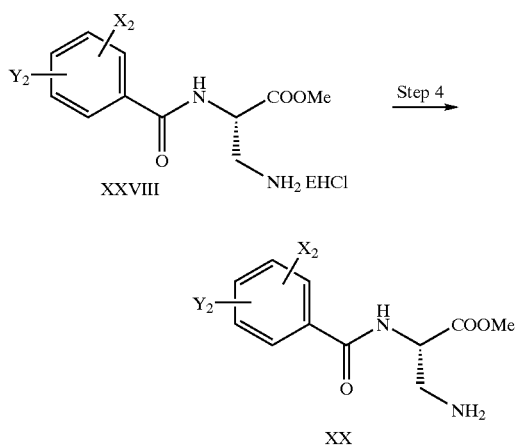

XXVIII

Step 4

XX (wherein $X_2$ and $Y_2$ represent the same meanings as described above).

Step 1 may be carried out in the same manner as in the reaction between Formula XIV and XVII using Formula XXV and XIV. In cases where $Z_1$ in Formula XIV is chloro or bromo, aqueous sodium hydroxide solution, aqueous potassium hydroxide solution or the like may be used as the base.

Step 2 may be carried out by reacting Formula XXVI and bromine in a basic solvent such as aqueous sodium hydroxide solution, aqueous potassium hydroxide solution or the like, for about 1 to 8 hours, although not restricted. The reaction temperature is not restricted, and is usually about room temperature to 100° C. Bromine is usually used in excess to Formula XXVI. This step may also be carried out by the method described in J. Org. Chem., 62, 6918(1997) or J. Org. Chem., 49, 4272(1984).

Step 3 may be carried out by using thionyl chloride in a solvent such as methanol at about 0° C. to room temperature. The reaction time is not restricted, and usually about 1 to 8 hours. The mixing ratio of Formula XXVII to thionyl chloride is not restricted, and is usually about 1:1 to 1:10. The reaction may also be carried out by treating the product with an excess amount of diazomethane or trimethylsilyl-diazomethane in a solvent such as methanol at about 0° C. to room temperature.

Step 4 may be carried out by using aqueous sodium hydroxide solution, aqueous potassium hydroxide solution or aqueous potassium carbonate solution, in an excess amount with respect to Formula XXVIII, in a solvent such as chloroform or dichloromethane at about 0° C. to room temperature.

Formula XXIII may be produced by the following steps using commercially available Formula XXIX.

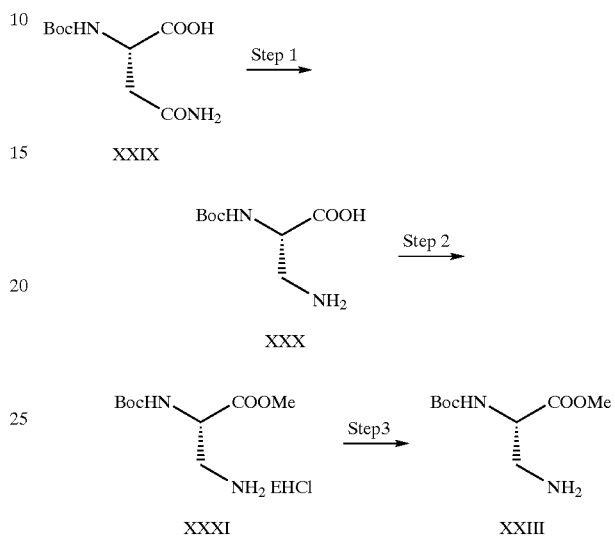

Step 1 may be carried out in the same manner as in step 2 in the process of producing Formula XX.

Step 2 may be carried out in the same manner as in step 3 in the process of producing Formula XX.

Step 3 may be carried out in the same manner as in step 4 in the process of producing Formula XX.

Among the compounds represented by Formula I, those wherein l=0, m=1, n=1, both $R_1$ and $R_2$ are hydrogen atoms, both A and B are nitrogen atoms, C' and D cooperatively form carbonyl, F is —C(O)—, and $R_3$, A and $R_4$ cooperatively form Formula II, IV or V, that is, those represented by Formula XXXII, XXXIII and XXXIV:

XXXII

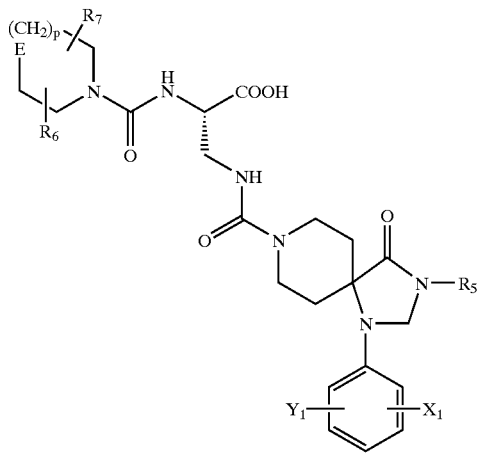

XXXIII

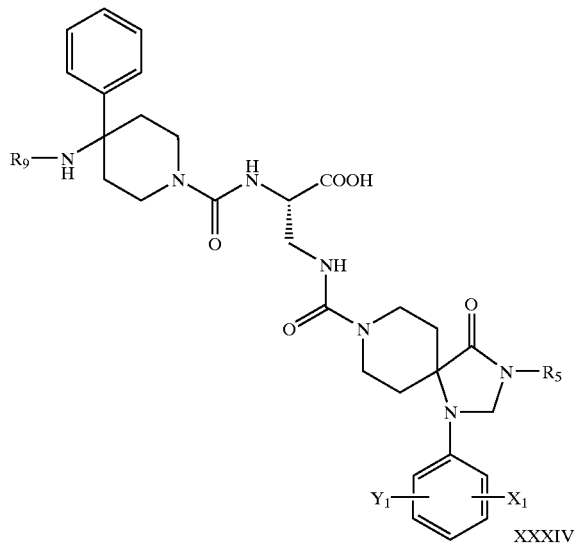

XXXVI

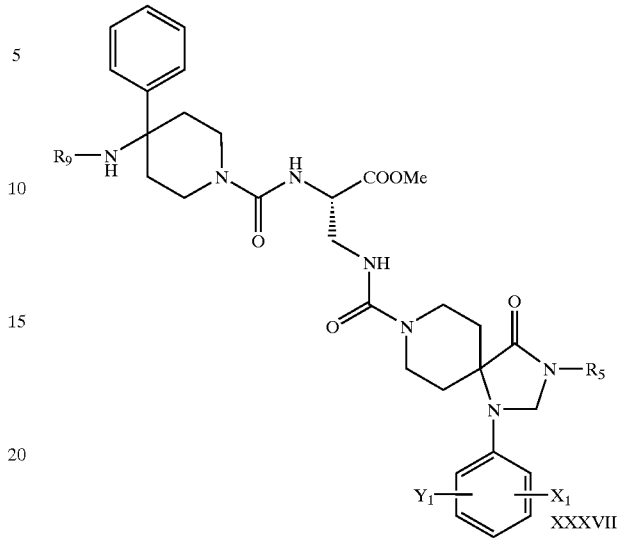

XXXIV

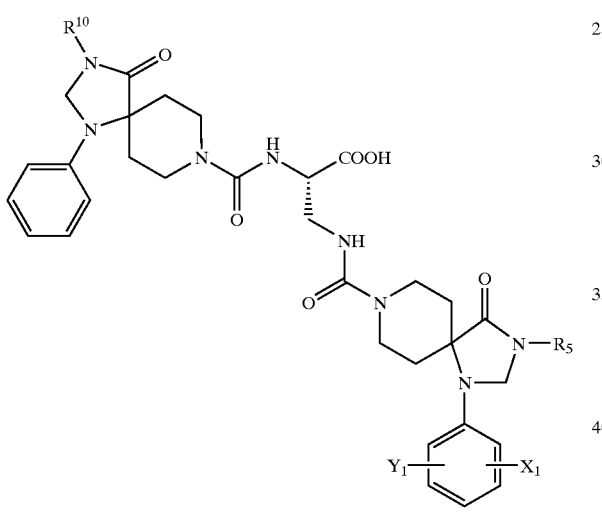

XXXVII

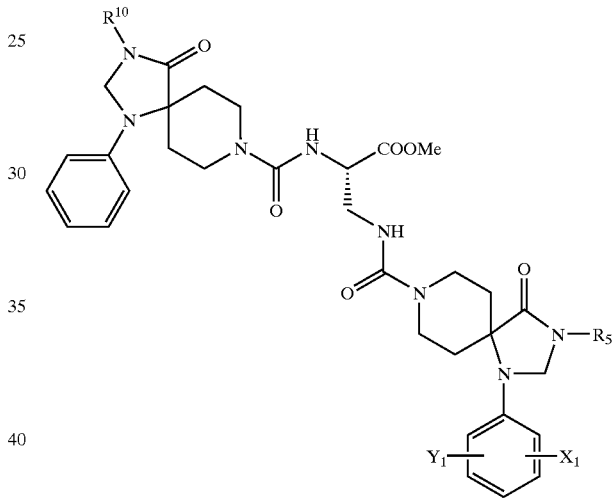

(wherein $X_1$, $Y_1$, $R_5$, $R_6$, $R_7$, $R_9$ and $R_{10}$ represent the same meanings as described above) may be produced by hydrolyzing Formula XXXV, XXXVI and XXXVII:

XXXV

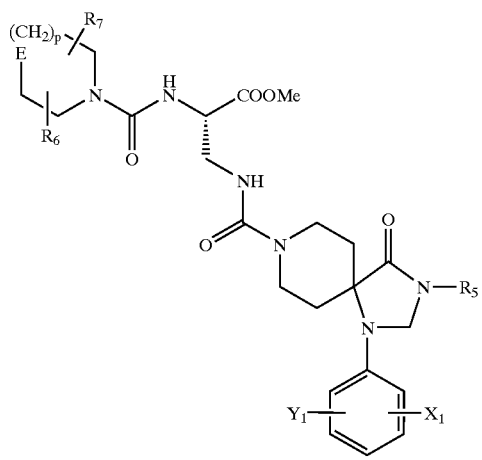

(wherein $X_1$, $Y_1$, $R_5$, $R_6$, $R_7$, $R_9$ and $R_{10}$ represent the same meanings as described above), respectively, in an alcoholic solvent such as methanol by a base such as aqueous sodium hydroxide solution or aqueous barium hydroxide solution. The hydrolysis by the base such as aqueous sodium hydroxide solution or aqueous barium hydroxide solution may be carried out, although not restricted, usually at about 0° C. to room temperature. The amount of the base to be added is not restricted and usually about 1 to 4 equivalents with respect to Formula XXXV, XXXVI or XXXVII.

Formula XXXV, XXXVI and XXXII may be produced in the same manner as in step 1 in the process of producing Formula XVII, by using Formula XVII and Formula XXXVIII, XXXIX and XXXX:

XXXVIII

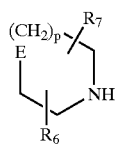

XXXIX

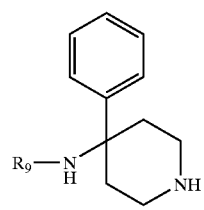

XXXX

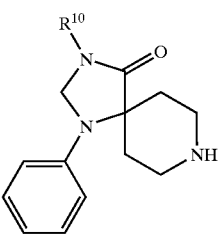

(wherein $R_6$, $R_7$, $R_9$ and $R_{10}$ represent the same meanings as described above), respectively.

Alternatively, Formula XXXV, XXXI or XXXVII may also be produced by reacting Formula XXXXI, XXXXII or XXXXIII with Formula XVIII or Formula XIX. This production process may be carried out as in step 1 in the production process of Formula XVII.

XXXXI

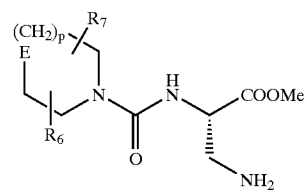

XXXXII

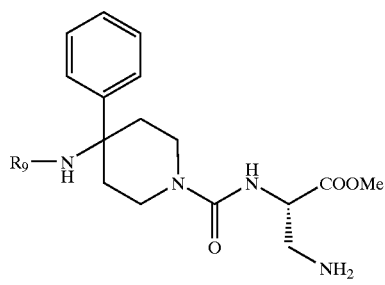

XXXXIII

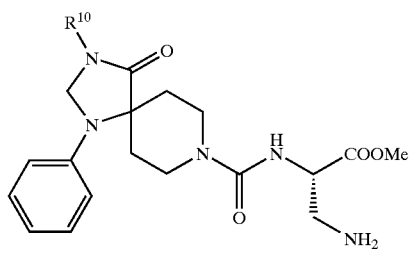

(wherein $R_6$, $R_7$, $R_9$ and $R_{10}$ represent the same meanings as described above).

Among the compounds represented by Formula I, those wherein l=0, m=1, n=1, A is a carbon atom, B is a nitrogen atom, C' and D cooperatively form carbonyl, F is —$CH_2$—, $R_1$ and $R_2$ are hydrogen atoms, $R_3$, A and $R_4$ cooperatively form Formula VI, that is, those represented by Formula XXXXIV:

XXXXIV

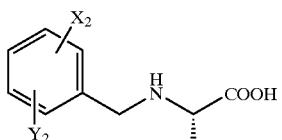

(wherein $X_1$, $X_2$, $Y_1$ and $Y_2$ represent the same meanings as described above) may be produced by reacting Formula XVII and Formula XXXXV:

XXXXV

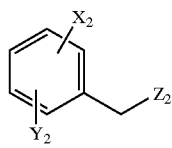

(wherein $X_2$ and $Y_2$ represent the same meanings as described above, and $Z_2$ represents a leaving group such as halogen) in a solvent such as tetrahydrofuran, dichloromethane, dimethylformamide or acetonitrile, in the presence of a tertiary amine such as triethylamine or diisopropylamine at, although not restricted, usually room temperature to refluxing temperature for about 1 to 24 hours, and then hydrolyzing the reaction product under the same conditions for producing Formula VIII from Formula XI. The mixing ratio of Formula XVII to Formula XXXXV is about 1:1 to 1:2. The amount of the tertiary amine to be added is not restricted, and usually 1 to 4 equivalents with respect to Formula XXXXV.

In cases where the novel spiro derivatives used in the present invention have one or more asymmetric carbon atoms, there exist racemic compounds, diastereomers and optical isomers. In the present invention, any of these may be used.

The reaction products obtained by the above-described processes may be isolated and purified in the form of a free compound, a salt or a solvate such as hydrate. The salt may be produced by a usual salt-producing treatment.

Isolation and purification may be carried out by ordinary chemical processes such as extraction, condensation, evaporation, crystallization, filtration, recrystallization and various column chromatography.

Various isomers may be isolated by conventional methods utilizing the differences in the physicochemical properties between the isomers. Optical isomers may be separated by a general optical resolution method such as fractional crystallization or chromatography. Optical isomers may also be produced by an appropriate optically active compound as the starting material.

Examples of the pharmaceutically acceptable salts of the compounds represented by Formula I include inorganic salts such as ammonium salt, alkaline metal salts (e.g., sodium salt and potassium salt), alkaline earth metal salts (e.g., calcium salt and magnesium salt); organic salts such as dicyclohexylamine salt, N-methyl-D-glucamine salt, ethanolamine salt, diethanolamine salt, triethanolamine salt, diisopropanolamine salt and tris(hydroxymethyl) aminomethane salt; and lysine- and arginate-addition salts.

Further, various hydrates, solvates and crystalline polymorphs of the compounds (1) of the present invention and the salts thereof are included within the scope of the present invention.

The inhibitory activity of the compound according to the present invention against the adhesion of VLA-4 may be determined by using an adhesion-measuring system in which the adhesion between VLA-4-expressing cells such as Ramos cells or Jurkat cells and fibronectin or fibronectin fragment such as a peptide containing CS-1 sequence (Gly Pro Glu Ile Leu Asp Val Pro Ser Thr) (hereinafter referred to as "CS-1 peptide"), immobilized on an immunoplate is measured. Alternatively, a binding-measuring system in which the adhesion between VLA-4 protein and fibronectin or fibronectin fragment such as CS-1 peptide, immobilized on an immunoplate may be used. In the present invention, it is preferred to evaluate the inhibitory activity of a compound using a binding-measuring system in which adhesion between a chimera protein of VLA-4-immunoglobulin (VLA-4-IgG chimera protein) and CS-1 peptide (Japanese Patent Application No. H9-234544), but the method is not restricted thereto. The "VLA-4-IgG chimera protein" herein means the heterodimer complex of the chimera protein between α4 of VLA-4 and immunoglobulin (hereinafter referred to as "VLAα4-IgG chimera protein") and a chimera protein between β1 of VLA-4 and immunoglobulin (hereinafter referred to as "VLAβ1-IgG chimera protein"). As the immunoglobulin, although heavy chain or light chain of IgG, IgM or the like may be used, IgG1 heavy chain is used in the present invention. When testing the inhibitory effect of a compound, it is preferred to mix VLA-4-IgG chimera protein and the test compound previously.

Since the compounds according to the present invention have inhibitory activities against adhesion of VLA-4, and so inhibit accumulation of leukocytes at the inflammatory site, they may be used as therapeutic drugs against chronic inflammatory diseases. Examples of the chronic inflammatory diseases include allergic inflammatory diseases such as bronchial asthma, atopic dermatitis and allergic rhinitis, hepatitis, nephritis, autoimmune diseases such as chronic rheumatoid arthritis and multiple sclerosis, graft rejections after organ transplantation, type I diabetes, Crohn's disease and ulcerative colitis. In addition to these, they may be used as therapeutic drugs for the prevention of postoperative restenosis, arteriosclerosis and the like.

When using the compound of the present invention as a therapeutic drug against the above-mentioned diseases, the compound represented by Formula I or a base addition salt thereof may be administered as it is in the form of powder, or may be administered as a medical composition in the form of an appropriate formulation, orally or parenterally (e.g., percutaneous administration, intravenous administration, rectal administration and inhalation) to mammals.

Examples of the formulation for administration include tablets, powders, balls, capsules, granules, syrups, liquids, injection solutions, emulsions, suspensions and suppositories. These formulations may be prepared by the methods which per se are known, and contain various carriers usually used in the field of formulation. Examples thereof include vehicles, lubricants, binders and disintegrators for solid formulations; and solvents, solubilizers, suspending agents and soothing agents for liquid formulations. Additives such as antiseptics, antioxidants, coloring agents, sweeteners, absorbents, and wetting agents may be used.

Examples of the vehicles include lactose, D-mannitol, starch, sucrose, corn starch, crystalline cellulose and light anhydrous silicic acid. Examples of the lubricants include magnesium stearate, calcium stearate, talc and colloidal silica. Examples of the binders include crystalline cellulose, saccharose, D-mannitol, dextrin, hydroxypropyl cellulose, hydroxypropylmethyl cellulose, polyvinylpyrrolidone, starch, sucrose, gelatin, methyl cellulose and sodium carboxymethyl cellulose. Examples of the disintegrators include starch, carboxymethyl cellulose, calcium carboxymethyl cellulose, cross carmelose sodium, sodium carboxymethyl starch and L-hydroxypropyl cellulose. Examples of the solvents include water for injection, alcohol, propylene glycol, Macrogol, sesame oil and corn oil. Examples of the solubilizers include polyethylene glycol, propylene glycol, D-mannitol, benzyl benzoate, ethanol, cholesterol, triethanolamine, sodium carbonate and sodium citrate. Examples of the suspending agents include surfactants such as stearyl triethanolamine, sodium lauryl sulfate, laurylamino propionate, lecithin, benzalkonium chloride, benzethonium chloride and glycerin monostearate, and hydrophilic macromolecules such as polyvinyl alcohol, polyvinyl pyrrolidone, methyl cellulose, hydroxymethyl cellulose, hydroxyethyl cellulose and hydroxypropyl cellulose. Examples of the isotonic agents include glucose, sodium chloride, D-sorbitol and D-mannitol. Examples of the buffering agents include buffering solutions containing a phosphoric acid salt, acetic acid salt, carbonic acid salt or citric acid salt. An example of the soothing agents is benzylalcohol. Examples of the antiseptics include p-oxybenzoic acid esters, chlorobutanol, benzylalcohol, phenetyl alcohol, dehydroacetic acid and sorbic acid. Examples of the antioxidants include sulfurous acid salts and ascorbic acid.

The effective dose and the number of times of administration of the compounds represented by Formula I and pharmaceutically acceptable salts thereof differ depending on the administration form, age and bodyweight of the patient, the type and severity of the disease to be treated, and usually, 1 to 1000 mg, preferably 1 to 300 mg of the compound may be administered once or in several times per day per adult.

The above-mentioned formulations may contain one or more other effective components for therapy of other disease (s). Examples thereof include steroid drugs, nonsteroidal anti-inflammatory drug, lipoxygenase inhibitors, leucotriene inhibitors, bronchodilators, thromboxane synthesis inhibitors, thromboxane antagonists, histamine antagonists, histamine release inhibitors, platelet activating factor (PAF) inhibitors, serotonin antagonist, adenosine receptor antagonists, adrenalin β receptor stimulators, immunosuppressors and immunomodulators.

The effect of the present invention will now be described concretely by way of examples thereof. It should be noted that the present invention is not restricted to the examples.

EXAMPLE 1

Methyl 2-((t-butoxy)carbonylamino)-3-((2,4,8-triaza-1-oxo-4-phenyl-2-benzylspiro[4.5]dec-8-yl)carbonylamino)propionate (1)

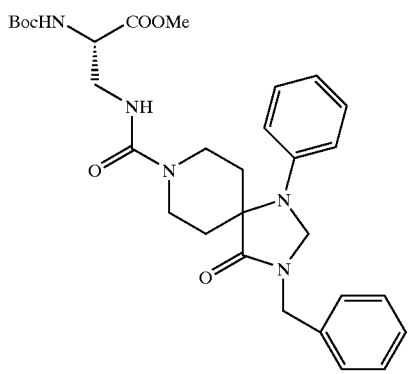

(1)

Under argon atmosphere, 672 mg of methyl 3-amino-2-((t-butoxy)carbonylamino)propionate was dissolved in 15 ml of acetonitrile and 15 ml of dichloromethane, and then 414 mg of saturated sodium hydrogen carbonate and 746 mg of chloroformic acid p-nitrophenyl ester were added thereto while cooling the mixture in ice, followed by stirring the resulting mixture at room temperature for 2.5 hours. To the reaction mixture, 1.385 g of 2,4,8-triaza-4-phenyl-2-benzylspiro[4.5]decane-1-one and 2.1 ml of triethylamine were added, and the resulting mixture was stirred at room temperature for 24 hours. After concentrating the reaction mixture, saturated aqueous sodium hydrogen carbonate solution was added, and the resulting mixture was extracted with chloroform. The organic layers were combined, washed with 0.1N hydrochloric acid and with saturated saline, dried over anhydrous sodium sulfate and concentrated. The residue was purified by column chromatography (dichloromethane/methanol=80:1) to obtain 1.275 g of methyl 2-((t-butoxy)carbonylamino)-3-((2,4,8-triaza-1-oxo-4-phenyl-2-benzylspiro[4.5]dec-8-yl)carbonylamino) propionate (yield: 73%).

LR-MS(m/z): 565(M+) NMR(300 MHz,CDCl3, δ ppm): 1.43(9H,s),1.62–1.75(2H,m),2.47–2.62(2H,m),3.53–3.80 (3H,m),3.74(3H,s),3.81–3.98(2H,m),4.32–4.42(1H,m),4.55 (2H,s), 4.60(2H,s), 5.42(1H,brs),5.93(1H,brs),6.63–6.71 (2H,m),6.78–6.84(1H,m), 7.20–7.40(7H,m)

EXAMPLE 2

Methyl 2-amino-3-((2,4,8-triaza-1-oxo-4-phenyl-2-benzylspiro[4.5]dec-8-yl)carbonylamino)propionate (2)

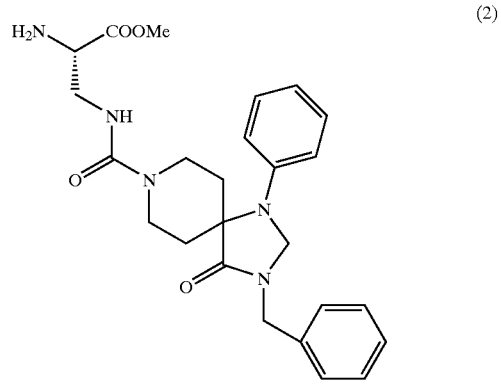

(2)

In 2 ml of dichloromethane, 45 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 1 ml of trifluoroacetic acid was added thereto, followed by stirring the resulting mixture at room temperature for 2 hours. After concentrating the reaction mixture, saturated aqueous sodium hydrogen carbonate solution was added to the residue, and the resulting mixture was extracted with chloroform. Organic layers were combined, washed with saturated saline, dried over anhydrous sodium sulfate and concentrated to obtain 41 mg of methyl 2-amino-3-((2,4,8-triaza-1-oxo-4-phenyl-2-benzylspiro[4.5]dec-8-yl)carbonylamino)propionate.

NMR(300 MHz,CDCl$_3$, δ ppm): 1.72–1.85(2H,m), 2.36–2.42(2H,m),3.40–4.20(6H,m),3.80(3H,s),4.15–4.21 (1H,m),4.56(2H,s),4.58(2H,s),4.96(1H,brs), 6.64–6.70(2H, m),6.83–6.90(1H,m),7.15–7.60(7H,m)

EXAMPLE 3

3-((2,4,8-triaza-1-oxo-4-phenylspiro[4.5]dec-8-yl)carbonylamino)-2-((2,6-dichlorophenyl)carbonylamino)propanoic acid (3)

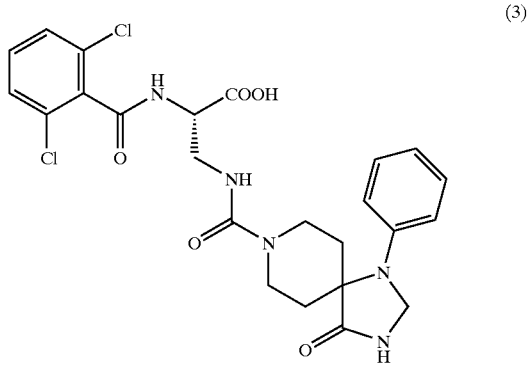

(3)

In 3.0 ml of DMF, methyl 3-amino-2-((2,6-dichlorophenyl)carbonylamino)propionate (175 mg, 0.601 mmol) was dissolved, and 2,4,8-triaza-1-oxo-4-phenylspiro[4.5]decane-8-carbonyl chloride (177 mg, 0.601 mmol) and triethylamine (250 μl, 1.80 mmol) were added thereto, followed by stirring the resulting mixture at room temperature for 6 hours. After adding water to the reaction solution, precipitated solids were recovered by filtration and washed with water. The solids were dissolved in 3 ml of methanol, and 1 ml of 1N aqueous sodium hydroxide solution was added thereto, followed by stirring the mixture at room temperature for 2 hours. To the reaction solution, 1N hydrochloric acid was added, and precipitated solids were recovered by filtration. The obtained solids were purified by column chromatography (ethyl acetate/methanol=1/1) to obtain 122 mg of 3-((2,4,8-triaza-1-oxo-4-phenylspiro[4.5]dec-8-yl)carbonylamino)-2-((2,6-dichlorophenyl)carbonylamino)propanoic acid (yield: 38%).

LR-MS(m/z): 533($M^+$) IR(KBr): 3422, 2921, 1708, 1656, 1543, 1432, 1376, 1254 $cm^{-1}$ NMR(300 MHz,$CD_3OD$, δ ppm): 1.68–1.80 (m, 2H), 2.50–2.64 (m, 2H), 3.55–3.80 (m, 4H), 3.90–4.05 (m, 2H), 4.75 (s, 2H), 4.80–4.90 (m, 1H), 6.80–6.90 (m, 3H), 7.23–7.35 (m, 2H), 7.38–7.50 (m, 3H). HR-MS: $C_{24}H_{25}Cl_2N_5O_5$ Calcd.: 532.1154. Found: 532.1140. $[\alpha]^{20}_D$: −10.5° (c=0.30,MeOH)

EXAMPLE 4

2-((2,6-diemthoxyphenyl)carbonylamino)-3-((2,4,8-triaza-1-oxo-4-phenylspiro[4.5]dec-8-yl)carbonylamino)propanoic acid (4)

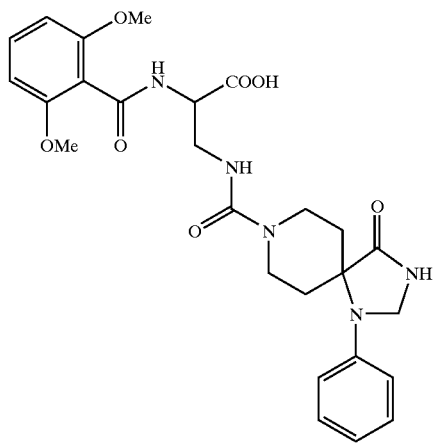

(4)

In 10 ml of dichloromethane, 199.2 mg of methyl 2-((t-butoxy)carbonylamino)-3-((2,4,8-triaza-1-oxo-4-phenylspiro[4.5]dec-8-yl)carbonylamino)propionate was dissolved, and 2 ml of trifluoroacetic acid was added thereto, followed by stirring the resulting mixture at room temperature for 6 hours. After concentrating the reaction solution, the residue was dissolved in 2 ml of dimethylformamide, and then 187 mg of BOP, 70 mg of 2,6-dimethoxybenzoic acid and 265 μl of diisopropylamine were added thereto, followed by stirring the resulting mixture under argon atmosphere at room temperature for 2 hours. To the reaction mixture, 1N hydrochloric acid was added, and the resulting mixture was extracted with chloroform. Organic layers were combined, washed with saturated aqueous sodium hydrogen carbonate solution and with saturated saline, dried over anhydrous sodium sulfate, and concentrated. The residue was dissolved in 10 ml of methanol, and then 1 ml of 1N aqueous sodium hydroxide solution was added thereto, followed by stirring the resulting mixture at room temperature for 3 hours. To the reaction mixture, 0.1N hydrochloric acid was added, and the resulting mixture was extracted with chloroform. Organic phases were combined, washed with saturated saline, dried over anhydrous sodium sulfate, and concentrated. The residue was purified by column chromatography (DIOL, ethyl acetate/methanol=20:1) to obtain 44.6 mg of 2-((2,6-diemthoxyphenyl)carbonylamino)-3-((2,4,8-triaza-1-oxo-4-phenylspiro[4.5]dec-8-yl)carbonylamino)propanoic acid (yield: 20%).

LR-MS(m/z): 524($M^+$−H) IR(KBr): 3408,2927,1656, 1602,1542,1468,1432,1381,1262,1196,800,749 $cm^{-1}$ NMR (300 MHz,$CDCl_3$, δ ppm): 1.68–1.80(2H,m),2.41–2.61 (2H, m),3.45–3.57(1H,m),3.62–3.74(2H,m),3.79(6H,s), 3.82–3.97(3H,m),4.52–4.57(1H,m),4.70(2H,s),6.18(1H, brs),6.53–6.58(2H,m),6.71–6.78(2H,m), 6.83–6.91 (1H,m), 7.11 (1H,brs),7.21–7.32(2H,m),7.43–7.48(1H,m) HR-MS: $C_{26}H_{30}N_5O_7$ Calcd.: 524.2145. Found: 524.2173. $[\alpha]^{20}_D$: −10.0° (c=0.07,MeOH)

EXAMPLE 5

2-((2,6-dimethoxyphenyl)carbonylamino)-3-((2,4,8-triaza-1-oxo-4-phenyl-2-benzylspiro[4.5]dec-8-yl)carbonylamino)propanoic acid (5)

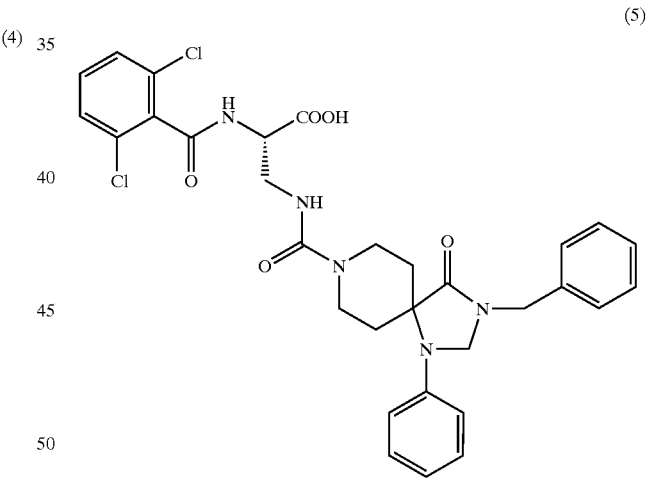

(5)

In 5 ml of acetonitrile, 120 mg of methyl 3-amino-2-((2,6-dichlorophenyl)carbonylamino)propionate was dissolved, and 55 mg of saturated sodium hydrogen carbonate and 83 mg of chloroformic acid p-nitrophenyl ester were added thereto, followed by stirring the resulting mixture at room temperature for 2 hours. To the reaction mixture, 139 mg of 2,4,8-triaza-4-phenyl-2-benzylspiro[4.5]decane-1-one and 143 μl of triethylamine were added, and the resulting mixture was stirred at room temperature for 3 hours. After concentrating the reaction mixture, saturated aqueous sodium hydrogen carbonate solution was added, and the resulting mixture was extracted with ethyl acetate. Organic layers were combined, washed with 1N hydrochloric acid and with saturated saline, dried over anhydrous sodium sulfate, and concentrated. The residue was dissolved in 2 ml of methanol, and then 0.5 ml of 1N aqueous sodium hydroxide solution was added thereto, followed by stirring the resulting mixture at room temperature for 4 hours. To the reaction mixture, 0.1N hydrochloric acid was added, and the resulting mixture was extracted with chloroform. Organic phases were combined, washed with saturated saline, dried over anhydrous sodium sulfate, and concentrated. The residue was purified by column chromatography (DIOL, ethyl acetate/cyclohexane=2:1) to obtain 18 mg of 2-((2,6-dimethoxyphenyl)carbonylamino)-3-((2,4,8-triaza-1-oxo-4-phenyl-2-benzylspiro[4.5]dec-8-yl)carbonylamino) propanoic acid (yield: 7%).

LR-MS(m/z): 622(M$^+$–H) IR(KBr): 3385,2934,2841, 1709,1637,1599,1534,1474,1434,1377,1254,1111,753 cm$^{-1}$ NMR(300 MHz,CD$_3$OD, δ ppm): 1.64–1.73(2H,m), 2.43–2.57(2H,m),3.60–3.77(4H,m),3.88–3.98(2H,m), 3.82–3.97(3H,m),4.41(2H,s),4.79–4.83(1H,m),4.86(2H,s), 6.75–6.82(3H,m),7.18–7.25(2H,m),7.24–7.44(8H,m) HR-MS: C$_{31}$H$_{30}$Cl$_2$N$_5$O$_5$ Calcd.: 622.1624. Found: 622.1669. [α]$^{20}$$_D$: –11.6° (c=0.11,MeOH)

EXAMPLE 6

Methyl 2-((2,6-dimethoxyphenyl)carbonylamino)-3-((2,4,8-triaza-1-oxo-4-phenyl-2-benzylspiro[4.5]dec-8-yl)carbonylamino)propionate (6)

(6)

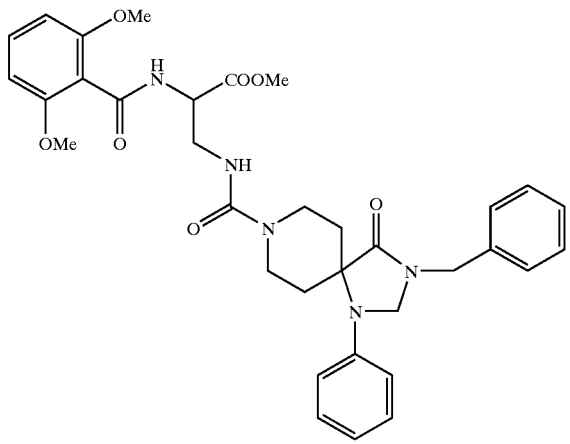

In 2 ml of dichloromethane, 49 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 1 ml of trifluoroacetic acid was added thereto, followed by stirring the resulting mixture at room temperature for 1.5 hours. After concentrating the reaction solution, 3 ml of dichloromethane, 44 mg of BOP, 18 mg of 2,6-dimethoxybenzoic acid and 61 μl of diisopropylamine were added to the residue, and the resulting mixture was stirred at room temperature under argon atmosphere for 3 hours. To the reaction mixture, 1N hydrochloric acid was added, and the resulting mixture was extracted with chloroform. Organic layers were combined, washed with saturated sodium hydrogen carbonate solution and with saturated saline, dried over anhydrous sodium sulfate, and concentrated. The residue was purified by column chromatography (dichloromethane/methanol=30:1) to obtain 22 mg of methyl 2-((2,6-dimethoxyphenyl)carbonylamino)-3-((2,4,8-triaza-1-oxo-4-phenyl-2-benzylspiro[4.5]dec-8-yl) carbonylamino) propionate (yield: 40%).

LR-MS(m/z): 629(M$^+$) IR(KBr): 2934, 1743, 1698, 1653, 1598, 1525, 1472, 1370, 1254, 1112, 750 cm$^{-1}$ NMR(300 MHz,CDCl$_3$, δ ppm): 1.63–1.77(2H,m),2.50–2.64(2H,m), 3.62–4.06(6H,m),3.80(6H,s),3.81 (3H,s),4.56(2H,s),4.60 (2H,s),4.85–4.95(1H, m), 5.68(1H,brs),6.52–6.58(2H,m), 6.64–6.73(2H,m),6.79–6.84(2H,m),7.18–7.40(7H,m) [α]$_D$$^{20}$: –24.0° (c=0.05, MeOH)

EXAMPLE 7

2-((2,6-dimethoxyphenyl)carbonylamino)-3-((2,4,8-triaza-1-oxo-4-phenyl-2-benzylspiro[4.5]dec-8-yl)carbonylamino)propanoic acid (7)

(7)

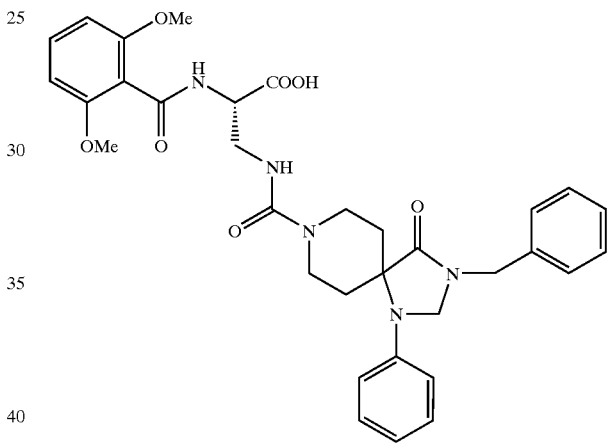

In 1 ml of methanol, 19 mg of methyl 2-((2,6-dimethoxyphenyl)carbonylamino)-3-((2,4,8-triaza-1-oxo-4-phenyl-2-benzylspiro[4.5]dec-8-yl)carbonylamino) propionate was dissolved, and 0.15 ml of 1N aqueous sodium hydroxide solution was added thereto, followed by stirring the resulting mixture at room temperature for 2 hours. To the reaction solution, 0.1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 16.5 mg of 2-((2,6-dimethoxyphenyl)carbonylamino)-3-((2,4,8-triaza-1-oxo-4-phenyl-2-benzylspiro[4.5]dec-8-yl)carbonylamino) propanoic acid (yield: 89%).

LR-MS(m/z): 614(M$^+$–H) IR(KBr): 3397,2931, 1700, 1653, 1599, 1525, 1510, 1473, 1255, 1112, 749 cm$^{-1}$ NMR(300 MHz,CDCl$_3$, δ ppm): 1.67–1.80(2H,m), 2.42–2.65(2H,m),3.40–3.50(1H,m),3.73–4.00(5H,m),3.78 (6H,s),4.44–4.51(1H,m),4.57(2H,s), 4.62(2H,s),5.99(1H, brs),6.53–6.58(2H,m),6.64–6.77(2H,m),6.82–6.88(1H,m), 7.20–7.40(7H,m),7.52–7.59(1H,m) HR-MS: $C_{33}H_{37}N_5O_7$ Calcd.: 614.2615. Found: 614.2587. $[\alpha]_D^{20}$: −5.3° (c=0.04, MeOH)

EXAMPLE 8

Methyl 2-((2,6-difluorophenyl)carbonylamino)-3-((2,4,8-triaza-1-oxo-4-phenyl-2-benzylspiro[4.5]dec-8-yl)carbonylamino)propionate (8)

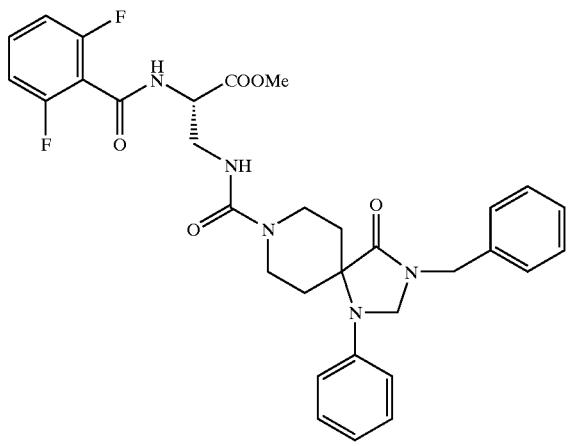

(8)

In 2 ml of dichloromethane, 78 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 1 ml of trifluoroacetic acid was added thereto, followed by stirring the resulting mixture at room temperature for 1 hour. After concentrating the reaction solution, 2 ml of dichloromethane, 98 μl of triethylamine, and 26 μl of 2,6-difluorobenzoyl chloride were added to the residue, and the resulting mixture was stirred at room temperature for 12.5 hours. To the reaction mixture, saturated aqueous sodium hydrogen carbonate solution was added, and the resulting mixture was extracted with chloroform. Organic layers were combined, washed with 0.1N hydrochloric acid and with saturated saline, dried over anhydrous sodium sulfate, and concentrated. The residue was purified by column chromatography (dichloromethane/methanol=50:1) to obtain 24 mg of methyl 2-((2,6-difluorophenyl)carbonylamino)-3-((2,4,8-triaza-1-oxo-4-phenyl-2-benzylspiro[4.5]dec-8-yl)carbonylamino) propionate (yield: 28%).

LR-MS(m/z): 605(M$^+$) IR(KBr): 3064, 3032, 2907, 1748, 1697, 1625, 1601, 1540, 1468, 1371, 1260, 1208, 1161, 1122, 1010, 910, 795 cm$^{-1}$ NMR(300 MHz,CDCl$_3$, δ ppm): 1.64–1.80(2H,m),2.51–2.63(2H,m),3.68–3.98(6H,m), 3.79 (3H,s),4.58(2H,s),4.61 (2H,s),4.79–4.84(1H,m),5.21(1H, brs),6.65–6.72(2H,m),6.78–6.84(1H,m),6.89–6.99(2H,m), 7.20–7.40(7H,m),7.78(1H,m) $[\alpha]_D^{20}$: −18.2° (c=0.11, MeOH)

EXAMPLE 9

2-((2,6-difluorophenyl)carbonylamino)-3-((2,4,8-triaza-1-oxo-4-phenyl-2-benzylspiro[4.5]dec-8-yl) carbonylamino)propanoic acid (9)

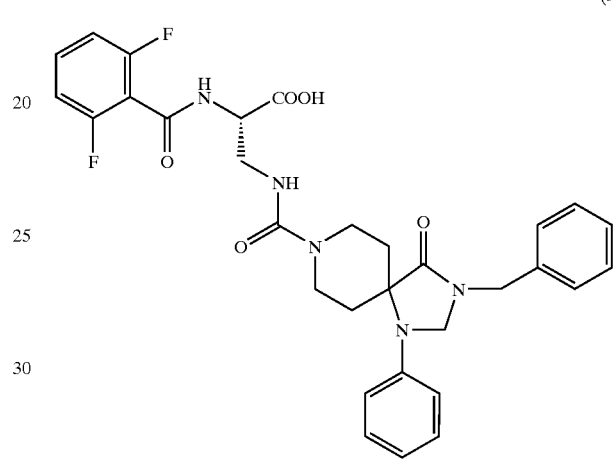

(9)

In 1 ml of methanol, 19 mg of methyl 2-((2,6-difluorophenyl)carbonylamino)-3-((2,4,8-triaza-1-oxo-4-phenyl-2-benzylspiro[4.5]dec-8-yl)carbonylamino) propionate was dissolved, and 0.2 ml of 1N aqueous sodium hydroxide solution was added thereto, followed by stirring the resulting mixture at room temperature for 1 hour. To the reaction solution, 0.1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 15.1 mg of 2-((2,6-difluorophenyl)carbonylamino)-3-((2,4,8-triaza-1-oxo-4-phenyl-2-benzylspiro[4.5]dec-8-yl) carbonylamino)propanoic acid (yield: 82%).

LR-MS(m/z): 590(M$^+$−H) IR(KBr): 3395, 2927, 1674, 1626, 1601, 1539, 1468, 1379, 1262, 1009, 749 cm$^{-1}$ NMR(300 MHz,CD$_3$OD, δ ppm): 1.71–1.82(2H,m), 2.43–2.61 (2H,m),3.43–3.54(1H,m),3.73–4.00(5H,m), 4.45–4.53(1H,m),4.57(2H,s),4.60(2H,s), 5.85(1H,brs), 6.66–6.75(2H,m),6.81–6.89(1H,m),6.90–7.00(2H,m), 7.20–7.42(7H,m),8.02(1H,m) HR-MS: $C_{31}H_{31}F_2N_5O_5$ Calcd.: 590.2215. Found: 590.2209. $[\alpha]_D^{20}$: −73.5 (c=0.02, MeOH)

EXAMPLE 10

Methyl 2-((2-bromo-6-methylphenyl)carbonylamino)-3-((2,4,8-triaza-1-oxo-4-phenyl-2-benzylspiro[4.5]dec-8-yl)carbonylamino)propionate (10)

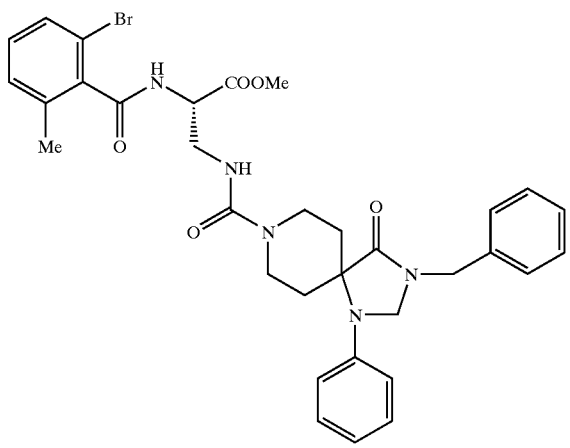

In 2 ml of dichloromethane, 158 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 1 ml of trifluoroacetic acid was added thereto, followed by stirring the resulting mixture at room temperature for 2 hours. After concentrating the reaction solution, the residue was dissolved in 5 ml of dichloromethane, and then 50 mg of BOP, 67 mg of 2-bromo-6-methylbenzoic acid and 195 μl of diisopropylamine were added thereto, followed by stirring the resulting mixture at room temperature under argon atmosphere for 20 hours. To the reaction mixture, 1N hydrochloric acid was added, and the resulting mixture was extracted with chloroform. Organic layers were combined, washed with saturated aqueous sodium hydrogen carbonate solution and with saturated saline, dried over anhydrous sodium sulfate, and concentrated. The residue was purified by column chromatography (dichloromethane/methanol=60:1) to obtain 163 mg of methyl 2-((2-bromo-6-methylphenyl)carbonylamino)-3-((2,4,8-triaza-1-oxo-4-phenyl-2-benzylspiro[4.5]dec-8-yl)carbonylamino)propionate (yield: 88%).

LR-MS(m/z): 661 (M$^+$) IR(KBr): 2926, 1748, 1699, 1655, 1601, 1526, 1450, 1369, 1258, 1206, 1164, 845, 748 cm$^{-1}$ NMR(300 MHz,CDCl$_3$, δ ppm): 1.64–1.77(2H,m), 2.39(3H,s),2.46–2.61 (2H,m),3.65–3.94(6H,m),3.80(3H,s), 4.57(2H,s),4.59(2H,s),4.80–4.90(1H,m),5.24(1H,brs), 6.64–6.73(2H,m),6.80–6.87(1H,m),7.10–7.40(10H,m) [α]$_D^{20}$: −4.95° (c=0.22, MeOH)

EXAMPLE 11

2-((2-bromo-6-methylphenyl)carbonylamino)-3-((2,4,8-triaza-1-oxo-4-phenyl-2-benzylspiro[4.5]dec-8-yl)carbonylamino)propanoic acid (11)

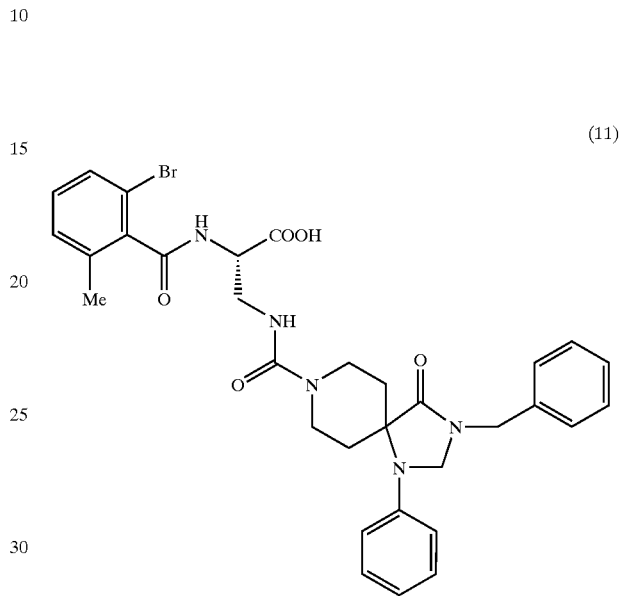

In 4 ml of methanol, 150 mg of methyl 2-((2-bromo-6-methylphenyl)carbonylamino)-3-((2,4,8-triaza-1-oxo-4-phenyl-2-benzylspiro[4.5]dec-8-yl)carbonylamino) propionate was dissolved, and 1.2 ml of 1N aqueous sodium hydroxide solution was added thereto, followed by stirring the resulting mixture at room temperature for 5 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 121.8 mg of 2-((2-bromo-6-methylphenyl)carbonylamino)-3-((2,4,8-triaza-1-oxo-4-phenyl-2-benzylspiro[4.5]dec-8-yl)carbonylamino)propanoic acid (yield: 82%).

LR-MS(m/z): 646(M$^+$−H) IR(KBr): 3395, 2926, 1700, 1654, 1601, 1526, 1452, 1378, 1261, 749 cm$^{-1}$ NMR(300 MHz,CD$_3$OD, δ ppm): 1.62–1.80(2H,m),2.36(3H,s), 2.43–2.62(2H,m),3.53–3.62(1H,m),3.72–4.00(5H,m),4.57 (2H,s),4.60(2H,s),5.99(1H,brs),6.66–6.72(2H,m),6.81–6.90 (1H,m),7.12–7.40(9H,m),7.62–7.70(1H,m) HR-MS: C$_{32}$H$_{34}$BrN$_5$O$_5$ Calcd.: 646.1665. Found: 646.1701. [α]$_D^{20}$: −30.5° (c=0.04, MeOH)

EXAMPLE 12

Methyl 2-((2,6-dimethylphenyl)carbonylamino)-3-((2,4,8-triaza-1-oxo-4-phenyl-2-benzylspiro[4.5]dec-8-yl)carbonylamino)propanoic acid (12)

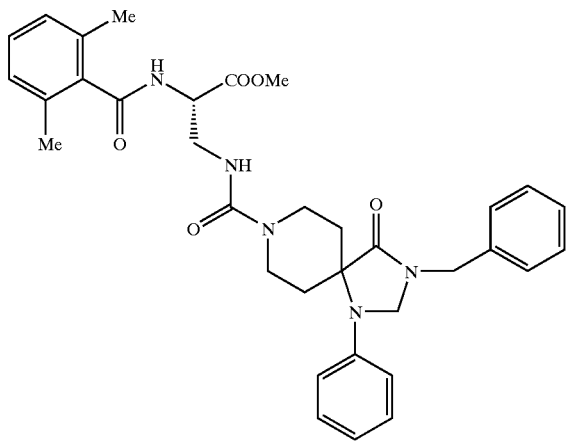

(12)

In 1 ml of dichloromethane, 50 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 0.5 ml of trifluoroacetic acid was added thereto, followed by stirring the resulting mixture at room temperature for 1 hour. After concentrating the reaction solution, the residue was dissolved in 1 ml of dichloromethane, and then 50 mg of BOP, 15 mg of 2,6-dimethylbenzoic acid and 70 μl of diisopropylamine were added thereto, followed by stirring the resulting mixture overnight under argon atmosphere at room temperature. To the reaction mixture, 1N hydrochloric acid was added, and the resulting mixture was extracted with chloroform. Organic layers were combined, washed with saturated aqueous sodium hydrogen carbonate solution and with saturated saline, dried over anhydrous sodium sulfate, and concentrated. The residue was purified by column chromatography (ethyl acetate/n-hexane=2:1) to obtain 45.8 mg of methyl 2-((2,6-dimethylphenyl)carbonylamino)-3-((2,4,8-triaza-1-oxo-4-phenyl-2-benzylspiro[4.5]dec-8-yl)carbonylamino)propanoic acid (yield: 85%).

LR-MS(m/z): 597(M⁺) IR(KBr): 3394,2925,1747,1700, 1635,1527,1469,1378,1260,1207,1161,750 cm$^{-1}$ NMR(300 MHz,CDCl$_3$, δ ppm): 1.62–1.71 (2H,m),2.32(6H,s), 2.40–2.54(2H,m),3.60–3.90(6H,m),3.78(3H,s),4.54(2H,s), 4.58(2H,s),4.76–4.84(2H,m),5.63(1H,brs),6.63–6.70(2H, m),6.80–6.84(1H,m),6.93–7.00(2H,m),7.06–7.17(1H,m), 7.18–7.43(7H,m),7.40(1H,brs) $[\alpha]_D^{20}$: −18.0° (c=0.10, CHCl$_3$)

EXAMPLE 14

2-((2,6-dimethylphenyl)carbonylamino)-3-((2,4,8-triaza-1-oxo-4-phenyl-2-benzylspiro[4.5]dec-8-yl)carbonylamino)propanoic acid (13)

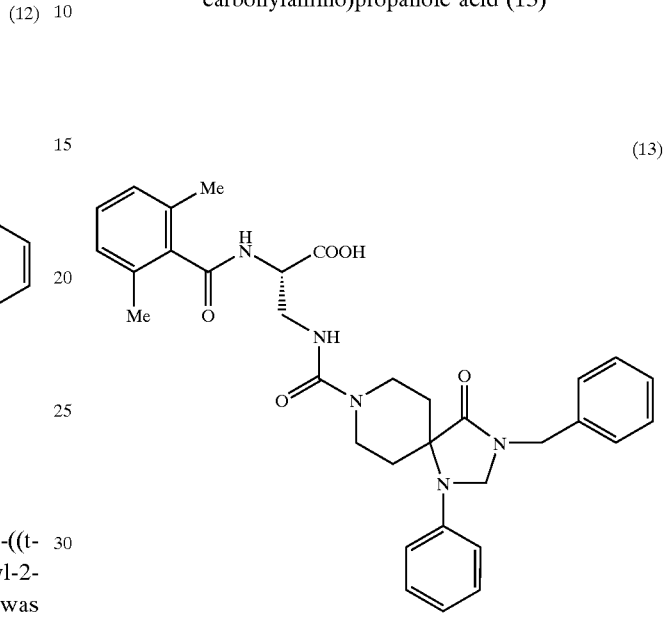

(13)

In 1 ml of methanol, 44 mg of methyl 2-((2,6-dimethylphenyl)carbonylamino)-3-((2,4,8-triaza-1-oxo-4-phenyl-2-benzylspiro[4.5]dec-8-yl)carbonylamino)propionate was dissolved, and 0.4 ml of 1N aqueous sodium hydroxide solution was added thereto, followed by stirring the resulting mixture at room temperature for 2 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 23.1 mg of 2-((2,6-dimethylphenyl)carbonylamino)-3-((2,4,8-triaza-1-oxo-4-phenyl-2-benzylspiro[4.5]dec-8-yl)carbonylamino)propanoic acid (yield: 54%).

LR-MS(m/z): 682(M⁺-H) IR(KBr): 3384,2925,1698, 1637,1601,1534,1468,1381,1262,1203,1163,749 cm−1 NMR(300 MHz,CD$_3$OD, δ ppm): 1.72–1.80(2H,m),2.32 (6H,s),2.43–2.62(2H,m),3.42–3.51 (2H,m),3.75–4.02(4H, m),4.50–4.53(1H,m),4.56(2H,s),4.61 (2H,s), 5.83(1H,brs), 6.68–6.71(2H,m),6.83–6.90(1H,m),7.01–7.05(2H,m), 7.18–7.40(8H,m),7.88(1H,brs) HR-MS: C$_{33}$H$_{36}$N$_5$O$_5$ Calcd.: 582.2716. Found: 582.2698. $[\alpha]^{20}_D$: −31.5° (c=0.0, CHCl$_3$)

EXAMPLE 14

Methyl 2-(adamantan-2-ylcarbonylamino)-3-((2,4,8-triaza-1-oxo-4-phenyl-2-benzylspiro[4.5]dec-8-yl)carbonylamino)propionate (14)

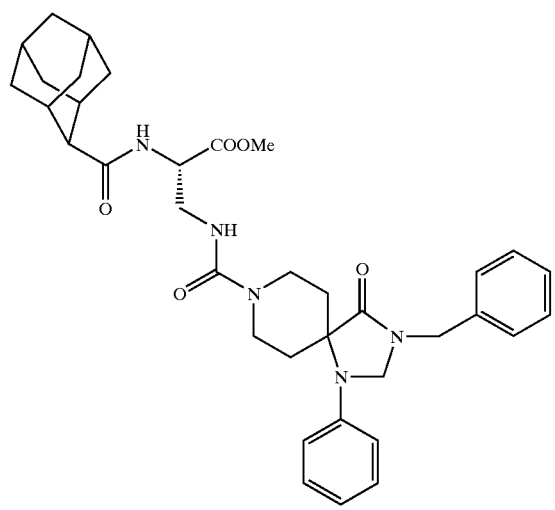

In 1 ml of dichloromethane, 45 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 0.5 ml of trifluoroacetic acid was added thereto, followed by stirring the resulting mixture at room temperature for 2 hours. After concentrating the reaction solution, the residue was dissolved in 2 ml of dichloromethane, and then 45 μl of triethylamine and 25 mg of adamantan-2-carbonyl chloride were added thereto, followed by stirring the resulting mixture overnight at room temperature. To the reaction mixture, saturated aqueous sodium hydrogen carbonate solution was added, and the resulting mixture was extracted with chloroform. Organic layers were combined, washed with water and with saturated saline, dried over anhydrous sodium sulfate, and concentrated. The residue was purified by column chromatography (ethyl acetate/n-hexane=1:1) to obtain 33 mg of methyl 2-(adamantan-2-ylcarbonylamino)-3-((2,4,8-triaza-1-oxo-4-phenyl-2-benzylspiro[4.5]dec-8-yl)carbonylamino)propionate (yield: 65%).

LR-MS(m/z): 627(M$^+$) IR(KBr): 3423,2908,2851,1739,1702,1638,1526,1453,1370,1260,1203,1151,748 cm$^{-1}$ NMR(300 MHz,CDCl$_3$, δ ppm): 1.61–1.78(8H,m),1.80–1.84(6H,m),1.97–2.05(3H,m),2.46–2.60(2H,m),3.51–3.98(6H,m),3.77(3H,s),4.52–4.60(2H,m),4.55(2H,s),4.61(2H,s),5.33(1H,brs),6.64–6.68(2H,m),6.80–6.84(1H,m),7.20–7.40(7H,m) $[\alpha]^{20}_D$: −13.0° (c=0.10,CHCl$_3$)

EXAMPLE 15

2-(adamantan-2-ylcarbonylamino)-3-((2,4,8-triaza-1-oxo-4-phenyl-2-benzylspiro[4.5]dec-8-yl)carbonylamino)propanoic acid (15)

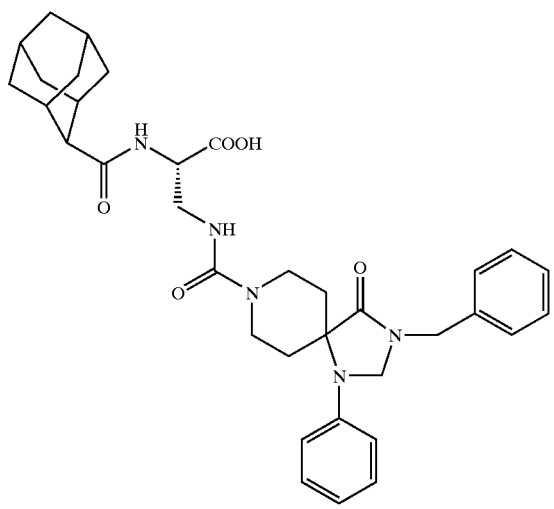

In 2 ml of methanol, 32.1 mg of methyl 2-(adamantan-2-ylcarbonylamino)-3-((2,4,8-triaza-1-oxo-4-phenyl-2-benzylspiro[4.5]dec-8-yl)carbonylamino)propionate was dissolved, and 0.3 ml of 1N aqueous sodium hydroxide solution was added thereto, followed by stirring the resulting mixture at room temperature for 1.5 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 13.9 mg of 2-(adamantan-2-ylcarbonylamino)-3-((2,4,8-triaza-1-oxo-4-phenyl-2-benzylspiro[4.5]dec-8-yl)carbonylamino)propanoic acid (yield: 44%).

LR-MS(m/z): 612(M$^+$−H) IR(KBr): 3423,2907,2851,1701,1637,1526,1451,1365,1261,746 cm$^{-1}$ NMR(300 MHz,CDCl$_3$, δ ppm): 1.60–1.81(8H,m),1.82–1.89(6H,m),2.02–2.09(3H,m),2.40–2.62(2H,m),3.40–3.44(2H,m),3.72–4.02(4H,m),4.23–4.28(1H,m),4.56(2H,s),4.61(2H,s),5.64(1H,brs),6.65–6.70(2H,m),6.82–6.87(1H,m),7.19–7.40(7H,m),8.47(1H,brs) HR-MS: C$_{35}$H$_{42}$N$_5$O$_5$ Calcd.: 612.3186. Found: 612.3190. $[\alpha]^{20}_D$: −15.0° (c=0.1,MeOH)

EXAMPLE 16

Methyl 2-((2,6-dichlorophenyl)carbonylamino)-3-((2,4,8-triaza-2-methyl-1-oxo-4-phenylspiro[4.5]dec-8-yl)carbonylamino)propionate (16)

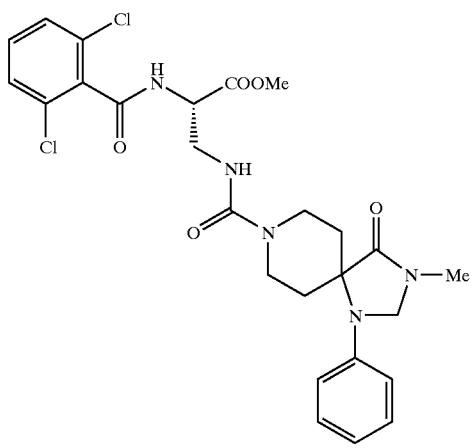

(16)

In 10 ml of dichloromethane, 103 mg of methyl 3-amino-2-((2,6-dichlorophenyl)carbonylamino)propionate was dissolved, and 52.9 mg of saturated sodium hydrogen carbonate and 84.7 mg of chloroformic acid p-nitrophenyl ester were added thereto under argon atmosphere, followed by stirring the resulting mixture at room temperature for 1.5 hours. To the reaction mixture, 130 mg of 2,4,8-triaza-2-methyl-4-phenylspiro[4.5]decane-1-one and 123 μl of triethylamine were added, and the resulting mixture was stirred overnight at room temperature. After concentrating the reaction mixture, saturated aqueous sodium hydrogen carbonate solution was added, and the resulting mixture was extracted with chloroform. Organic layers were combined, washed with 1N hydrochloric acid and with saturated saline, dried over anhydrous sodium sulfate, and concentrated. The residue was purified by column chromatography (ethyl acetate/methanol=50:1) to obtain 159.8 mg of methyl 2-((2,6-dichlorophenyl)carbonylamino)-3-((2,4,8-triaza-2-methyl-1-oxo-4-phenylspiro[4.5]dec-8-yl)carbonylamino)propionate (yield: 81%).

LR-MS(m/z): 561 (M+) IR(KBr): 3395, 3278, 2952, 2932, 1742, 1703, 1655, 1616, 1532, 1520, 1432, 1272, 749 cm$^{-1}$ NMR(300 MHz,CDCl$_3$, δ ppm): 1.63–1.72(2H,m), 2.46–2.60(2H,m),3.00(3H,s),3.63–3.92(2H,m),3.82(3H,s), 4.68(2H,s),4.82–4.88(1H,m),5.26(1H,brs),6.73–6.78(2H, m),6.84–6.89(1H,m),7.23–7.34(5H,m),7.40(1H,brs) [α]$_D^{20}$: −15.4° (c=0.10, MeOH)

EXAMPLE 17

2-((2,6-dichlorophenyl)carbonylamino)-3-((2,4,8-triaza-2-methyl-1-oxo-4-phenylspiro[4.5]dec-8-yl)carbonylamino)propanoic acid (17)

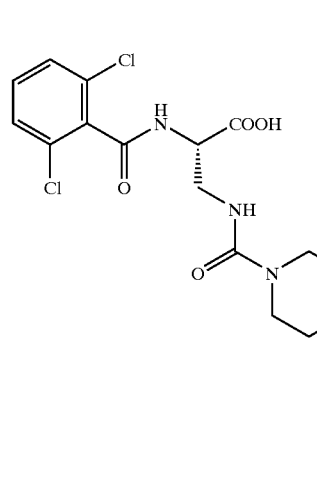

(17)

In 2 ml of methanol, 140 mg of methyl 2-((2,6-dichlorophenyl)carbonylamino)-3-((2,4,8-triaza-2-methyl-1-oxo-4-phenylspiro[4.5]dec-8-yl)carbonylamino)propionate was dissolved, and 0.75 ml of 1N sodium hydroxide solution was added thereto, followed by stirring the resulting mixture overnight at room temperature. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 104 mg of 2-((2,6-dichlorophenyl)carbonylamino)-3-((2,4,8-triaza-2-methyl-1-oxo-4-phenylspiro[4.5]dec-8-yl)carbonylamino)propanoic acid (yield: 76%).

LR-MS(m/z): 546(M+−H) IR(KBr): 3383, 3064, 2930, 1685, 1603, 1533, 1432, 1369, 1265, 1197, 1171, 986, 800, 749 cm$^{-1}$ NMR(300 MHz,CDCl$_3$, δ ppm): 1.68–1.79(2H, m), 2.42–2.63(2H,m), 3.01(3H,s), 3.45–3.59(1H,m), 3.68–4.00(5H,m), 4.53–4.58(1H,m), 4.69(2H,s), 5.98(1H, brs), 6.74–6.78(2H,m), 6.85–6.92(1H,m), 7.24–7.35(5H,m), 7.64(1H,brs) [α]$_D^{20}$: −18.5° (c=0.10, CHCl$_3$)

EXAMPLE 18

Methyl 2-((2,6-dichlorophenyl)carbonylamino)-3-((2,4,8-triaza-2-(2-methylpropyl)-1-oxo-4-phenylspiro[4.5]dec-8-yl)carbonylamino)propionate (18)

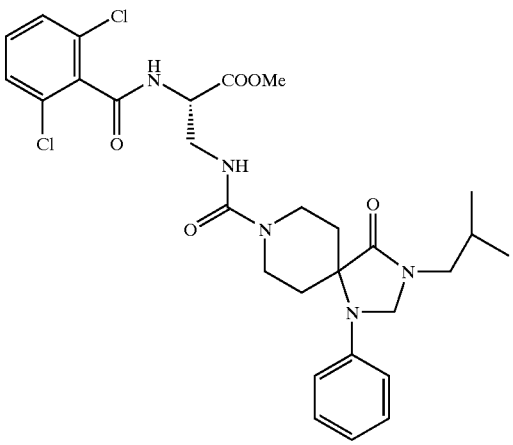

(18)

In 2.7 ml of dichloromethane, 72.2 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 0.3 ml of trifluoroacetic acid was added thereto, followed by stirring the resulting mixture at room temperature for 2 hours. After concentrating the reaction solution, the residue was dissolved in 2.7 ml of dichloromethane, and then 150 μl of triethylamine and 50 μl of 2,6-dichlorobenzoyl chloride were added thereto, followed by stirring the resulting mixture at room temperature for 5 hours. To the reaction mixture, saturated aqueous sodium hydrogen carbonate solution was added, and the resulting mixture was extracted with chloroform. Organic layers were combined, washed with 0.1N hydrochloric acid and with saturated saline, dried over anhydrous sodium sulfate, and concentrated. The residue was purified by column chromatography (chloroform/methanol=50:1) to obtain 58.7 mg of methyl 2-((2,6-dichlorophenyl)carbonylamino)-3-((2,4,8-triaza-2-(2-methylpropyl)-1-oxo-4-phenylspiro[4.5]dec-8-yl)carbonylamino)propionate (yield: 71%).

LR-MS(m/z): 603(M$^+$) IR(KBr): 3383, 3063, 2958, 1747, 1694, 1528, 1469, 1433, 1375, 1259, 1200, 1169, 1128, 965, 800, 782, 749 cm$^{-1}$ NMR(300 MHz,CDCl$_3$, δ ppm): 0.95 (6H,d,J=6.5),1.63–1.74(2H,m),1.95–2.08(1H,m),2.46–2.62 (2H,m),3.23(2H,d,J=7.4),3.63–3.94(6H,m),3.83(3H,s),4.68 (2H,s),4.82–4.88(1H,m),5.24–5.30(1H,m),6.74–6.79(2H, m),6.83–6.88(1H,m),7.23–7.40(6H,m) $[\alpha]_D^{20}$: −82.0° (c=0.10, MeOH)

EXAMPLE 19

2-((2,6-dichlorophenyl)carbonylamino)-3-((2,4,8-triaza-2-(2-methylpropyl)-1-oxo-4-phenylspiro[4.5]dec-8-yl)carbonylamino)propanoic acid (19)

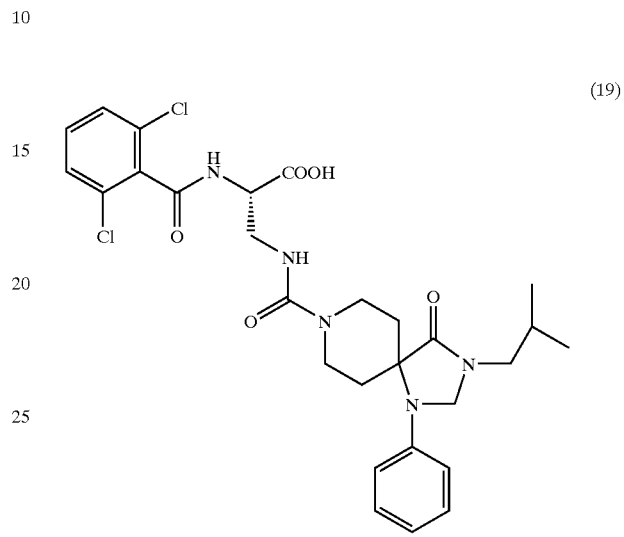

(19)

In 2 ml of methanol, 55.6 mg of methyl 2-((2,6-dichlorophenyl)carbonylamino)-3-((2,4,8-triaza-2-(2-methylpropyl)-1-oxo-4-phenylspiro[4.5]dec-8-yl) carbonylamino)propionate was dissolved, and 1 ml of 1N aqueous sodium hydroxide solution was added thereto, followed by stirring the resulting mixture at room temperature for 1.5 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 28.4 mg of 2-((2,6-dichlorophenyl)carbonylamino)-3-((2,4,8-triaza-2-(2-methylpropyl)-1-oxo-4-phenylspiro[4.5]dec-8-yl) carbonylamino)propanoic acid (yield: 52%).

LR-MS(m/z): 588(M$^+$−H) IR(KBr): 3393, 2960, 2927, 2876, 1740, 1687, 1603, 1531, 1470, 1432, 1378, 1264, 1187, 1170, 967, 801, 749 cm$^{-1}$ NMR(300 MHz,CD$_3$OD, δ ppm): 0.97(6H,d,J=6.6), 1.63–1.72(2H,m), 1.96–2.17(1H, m),2.46–2.60(2H,m),3.25(2H,d,J=7.6),3.53–3.77(4H,m), 3.86–3.98(2H,m),4.75(2H,s),4.80–4.85(2H,m),6.80–6.88 (3H,m),7.22–7.31(2H,m),7.37–7.43(3H,m) $[\alpha]^{20}_D$=−15.5° (c=0.10,MeOH) HR-MS: $C_{12}H_{32}Cl_2N_5O_5$ Calcd.: 588.1812. Found: 588.1812.

EXAMPLE 20

Methyl 2-((2-methyl-5-nitrophenyl)carbonylamino)-3-((2,4,8-triaza-2-(2-methylpropyl)-1-oxo-4-phenylspiro[4.5]dec-8-yl)carbonylamino)propionate (20)

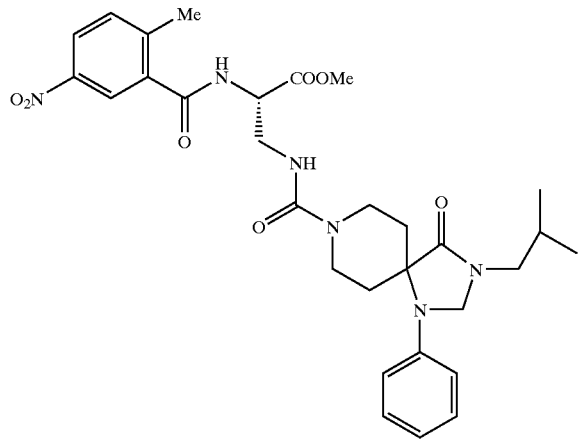

(20)

In 3 ml of dichloromethane, 54 mg of methyl 2-amino-3-((2,4,8-triaza-2-(2-methylpropyl)-1-oxo-4-phenylspiro[4.5]dec-8-yl)carbonylamino)propionate was dissolved, and then 71 mg of BOP, 25 mg of 2-methyl-5-nitrobenzoic acid and 91 µl of diisopropylamine were added, followed by stirring the resulting mixture under argon atmosphere at room temperature for 21 hours. Water was added to the reaction mixture and the resulting mixture was extracted with chloroform. Organic layers were combined, washed with saturated aqueous sodium hydrogen carbonate solution and with saturated saline, dried over anhydrous sodium sulfate, and concentrated. The residue was purified by column chromatography (dichloromethane/methanol=10:1) to obtain 60 mg of methyl 2-((2-methyl-5-nitrophenyl)carbonylamino)-3-((2,4,8-triaza-2-(2-methylpropyl)-1-oxo-4-phenylspiro[4.5]dec-8-yl)carbonylamino)propionate (yield: 78%).

LR-MS(m/z): 594(M$^+$) IR(KBr): 2958, 2871, 1750, 1698, 1657, 1523, 1469, 1438, 1348, 1261, 1206, 1164, 1136, 912, 740 cm$^{-1}$ NMR(300 MHz,CDCl$_3$, δ ppm): 0.96(6H,d,J=6.6), 1.64–1.78(2H,m), 1.92–2.08(1H,m), 2.50–2.61(2H,m), 2.61(3H,s), 3.23(2H,d,J=7.7), 3.65–3.97(6H,m), 3.80(3H,s), 4.69(2H,s), 4.66–4.75(1H,m), 5.18(1H,brs), 6.71–6.77(2H,m), 6.79–6.84(1H,m), 7.20–7.30(2H,m), 7.33–7.40(1H,m), 8.12–8.18(1H,m), 8.37–8.40(1H,m), 8.56(1H,brs) [α]$_D^{20}$: −18.7° (c=0.05, MeOH)

EXAMPLE 21

2-((2-methyl-5-nitrophenyl)carbonylamino)-3-((2,4,8-triaza-2-(2-methylpropyl)-1-oxo-4-phenylspiro[4.5]dec-8-yl)carbonylamino)propanoic acid (21)

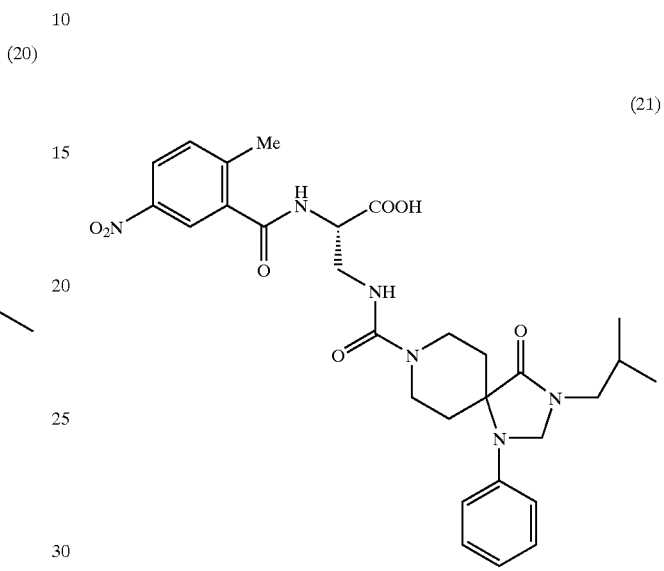

(21)

In 2 ml of methanol, 57 mg of methyl 2-((2-methyl-5-nitrophenyl)carbonylamino)-3-((2,4,8-triaza-2-(2-methylpropyl)-1-oxo-4-phenylspiro[4.5]dec-8-yl)carbonylamino)propionate was dissolved, and 0.5 ml of 1N aqueous sodium hydroxide solution was added thereto, followed by stirring the resulting mixture at room temperature for 1 hour. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 39.5 mg of 2-((2-methyl-5-nitrophenyl)carbonylamino)-3-((2,4,8-triaza-2-(2-methylpropyl)-1-oxo-4-phenylspiro[4.5]dec-8-yl)carbonylamino)propanoic acid (yield: 68%).

LR-MS(m/z): 579(M$^+$−H) IR(KBr): 3383, 2960, 2929, 1689, 1658, 1523, 1471, 1349, 1265, 1166, 835, 745 cm$^{-1}$ NMR(300 MHz,CD$_3$OD, δ ppm): 0.95(6H,d,J=6.6), 1.65–1.80(2H,m), 1.92–2.07(1H,m), 2.43–2.56(2H,m), 2.58(3H,s), 3.23(2H,d,J=7.7), 3.53–3.65(1H,m), 3.66–3.99(5H,m), 4.53–4.60(1H,m), 4.68(2H,s), 5.78(1H,brs), 6.70–6.79(2H,m), 6.80–6.88(1H,m), 7.20–7.30(2H,m), 7.33–7.40(1H,m), 8.13–8.18(1H,m), 8.35–8.38(1H,m), 8.77(1H,brs) HR-MS: C$_{29}$H$_{35}$N$_6$O$_7$ Calcd.: 579.2567. Found: 579.2516. [α]$_D^{20}$: −40.8° (c=0.04, MeOH)

EXAMPLE 22

Methyl 2-((2,6-dichlorophenyl)carbonylamino)-3-((2,4,8-triaza-1-oxo-4-phenyl-2-propylspiro[4.5]dec-8-yl)carbonylamino)propionate (22)

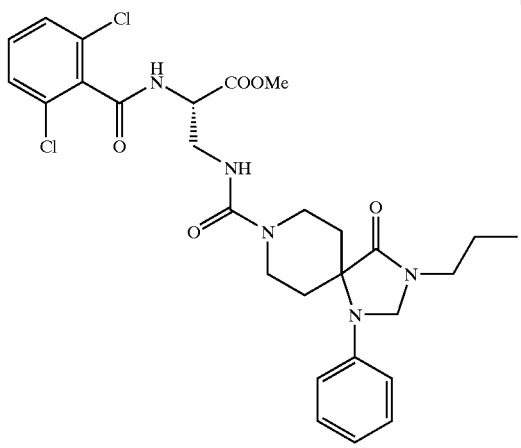

(22)

In 3 ml of acetonitrile and 8 ml of dichloromethane, 166 mg of methyl 3-amino-2-((2,6-dichlorophenyl)carbonylamino) propionate was dissolved, and 69 mg of saturated sodium hydrogen carbonate and 123 mg of chloroformic acid p-nitrophenyl ester were added thereto under argon atmosphere, followed by stirring the resulting mixture at room temperature for 1 hour. To the reaction mixture, 210 mg and 355 μl of triethylamine were added, and the reaction mixture was stirred at room temperature for 13 hours. After concentrating the reaction mixture, saturated aqueous sodium hydrogen carbonate solution was added, and the resulting mixture was extracted with chloroform. Organic layers were combined, washed with 0.1N hydrochloric acid and with saturated saline, dried over anhydrous sodium sulfate and concentrated. The residue was purified by column chromatography (dichloromethane/methanol=60:1) to obtain 232 mg of methyl 2-((2,6-dichlorophenyl)carbonylamino)-3-((2,4,8-triaza-1-oxo-4-phenyl-2-propylspiro[4.5]dec-8-yl)carbonylamino)propionate (yield: 77%).

LR-MS(m/z): 589(M$^+$) IR(KBr): 2962, 2873, 1748, 1688, 1601, 1530, 1471, 1432, 1379, 1258, 1197, 1169, 1127, 989, 801, 781, 748 cm$^{-1}$ NMR(300 MHz,CDCl$_3$, δ ppm): 0.96 (3H,t,J=7.1),1.61–1.72(2H,m),2.45–2.60(2H,m),3.40(2H,t,J=7.1),3.61–3.95(4H,m),3.83(3H,s),4.68(2H,s),4.82–4.88 (1H,m),5.23(1H,brs),6.73–6.79(2H,m),6.82–6.88(1H,m), 7.24–7.35(5H,m),7.39(1H,brs) $[\alpha]_D^{20}$: −11.3° (c=0.27, MeOH)

EXAMPLE 23

2-((2,6-dichlorophenyl)carbonylamino)-3-((2,4,8-triaza-1-oxo-4-phenyl-2-propylspiro[4.5]dec-8-yl)carbonylamino)propanoic acid (23)

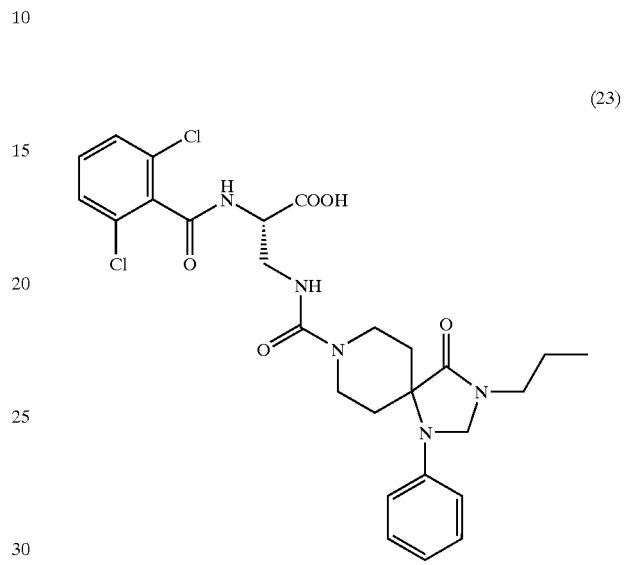

(23)

In 5 ml of methanol, 211 mg of methyl 2-((2,6-dichlorophenyl)carbonylamino)-3-((2,4,8-triaza-1-oxo-4-phenyl-2-propylspiro[4.5]dec-8-yl)carbonylamino) propionate was dissolved, and 2 ml of 1N aqueous sodium hydroxide solution was added thereto, followed by stirring the resulting mixture at room temperature for 1.5 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 166.3 mg of 2-((2,6-dichlorophenyl)carbonylamino)-3-((2,4,8-triaza-1-oxo-4-phenyl-2-propylspiro[4.5]dec-8-yl)carbonylamino)propanoic acid (yield: 77%).

LR-MS(m/z): 574(M$^+$−H) IR(KBr): 3383, 2965, 2932, 2874, 1684, 1601, 1533, 1475, 1432, 1381, 1261, 1197, 1172, 801, 782, 749 cm$^{-1}$ NMR(300 MHz,CDCl$_3$, δ ppm): 0.97(3H,t,J=7.4),1.60–1.76(4H,m),2.43–2.62(2H,m), 3.38–3.43(2H,m),3.60–3.77(3H,m),3.81–3.97(3H,m), 4.63–4.72(1H,m),4.70(2H,s),6.03(1H,brs),6.72–6.80(2H, m),6.82–6.90(1H,m),7.22–7.38(5H,m),7.77(1H,brs) HR-MS: C$_{27}$H$_{30}$Cl$_2$N$_5$O$_5$ Calcd.: 574.1624. Found: 574.1614. $[\alpha]_D^{20}$: −15.5° (c=0.04, MeOH)

EXAMPLE 24

Methyl 3-((2,4,8-triaza-1-oxo-4-phenylspiro[4.5]
dec-8-yl)carbonylamino)-2-((2,4,8-triaza-1-oxo-4-
phenylspiro[4.5]dec-8-yl)carbonylamino)propionate
(24)

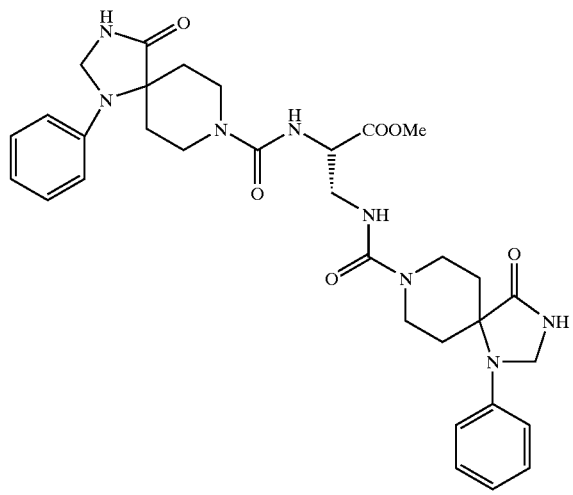

(24)

Under argon atmosphere, 61 mg of methyl 2-amino-3-((2,4,8-triaza-1-oxo-4-phenylspiro[4.5]dec-8-yl)carbonylamino)propionate was dissolved in 2 ml of acetonitrile and 3 ml of dichloromethane, and then 22 mg of saturated sodium hydrogen carbonate and 36 mg of chloroformic acid p-nitrophenyl ester were added thereto while cooling the mixture in ice, followed by stirring the resulting mixture at room temperature for 1.5 hours. To the reaction mixture, 44 mg of 2,4,8-triaza-4-phenylspiro[4.5]decane-1-one and 56 μl of triethylamine were added, and the resulting mixture was stirred overnight at room temperature. After concentrating the reaction mixture, saturated aqueous sodium hydrogen carbonate solution was added, and the resulting mixture was extracted with ethyl acetate. Organic layers were combined, washed with 1N hydrochloric acid and with saturated saline, dried over anhydrous sodium sulfate and concentrated. The residue was purified by column chromatography (dichloromethane/methanol=50:1) to obtain 54 mg of methyl 3-((2,4,8-triaza-1-oxo-4-phenylspiro[4.5]dec-8-yl)carbonylamino)-2-((2,4,8-triaza-1-oxo-4-phenylspiro[4.5]dec-8-yl)carbonylamino)propionate (yield: 53%).

LR-MS(m/z): 632($M^+$) IR(KBr): 2927, 2366, 1705, 1623, 1601, 1501, 1459,1375, 1256, 1187, 965, 910, 750 $cm^{-1}$ NMR(300 MHz,$CDCl_3$, δ ppm): 1.60–1.80(6H,m), 2.43–2.62(4H,m),3.50–4.00(8H,m),3.71(3H,s),4.43–4.51 (1H,m),4.71 (4H,s),5.70–5.80(1H,brs),6.70–6.80(4H,m), 6.72–6.90(2H,m),7.21–7.33(4H,m) $[α]_D^{20}$: −19.5° (c=0.11, MeOH)

EXAMPLE 25

3-((2,4,8-triaza-1-oxo-4-phenylspiro[4.5]dec-8-yl)
carbonylamino)-2-((2,4,8-triaza-1-oxo-4-phenylspiro
[4.5]dec-8-yl)carbonylamino)propanoic acid (25)

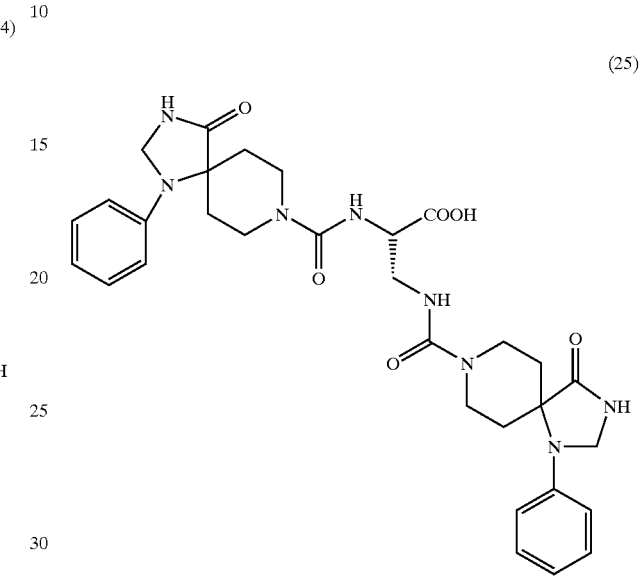

(25)

In 2 ml of methanol, 36 mg of methyl 3-((2,4,8-triaza-1-oxo-4-phenylspiro[4.5]dec-8-yl)carbonylamino)-2-((2,4,8-triaza-1-oxo-4-phenylspiro[4.5]dec-8-yl)carbonylamino) propionate was dissolved, and 0.3 ml of 1N sodium hydroxide solution was added thereto, followed by stirring the resulting mixture at room temperature for 2.5 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 38.7 mg of 3-((2,4,8-triaza-1-oxo-4-phenylspiro [4.5]dec-8-yl)carbonylamino)-2-((2,4,8-triaza-1-oxo-4-phenylspiro[4.5]dec-8-yl)carbonylamino)propanoic acid (yield: 81%).

LR-MS(m/z): 617($M^+$–H) IR(KBr): 3347, 2929, 1708, 1601, 1533, 1501, 1397, 1255, 1189, 966, 751 $cm^{-1}$ NMR (300 MHz,$CD_3OD$, δ ppm): 1.63–1.80(3H,m),2.10–2.40 (4H,m),2.41–2.60(3H,m),3.54–3.75(4H,m),3.76–3.87(2H, m),3.88–4.00(2H,m),4.24–4.35(1H,m),4.73(4H,s), 6.65–6.79(4H,m),6.82–6.92(2H,m),7.20–7.30(4H,m) $[α]_D^{20}$: 26.3° (c=0.04, MeOH) HR-MS: $C_{31}H_{38}N_8O_6$ Calcd.: 617.2836. Found: 617.2834.

EXAMPLE 26

Methyl 2-((4-(2-methylpropanoylamino)-4-phenylpiperidyl)carbonylamino)-3-((2,4,8-triaza-1-oxo-4-phenylspiro[4.5]dec-8-yl)carbonylamino) propionate (26)

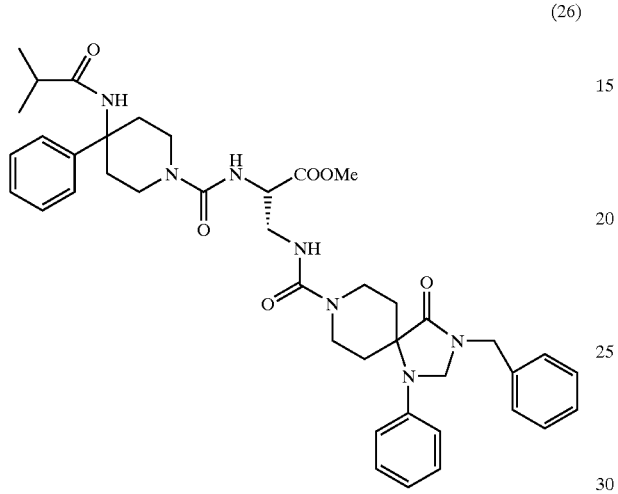

(26)

Under argon atmosphere, 41 mg of methyl 2-amino-3-((2,4,8-triaza-1-oxo-4-phenylspiro[4.5]dec-8-yl)carbonylamino)propionate was dissolved in 2 ml of acetonitrile and 3 ml of dichloromethane, and then 11 mg of saturated sodium hydrogen carbonate and 18 mg of chloroformic acid p-nitrophenyl ester were added thereto while cooling the mixture in ice, followed by stirring the resulting mixture at room temperature for 2.5 hours. To the reaction mixture, 24 mg and 28 μl of triethylamine were added, and the resulting mixture was stirred at room temperature for 16 hours. After concentrating the reaction mixture, saturated aqueous sodium hydrogen carbonate solution was added, and the resulting mixture was extracted with ethyl acetate. Organic layers were combined, washed with 1N hydrochloric acid and with saturated saline, dried over anhydrous sodium sulfate and concentrated. The residue was purified by column chromatography (dichloromethane/methanol= 40:1) to obtain 11 mg of methyl 2-((4-(2-methylpropanoylamino)-4-phenylpiperidyl)carbonylamino)-3-((2,4,8-triaza-1-oxo-4-phenylspiro[4.5]dec-8-yl)carbonylamino)propionate (yield: 19%).

LR-MS(m/z): 647(M$^+$) NMR(300 MHz,CDCl$_3$, δ ppm): 1.04–1.18(6H,m),1.63–1.76(2H,m),1.90–2.04(2H,m), 2.28–2.41(2H,m),2.51–2.64(2H,m),3.02–3.18(2H,m), 3.53–4.00(8H,m), 3.78(3H,s),4.43–4.49(1H,m),4.58(2H,s), 4.61 (2H,s),5.35(1H,brs),5.58(1H,brs)6.64–6.71 (2H,m), 6.78–6.85(1H,m),6.97–7.02(1H,m),7.16–7.40(11H,m)

EXAMPLE 27

2-((4-(2-methylpropanoylamino)-4-phenylpiperidyl) carbonylamino)-3-((2,4,8-triaza-1-oxo-4-phenylspiro [4.5]dec-8-yl)carbonylamino)propanoic acid (27)

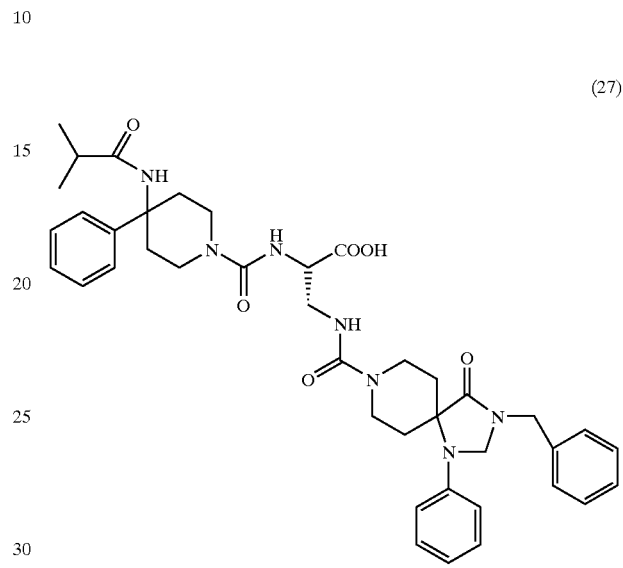

(27)

In 1 ml of methanol, 11 mg of methyl 2-((4-(2-methylpropanoylamino)-4-phenylpiperidyl)carbonylamino)-3-((2,4,8-triaza-1-oxo-4-phenylspiro[4.5] dec-8-yl)carbonylamino)propionate was dissolved, and 0.1 ml of 1N aqueous sodium hydroxide solution was added thereto, followed by stirring the resulting mixture at room temperature for 2.5 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 6.4 mg of 2-((4-(2-methylpropanoylamino)-4-phenylpiperidyl) carbonylamino)-3-((2,4,8-triaza-1-oxo-4-phenylspiro[4.5] dec-8-yl)carbonylamino)propanoic acid (yield: 59%).

LR-MS(m/z): 722(M$^+$–H) IR(KBr): 3369, 2966, 2929, 1688, 1628, 1603, 1530, 1469, 1381, 1262, 1207, 751 cm$^{-1}$ NMR(300 MHz,CDCl$_3$, δ ppm): 1.10–1.20(6H,m), 1.62–1.80(2H,m),1.93–2.10(2H,m),2.32–2.63(5H,m), 3.10–3.30(2H,m),3.55–4.00(8H,m),4.21–4.24(1H,m),4.58 (2H,s),4.60(2H,s),5.52(1H,brs),5.61 (1H,brs),6.61–6.70 (2H,m),6.81–6.88(1H,m),7.20–740(12H,m),8.09(1H,brs) [α]$_D^{20}$: –5.00° (c=0.02, MeOH) HR-MS: C$_{40}$H$_{49}$N$_7$O$_6$ Calcd.: 722.3666. Found: 722.3726.

EXAMPLE 28

Methyl 2-((4-(2-oxo(3-hydrobenzimidazolyl))piperidyl)carbonylamino)-3-(2,4,8-triaza-1-oxo-4-phenylspiro[4.5]dec-8-yl)carbonylamino)propionate (28)

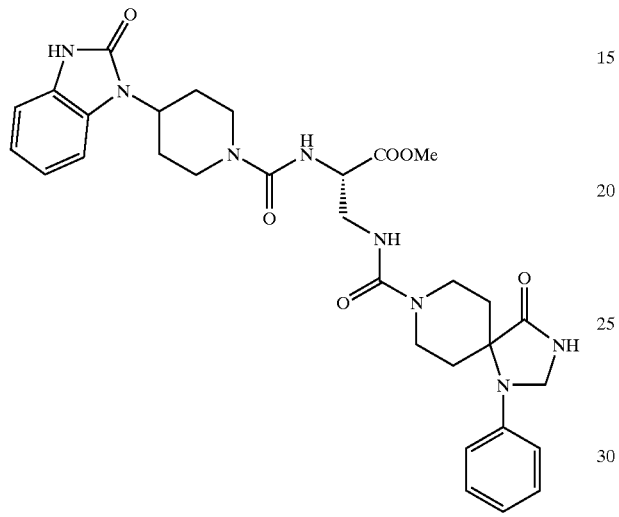

(28)

Under argon atmosphere, 100.3 mg of methyl 3-amino-2-((4-(2-oxo(3-hydrobenzimidazolyl))piperidyl)carbonylamino)propionate was dissolved in 15 ml of dichloromethane, and 42 mg of saturated sodium hydrogen carbonate and 67 mg of chloroformic acid p-nitrophenyl ester were added thereto, followed by stirring the resulting mixture at room temperature for 2 hours. To the reaction mixture, 97 mg and 100 μl of triethylamine were added, and the resulting mixture was stirred overnight at room temperature. After concentrating the reaction mixture, saturated aqueous sodium hydrogen carbonate solution was added, and the resulting mixture was extracted with ethyl acetate. Organic layers were combined, washed with 1N hydrochloric acid and with saturated saline, dried over anhydrous sodium sulfate and concentrated. The residue was purified by column chromatography (dichloromethane/methanol=10:1) to obtain 54.7 mg of methyl 2-((4-(2-oxo(3-hydrobenzimidazolyl))piperidyl)carbonylamino)-3-(2,4,8-triaza-1-oxo-4-phenylspiro[4.5]dec-8-yl)carbonylamino)propionate (yield: 32%).

LR-MS(m/z): 618(M$^+$) IR(KBr): 3427, 2927, 1704, 1624, 1540, 1381, 1254, 1158, 1087, 753 cm$^{-1}$ NMR(300 MHz, CDCl$_3$, δ ppm): 1.65–1.85(4H,m),2.23–2.40(2H,m), 2.49–2.63(2H,m),2.83–2.98(2H,m),3.47–3.51 (1H,m), 3.60–3.98(5H,m),3.78(3H,s),4.17–4.28(2H,m),4.38–4.52 (2H,m),4.75(2H,s),5.40(1H,brs),6.70–6.78(2H,m), 6.84–6.92(1H,m),6.97–7.09(4H,m),7.24–7.35(2H,m),8.75 (1H,brs) $[\alpha]_D^{20}$: −6.85° (c=0.10, MeOH)

EXAMPLE 29

2-((4-(2-oxo(3-hydrobenzimidazolyl))piperidyl)carbonylamino)-3-(2,4,8-triaza-1-oxo-4-phenylspiro[4.5]dec-8-yl)carbonylamino)propanoic acid (29)

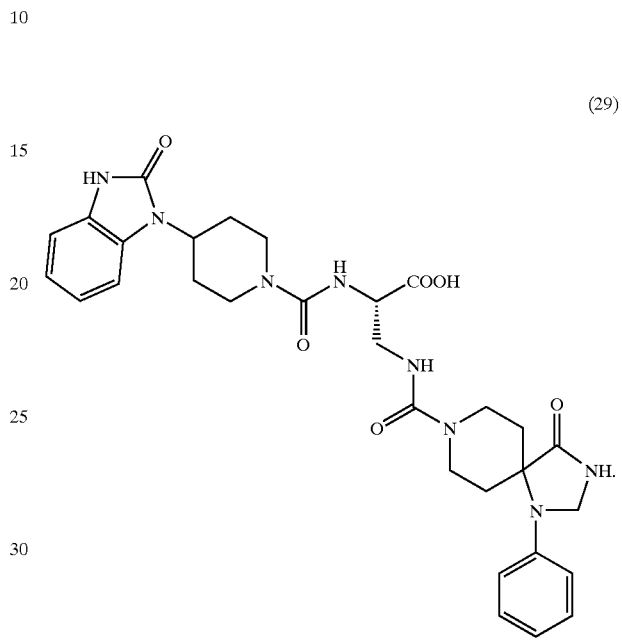

(29)

In 2 ml of methanol, 48 mg of methyl 2-((4-(2-oxo(3-hydrobenzimidazolyl))piperidyl)carbonylamino)-3-(2,4,8-triaza-1-oxo-4-phenylspiro[4.5]dec-8-yl)carbonylamino) propionate was dissolved, and 0.3 ml of 1N sodium hydroxide solution was added thereto, followed by stirring the resulting mixture overnight at room temperature. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 24.8 mg of 2-((4-(2-oxo(3-hydrobenzimidazolyl))piperidyl)carbonylamino)-3-(2,4,8-triaza-1-oxo-4-phenylspiro[4.5]dec-8-yl)carbonylamino)propanoic acid (yield: 53%).

LR-MS(m/z): 603(M$^+$−H) IR(KBr): 3383, 2932, 1702, 1622, 1604, 1541, 1488, 1379, 1254, 1192, 1162, 1091, 966, 754 cm$^{-1}$ NMR(300 MHz,CD$_3$OD, δ ppm): 1.60–1.78(4H, m),2.20–2.40(2H,m),2.50–2.62(2H,m),2.86–3.00(2H,m), 3.50–3.57(4H,m),3.86–4.00(2H,m),4.17–4.30(2H,m), 4.31–4.37(1H,m),4.40–4.52(1H,m),4.73(2H,s),6.75–6.83 (3H,m), 6.92–7.05(4H,m),7.21–7.30(2H,m) $[\alpha]_D^{20}$: −14.70 (c=0.01, MeOH)

EXAMPLE 30

Methyl 2-((4-(2-oxo(3-hydrobenzimidazolyl))
piperidyl)carbonylamino)-3-((2,4,8-triaza-1-oxo-4-
phenyl-2-benzylspiro[4.5]dec-8-yl)carbonylamino)
propionate (30)

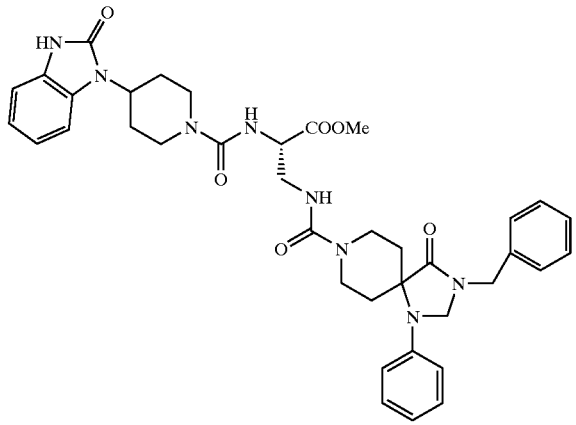

(30)

Under argon atmosphere, 45.1 mg of methyl 2-amino-3-((2,4,8-triaza-1-oxo-4-phenyl-2-benzylspiro[4.5]dec-8-yl)carbonylamino)propionate was dissolved in 2 ml of dichloromethane, and then 11.1 mg of saturated sodium hydrogen carbonate and 21.3 mg of chloroformic acid p-nitrophenyl ester were added thereto while cooling the mixture in ice, followed by stirring the resulting mixture at room temperature for 2.5 hours. To the reaction mixture, 28.7 mg of 1-(4-piperidyl)-3-hydrobenzimidazol-2-one and 65 μl of triethylamine were added, and the resulting mixture was stirred at room temperature for 8 hours. After concentrating the reaction mixture, saturated aqueous sodium hydrogen carbonate solution was added, and the resulting mixture was extracted with ethyl acetate. Organic layers were combined, washed with 1N hydrochloric acid and with saturated saline, dried over anhydrous sodium sulfate and concentrated. The residue was purified by column chromatography (dichloromethane/methanol=20:1) to obtain 38.7 mg of methyl 2-((4-(2-oxo(3-hydrobenzimidazolyl))piperidyl)carbonylamino)-3-((2,4,8-triaza-1-oxo-4-phenyl-2-benzylspiro[4.5]dec-8-yl)carbonylamino)propionate (yield: 60%).

LR-MS(m/z): 708($M^+$) IR(KBr): 3387, 2931, 1689, 1623, 1543, 1484, 1379, 1267, 1204, 1137, 754 $cm^{-1}$ NMR(300 MHz,$CDCl_3$, δ ppm): 1.63–1.85(4H,m),2.22–2.38(2H,m), 2.52–2.66(2H,m),2.83–2.99(2H,m),3.60–3.88(4H,m),3.77 (3H,s),3.91–4.00(1H,m),4.15–4.30(2H,m),4.40–4.53(2H, m),4.57(2H,s),4.61 (2H,s),5.30–5.38(1H,m),6.63–6.72(2H, m),6.80–6.86(1H,m),6.90–7.08(6H,m),7.21–7.40(5H,m), 8.57(1H,brs) $[\alpha]_D^{20}$: −124.0° (c=0.10, MeOH)

EXAMPLE 31

2-((4-(2-oxo(3-hydrobenzimidazolyl))piperidyl)
carbonylamino)-3-((2,4,8-triaza-1-oxo-4-phenyl-2-
benzylspiro[4.5]dec-8-yl)carbonylamino)propanoic
acid (31)

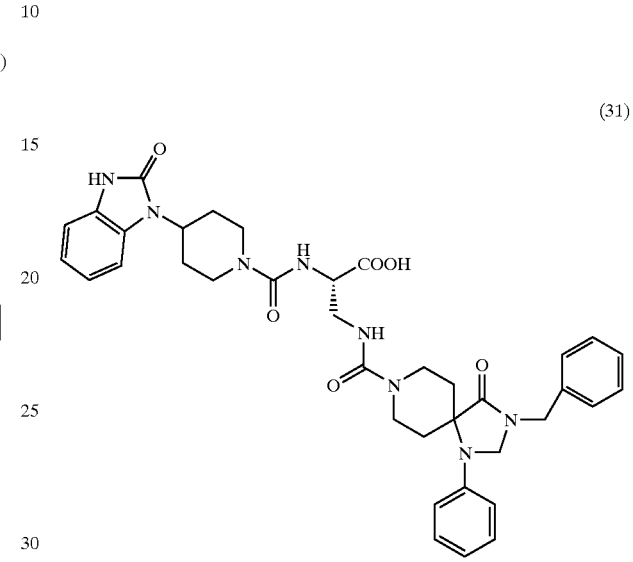

(31)

In 1.5 ml of methanol, 36.6 mg of methyl 2-((4-(2-oxo (3-hydrobenzimidazolyl))piperidyl)carbonylamino)-3-((2,4, 8-triaza-1-oxo-4-phenyl-2-benzylspiro[4.5]dec-8-yl) carbonylamino)propionate was dissolved, and 1 ml of 1N aqueous sodium hydroxide solution was added thereto, followed by stirring the resulting mixture at room temperature for 2.5 hours. To the reaction solution, 1N hydrochloric acid was added, and the resulting mixture was extracted with ethyl acetate. Organic phases were combined, washed with saturated saline, dried over anhydrous sodium sulfate, and concentrated. The residue was reprecipitated from chloroform/n-hexane to obtain 33.2 mg of 2-((4-(2-oxo(3-hydrobenzimidazolyl))piperidyl)carbonylamino)-3-((2,4,8-triaza-1-oxo-4-phenyl-2-benzylspiro[4.5]dec-8-yl) carbonylamino)propanoic acid (yield: 92%).

LR-MS(m/z): 695($M^+$+H) IR(KBr): 3368, 2927, 2862, 1697, 1631, 1535, 1485, 1370, 1263, 1196, 1157, 1086, 1011, 970, 751 $cm^{-1}$ NMR(300 MHz,$CD_3OD$, δ ppm): 1.60–1.80(4H,m),2.20–2.40(2H,m),2.50–2.61 (2H,m), 2.89–3.01(2H,m),3.60–3.75(4H,m),3.91–4.02(2H,m), 4.16–4.30(2H,m),4.30–4.55(2H,m),4.60(2H,s),4.62(2H,s), 6.62–6.82(3H,m),6.87–7.07(4H,m),7.20–7.40(7H,m) HR-MS: $C_{37}H_{43}N_8O_6$ Calcd.: 695.3306. Found: 695.3339. $[\alpha]_D^{20}$: −12.0° (c=0.10,MeOH)

EXAMPLE 32

Methyl 2-((4-(2-oxo(3-hydrobenzimidazolyl))piperidyl)carbonylamino)-3-((2,4,8-triaza-2-(2-methylpropyl)-1-oxo-4-phenylspiro[4.5]dec-8-yl)carbonylamino)propionate (32)

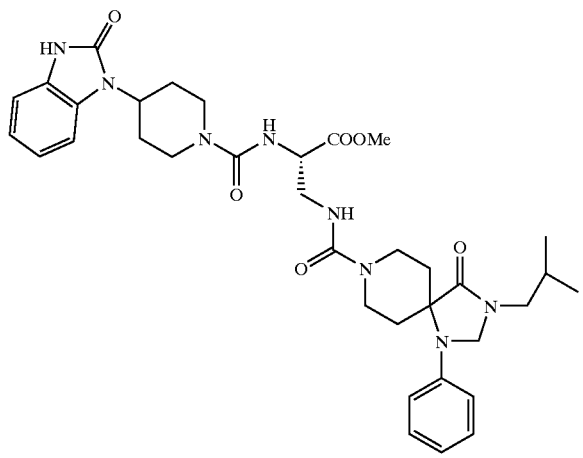

(32)

In 2.7 ml of dichloromethane, 173.1 mg of methyl 2-((t-butoxy)carbonylamino)-3-((2,4,8-triaza-2-(2-methylpropyl)-1-oxo-4-phenylspiro[4.5]dec-8-yl)carbonylamino)propionate was dissolved, and 0.3 ml of trifluoroacetic acid was added thereto. The resulting mixture was stirred at room temperature for 2 hours, and then concentrated. Under argon atmosphere, the residue was dissolved in 2.4 ml of acetonitrile, and then 15.4 mg of saturated sodium hydrogen carbonate and 29.5 mg of chloroformic acid p-nitrophenyl ester were added thereto, followed by stirring the resulting mixture at room temperature for 4 hours. To the reaction mixture, 39.8 mg of 1-(4-piperidyl)-3-hydrobenzimidazol-2-one and 85 μl of triethylamine were added, and the resulting mixture was stirred overnight at room temperature. After concentrating the reaction mixture, saturated aqueous sodium hydrogen carbonate solution was added, and the resulting mixture was extracted with chloroform. Organic layers were combined, washed with 0.1N hydrochloric acid and with saturated saline, dried over anhydrous sodium sulfate and concentrated. The residue was purified by column chromatography (chloroform/methanol=30:1) to obtain 55.6 mg of methyl 2-((4-(2-oxo(3-hydrobenzimidazolyl))piperidyl)carbonylamino)-3-((2,4,8-triaza-2-(2-methylpropyl)-1-oxo-4-phenylspiro[4.5]dec-8-yl)carbonylamino)propionate (yield: 59%)

LR-MS(m/z): 674(M$^+$) IR(KBr): 3363, 2957, 2869, 1697, 1629, 1536, 1483, 1371, 1265, 1200, 1153, 1087, 1011, 966, 752 cm$^{-1}$ NMR(300 MHz,CDCl$_3$, δ ppm): 0.95(6H,d,J=6.6),1.60–1.75(2H,m),1.78–1.85(2H,m),1.96–2.08(1H,m),2.22–2.38(2H,m),2.53–2.64(2H,m),2.84–3.00(2H,m),3.23 (2H,d,J=7.4),3.60–4.00(6H,m),3.77(3H,s),4.17–4.30(2H,m),4.40–4.55(2H,m),4.70(2H,s),5.26–5.34(1H,m),6.72–6.77(2H,m),6.83–6.90(1H,m),6.98–7.10(5H,m),7.24–7.33(2H,m),8.39(1H,brs) $[α]^{20}_D$: -6.5° (c=0.10, MeOH)

EXAMPLE 33

2-((4-(2-oxo(3-hydrobenzimidazolyl))piperidyl)carbonylamino)-3-((2,4,8-triaza-2-(2-methylpropyl)-1-oxo-4-phenylspiro[4.5]dec-8-yl)carbonylamino)propanoic acid (33)

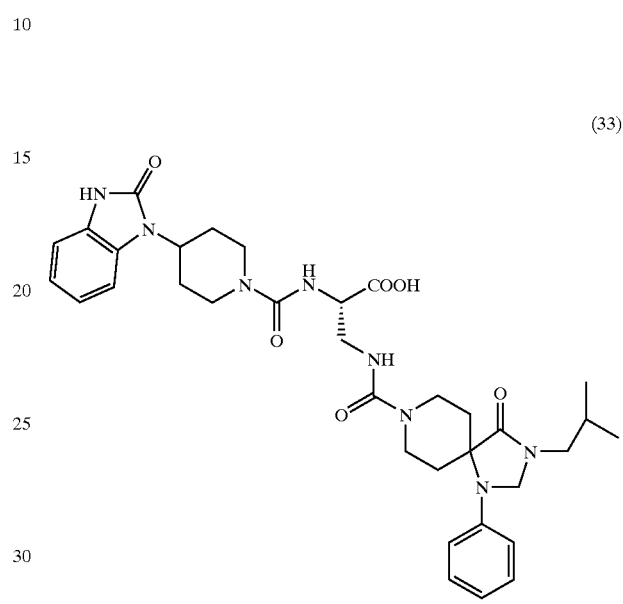

(33)

In 1 ml of methanol, 53.2 mg of methyl 2-((4-(2-oxo(3-hydrobenzimidazolyl))piperidyl)carbonylamino)-3-((2,4,8-triaza-2-(2-methylpropyl)-1-oxo-4-phenylspiro[4.5]dec-8-yl)carbonylamino)propionate was dissolved, and 1 ml of 1N aqueous sodium hydroxide solution was added thereto, followed by stirring the resulting mixture at room temperature for 2 hours. To the reaction solution, 1N hydrochloric acid was added, and the resulting mixture was extracted with ethyl acetate. Organic phases were combined, washed with saturated saline, dried over anhydrous sodium sulfate, and concentrated. The residue was reprecipitated from chloroform/n-hexane to obtain 36.6 mg of 2-((4-(2-oxo(3-hydrobenzimidazolyl))piperidyl)carbonylamino)-3-((2,4,8-triaza-2-(2-methylpropyl)-1-oxo-4-phenylspiro[4.5]dec-8-yl)carbonylamino)propanoic acid (yield: 70%).

LR-MS(m/z): 659(M$^+$–H) IR(KBr): 3372, 2959, 2871, 1696, 1634, 1536, 1483, 1376, 1266, 1197, 1163, 1090, 1011, 968, 752 cm$^{-1}$ NMR(300 MHz,CD$_3$OD, δ ppm): 0.95(6H,d,J=6.6),1.59–1.69(2H,m),1.70–1.80(2H,m),1.99–2.17(1H,m),2.22–2.40(2H,m),2.50–2.63(2H,m),2.90–3.03(2H,m),3.24(2H,d,J=7.7),3.58–3.70(4H,m),3.90–4.02(2H,m),4.18–4.31 (2H,m),4.32–4.39(1H,m),4.40–4.53(1H,m),4.76(2H,s),6.80–6.87(3H,m),6.92–7.10 (4H,m),7.24–7.33(2H,m) $[α]^{20}_D$: -10.0° (c=0.10,MeOH) HR-MS: C$_{34}$H$_{45}$N$_8$O$_6$ Calcd.: 661.3462. Found: 661.3450.

EXAMPLE 34

Methyl 2-((2,6-dichlorophenyl)amino)carbonylamino)-3-((2,4,8-triaza-1-oxo-4-phenylspiro[4.5]dec-8-yl)carbonylamino)propionate (34)

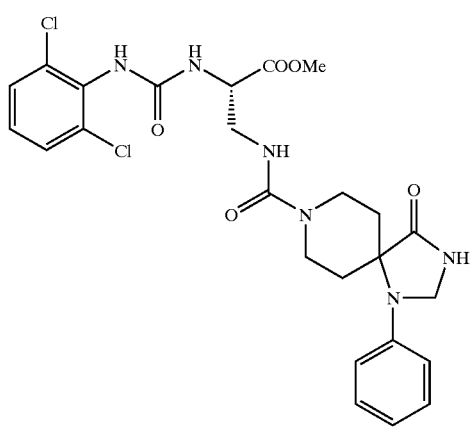

(34)

In 2 ml of dichloromethane, 100 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 1 ml of trifluoroacetic acid was added thereto, followed by stirring the resulting mixture at room temperature for 2 hours. After concentrating the reaction solution, the residue was dissolved in 4 ml of dichloromethane, and then 150 μl of triethylamine and 43 mg of 2,6-dichlorobenzene isocyanate were added, followed by stirring the resulting mixture at room temperature for 3 hours. Saturated aqueous sodium hydrogen carbonate solution was added to the reaction mixture, and the resulting mixture was extracted with chloroform. Organic layers were combined, washed with water and with saturated saline, dried over anhydrous sodium sulfate, and concentrated to obtain 90.7 mg of methyl 2-((2,6-dichlorophenyl)amino)carbonylamino)-3-((2,4,8-triaza-1-oxo-4-phenylspiro[4.5]dec-8-yl)carbonylamino)propionate (yield: 77%).

LR-MS(m/z): 562(M$^+$) IR(KBr): 3371,2925,2852,1708,1624,1539,1457,1438,1372,1254,1078,782,750 cm$^{-1}$ NMR (300 MHz,CDCl$_3$, δ ppm): 1.68–1.81(2H,m),2.43–2.57(2H,m),3.58–3.87(6H,m),3.75(3H,s),4.52–4.60(1H,m),4.75(2H,s),5.26(1H,brs), 6.13(1H,brs),6.25(1H,brs),6.33(1H,brs), 6.72–6.78(2H,m),6.85–6.90(1H.m),7.10–7.20(2H,m), 7.21–7.39(3H,m) [α]$^{20}_D$: –5.5° (c=0.10,CHCl$_3$)

EXAMPLE 35

2-((2,6-dichlorophenyl)amino)carbonylamino)-3-((2,4,8-triaza-1-oxo-4-phenylspiro[4.5]dec-8-yl)carbonylamino)propanoic acid (35)

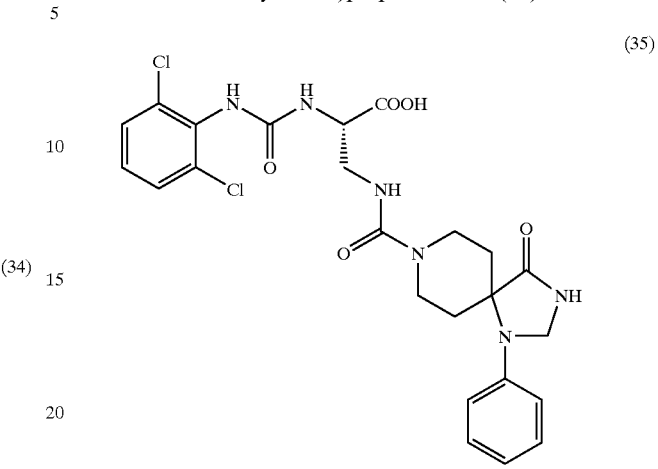

(35)

In 4 ml of methanol, 90 mg of methyl 2-((2,6-dichlorophenyl)amino)carbonylamino)-3-((2,4,8-triaza-1-oxo-4-phenylspiro[4.5]dec-8-yl)carbonylamino)propionate was dissolved, and 1.6 ml of 1N aqueous sodium hydroxide solution was added thereto, followed by stirring the resulting mixture at room temperature for 4 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 21.0 mg of 2-((2,6-dichlorophenyl)amino)carbonylamino)-3-((2,4,8-triaza-1-oxo-4-phenylspiro[4.5]dec-8-yl)carbonylamino) propanoic acid (yield: 52%).

LR-MS(m/z): 547(M$^+$–H) IR(KBr): 3355,2931,1707,1604,1539,1457,1437,1373,1255,1203,1164,1094,965,781 cm$^{-1}$ NMR(300 MHz,CD$_3$OD, δ ppm): 1.62–1.74(2H.m), 2.45–2.60(2H,m),3.55–3.70(4H,m),3.83–3.99(2H,m), 4.42–4.50(1H,m),4.71 (2H,s), 6.78–6.83(3H,m),7.20–7.30 (3H.m),7.38–7.41(2H,m) HR-MS: C$_{24}$H$_{25}$Cl$_2$N$_6$O$_5$ Calcd.: 547.1263. Found: 547.1254. [α]$^{20}_D$: –9.5(c=0.10,MeOH)

EXAMPLE 36

Methyl 2-((2,6-dichlorophenyl)amino)carbonylamino)-3-((2,4,8-triaza-1-oxo-4-phenyl-2-benzylspiro[4.5]dec-8-yl)carbonylamino)propionate (36)

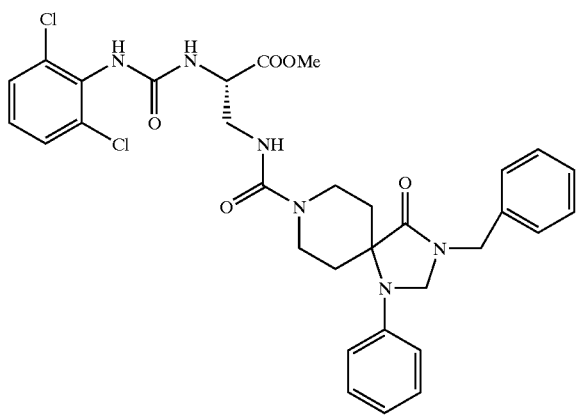

(36)

In 1 ml of dichloromethane, 50 mg of methyl 2-((t-butoxy)carbonylamino)-3-((2,4,8-triaza-1-oxo-4-phenyl-2-benzylspiro[4.5]dec-8-yl)carbonylamino)propionate was dissolved, and 0.5 ml of trifluoroacetic acid was added thereto, followed by stirring the resulting mixture at room temperature for 2 hours. After concentrating the reaction solution, the residue was dissolved in 2 ml of dichloromethane, and then 60 μl of triethylamine and 19 mg of 2,6-dichlorobenzene isocyanate were added, followed by stirring the resulting mixture overnight at room temperature. Saturated aqueous sodium hydrogen carbonate solution was added to the reaction mixture, and the resulting mixture was extracted with chloroform. Organic layers were combined, washed with water and with saturated saline, dried over anhydrous sodium sulfate, and concentrated. The residue was purified by column chromatography (ethyl acetate/n-hexane=1:1) to obtain 46.3 mg of methyl 2-((2,6-dichlorophenyl)amino)carbonylamino)-3-((2,4,8-triaza-1-oxo-4-phenyl-2-benzylspiro[4.5]dec-8-yl)carbonylamino)propionate (yield: 80%).

LR-MS(m/z): 652(M$^+$) IR(KBr): 3392,2925,1740,1701, 1651,1539,1455,1436,1375,1261,1201,1162,1063,75 2 cm−1 NMR(300 MHz,CDCl$_3$, δ ppm): 1.65–1.78(2H,m), 2.45–2.60(2H,m),3.60–3.90(6H,m),3.78(3H,s),4.52–4.61 (1H,m),4.54(2H,s),4.60(2H,s), 5.40(1H,brs), 6.44(1H,brs), 6.63–6.78(3H,m),6.79–6.84(1H,m),7.07–7.12(1H,m), 7.20–7.40(9H,m) [α]$^{20}_D$: −7.0° (c=0.10,CHCl$_3$)

EXAMPLE 37

2-((2,6-dichlorophenyl)amino)carbonylamino)-3-((2,4,8-triaza-1-oxo-4-phenyl-2-benzylspiro[4.5]dec-8-yl)carbonylamino)propanoic acid (37)

(37)

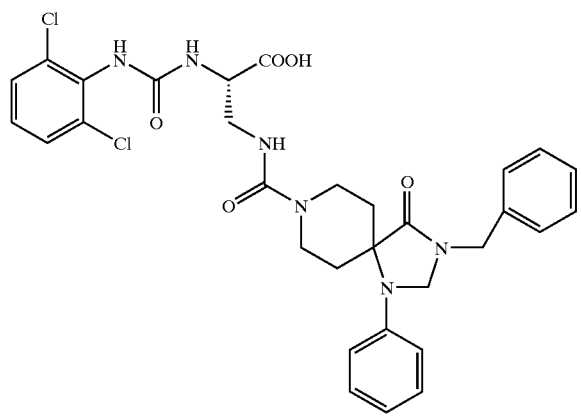

In 2 ml of methanol, 41.2 mg of methyl 2-((2,6-dichlorophenyl)amino)carbonylamino)-3-((2,4,8-triaza-1-oxo-4-phenyl-2-benzylspiro[4.5]dec-8-yl)carbonylamino)propionate was dissolved, and 0.6 ml of 1N aqueous sodium hydroxide solution was added thereto, followed by stirring the resulting mixture at room temperature for 2 hours. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/ether to obtain 21.0 mg of 2-((2,6-dichlorophenyl)amino)carbonylamino)-3-((2,4,8-triaza-1-oxo-4-phenyl-2-benzylspiro[4.5]dec-8-yl)carbonylamino)propanoic acid (yield: 52%).

LR-MS(m/z): 637(M+−H) IR(KBr): 3418,2926,1724, 1700,1624,1539,1472,1377,1265,1194,1075,1025,786,750 cm$^{−1}$ NMR(300 MHz,CDCl$_3$, δ ppm): 1.64–1.78(2H,m), 2.40–2.60(2H,m),3.44–3.55(2H,m),3.63–3.92(4H,m), 4.30–4.40(1H,m),4.54(2H,s),4.60(2H,s), 5.19(1H,brs),5.73 (1H,brs),6.63–6.70(2H,m),6.79–6.89(2H,m),7.10–7.45(9H, m) [α]$^{20}_D$: −6.0° (c=0.10,MeOH)

EXAMPLE 38

2-((2,6-dichlorophenyl)carbonylamino)-4-oxo-4-(2,4,8-triaza-1-oxo-4-phenylspiro[4.5]dec-8-yl)butanoic acid (38)

(38)

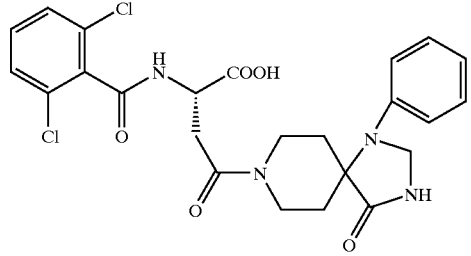

In 2 ml of DMF, 150 mg of methyl 2-amino-4-oxo-4-(2,4,8-triaza-1-oxo-4-phenylspiro[4.5]dec-8-yl)butanoate was dissolved, and 97 μl of 2,6-dichlorobenzoyl chloride and 192 μl of triethylamine were added thereto, followed by stirring the resulting mixture at room temperature for 14 hours. Saturated aqueous sodium hydrogen carbonate solution was added to the reaction mixture, and the resulting mixture was extracted with ethyl acetate. Organic phases were combined, washed with 0.1N hydrochloric acid and with saturated saline, dried over anhydrous sodium sulfate, and concentrated. The residue was dissolved in 6 ml of methanol, and 2 ml of 1N aqueous sodium hydroxide solution was added thereto, followed by stirring the resulting mixture for 1.5 hours. To the reaction solution, 1N hydrochloric acid was added and the resulting mixture was extracted with ethyl acetate. Organic phases were combined, washed with saturated saline, dried over anhydrous sodium sulfate, and concentrated. The residue was purified by column chromatography (DIOL, ethyl acetate/methanol=10/1) to obtain 270 mg of 2-((2,6-dichlorophenyl)carbonylamino)-4-oxo-4-(2,4,8-triaza-1-oxo-4-phenylspiro[4.5]dec-8-yl)butanoic acid (yield: 80%).

LR-MS(m/z): 517(M$^+$−H) IR(KBr): 3408,2926,1709, 1638,1601,1500,1459,1432,1382,1235,1195 cm$^{−1}$ NMR (300 MHz,CDCl$_3$, δ ppm): 2.35–2.65(2H,m),3.00–3.25(2H, m),3.40–3.50(1H,m),3.80–4.00(2H,m),4.30–4.45(1H,m), 4.71(2H,s),5.00–5.07(1H,m),6.80–6.90(3H,m),7.20–7.30 (2H,m),7.50–7.65(3H,m) HR-MS: C$_{24}$H$_{24}$Cl$_2$N$_4$O$_5$ Calcd.: 517.1046. Found: 517.1092. [α]$^{20}_D$: +3.37° (c=0.31,MeOH)

EXAMPLE 39 t-butyl-2-((2,6-dichlorophenyl)carbonylamino)-5-oxo-5-(2,4,8-triaza-1-oxo-4-phenylspiro[4.5]dec-8-yl)pentanoate (39)

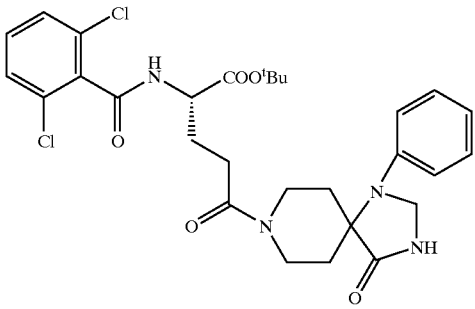

(39)

In 2 ml of DMF, 339 mg of t-butyl 2-amino-5-oxo-5-(2,4,8-triaza-1-oxo-4-phenylspiro[4.5]dec-8-yl)pentanoate was dissolved, and 197 μl of 2,6-dichlorobenzoyl chloride and 385 μl of triethylamine were added thereto, followed by stirring the resulting mixture at room temperature for 3 hours. Saturated aqueous sodium hydrogen carbonate solution was added to the reaction mixture, and the resulting mixture was extracted with ethyl acetate. Organic phases were combined, washed with 0.1N hydrochloric acid and with saturated saline, dried over anhydrous sodium sulfate, and concentrated. The residue was purified by column chromatography (ethyl acetate/n-hexane=6/1) to obtain 468 mg of t-butyl 2-((2,6-dichlorophenyl)carbonylamino)-5-oxo-5-(2,4,8-triaza-1-oxo-4-phenylspiro[4.5]dec-8-yl)pentanoate (yield: 86%).

LR-MS(m/z): 588(M$^+$) IR(KBr): 3259, 3066, 2979, 2932, 1717, 1627, 1502, 1432, 1367, 1299, 1249, 1155, 1088, 1046, 964, 846, 801, 749 cm$^{-1}$ NMR(300 MHz,CDCl$_3$, δ ppm): 1.50(9H,s), 1.70–1.87(2H,m),2.00–2.20(1H,m), 2.30–2.76(5H,m),3.35–3.45(1H,m),3.73–3.98(2H,m), 4.46–4.61(1H,m),4.68–4.82(1H,m),4.76(2H,s),6.60(1H,brs),6.74–6.97(4H,m),7.21–7.33(4H,m) [α]$_D^{20}$: −32.8 (c=0.19, MeOH)

EXAMPLE 40

2-((2,6-dichlorophenyl)carbonylamino)-5-oxo-5-(2,4,8-triaza-1-oxo-4-phenylspiro[4.5]dec-8-yl)pentanoic acid (40)

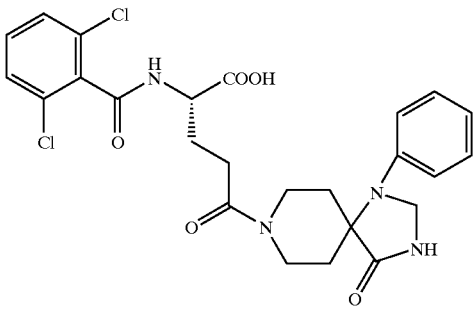

(40)

In 2 ml of dichloromethane, 436 mg of t-butyl 2-((2,6-dichlorophenyl)carbonylamino)-5-oxo-5-(2,4,8-triaza-1-oxo-4-phenylspiro[4.5]dec-8-yl)pentanoic acid was dissolved, and 1.5 ml of trifluoroacetic acid was added thereto, followed by stirring the resulting mixture at room temperature for 4 hours. After concentrating the reaction solution, the residue was reprecipitated from dichloromethane/ether to obtain 295 mg of 2-((2,6-dichlorophenyl)carbonylamino)-5-oxo-5-(2,4,8-triaza-1-oxo-4-phenylspiro[4.5]dec-8-yl)pentanoic acid (yield: 75%).

LR-MS(m/z): 531 (M$^+$−H) IR(KBr): 3258, 3066, 2929, 1716, 1657, 1625, 1601, 1501, 1433, 1381, 1366, 1194, 1089, 801, 751 cm$^{-1}$ NMR(300 MHz,CDCl$_3$, δ ppm): NMR (300 MHz,CDCl$_3$, δ ppm): 1.71–1.85(2H,m),2.00–2.22(1H,m),2.35–2.72(4H,m),2.78–2.83(1H,m),3.40–3.48(1H,m), 3.78–4.00(2H,m),4.43–4.58(1H,m),4.70–4.82(1H,m),4.73 (2H,s),6.72–6.93(3H,m),7.20–7.35(5H,m) HR-MS: C$_{25}$H$_{25}$Cl$_2$N$_4$O$_5$ Calcd.: 531.1202. Found: 531.1218. [α]$_D^{20}$: −53.6° (c=0.04, MeOH)

EXAMPLE 41

Methyl 2-((2,6-dichlorophenyl)carbonylamino)-3-((2,4,8-triaza-1-oxo-4-phenyl-2-prop-2-enylspiro[4.5]dec-8-yl)carbonylamino)propionate (41)

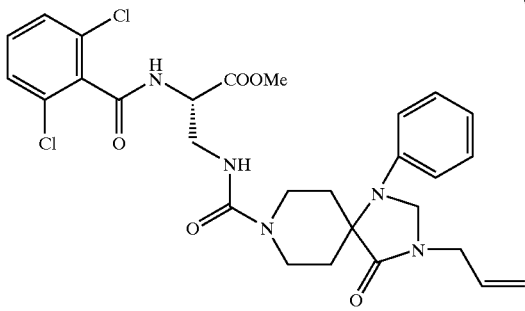

(41)

In 3 ml of dichloromethane and 2 ml of acetonitrile, 67 mg of methyl 3-amino-2-((2,6-dichlorophenyl)carbonylamino)propionate was dissolved, and 31 mg of saturated sodium hydrogen carbonate and 56 mg of chloroformic acid p-nitrophenyl ester were added thereto under argon atmosphere, followed by stirring the resulting mixture at room temperature for 2.5 hours. To the reaction mixture, 95 mg of 2,4,8-triaza-4-phenyl-2-prop-2-enylspiro[4.5]decane-1-one and 167 μl of triethylamine were added, and the resulting mixture was stirred overnight at room temperature. After concentrating the reaction mixture, saturated aqueous sodium hydrogen carbonate solution was added, and the resulting mixture was extracted with chloroform. Organic layers were combined, washed with 0.1N hydrochloric acid and with saturated saline, dried over anhydrous sodium sulfate, and concentrated. The residue was purified by column chromatography (dichloromethane/methanol=60:1) to obtain 89.8 mg of methyl 2-((2,6-dichlorophenyl)carbonylamino)-3-((2,4,8-triaza-1-oxo-4-phenyl-2-prop-2-enylspiro[4.5]dec-8-yl)carbonylamino)propionate (yield: 66%).

LR-MS(m/z): 587(M$^+$) IR(KBr): 3384, 3065, 2927, 1746, 1696, 1602, 1531, 1470, 1432, 1378, 1260, 1198, 1171, 1128, 802, 749 cm$^{-1}$ NMR(300 MHz,CDCl$_3$, δ ppm): 1.63–1.73(2H,m),2.45–2.60(2H,m),3.60–3.92(6H,m), 3.82 (3H,s),4.02–4.07(2H,m),4.65(2H,s),4.80–4.87(1H,m), 5.24–5.32(2H,m), 5.38(1H,brs),5.75–5.86(1H,m),6.73–6.80 (2H,m),6.82–6.90(1H,m),7.22–7.34(5H,m), 7.45(1H,brs) [α]$_D^{20}$: −8.03° (c=0.07, MeOH)

EXAMPLE 42

2-((2,6-dichlorophenyl)carbonylamino)-3-((2,4,8-triaza-1-oxo-4-phenyl-2-prop-2-enylspiro[4.5]dec-8-yl)carbonylamino)propanoic acid (42)

(42)

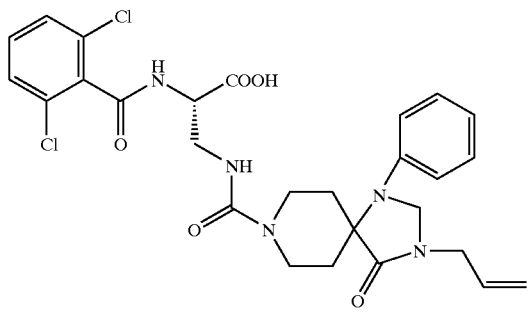

In 3 ml of methanol, 86.3 mg of methyl 2-((2,6-dichlorophenyl)carbonylamino)-3-((2,4,8-triaza-1-oxo-4-phenyl-2-prop-2-enylspiro[4.5]dec-8-yl)carbonylamino) propionate was dissolved, and 0.75 ml of 1N aqueous sodium hydroxide solution was added thereto, followed by stirring the resulting mixture at room temperature for 1 hour. To the reaction solution, 1N hydrochloric acid was added, and the resulting mixture was extracted with chloroform. Organic phases were combined, washed with saturated saline, dried over anhydrous sodium sulfate, and concentrated. The residue was reprecipitated from chloroform/n-hexane to obtain 104 mg of 2-((2,6-dichlorophenyl)carbonylamino)-3-((2,4,8-triaza-1-oxo-4-phenyl-2-prop-2-enylspiro[4.5]dec-8-yl)carbonylamino)propanoic acid (yield: %).

LR-MS(m/z): 572(M$^+$-H) IR(KBr): 3384, 2928, 1686, 1601, 1539, 1473, 1432, 1379, 1262, 1197, 801,749 cm$^{-1}$ NMR(300 MHz,CDCl$_3$, δ ppm): 1.69–1.82(2H,m), 2.44–2.62(2H,m), 3.48–3.57(1H,m), 3.71–4.01(5H,m), 4.02–4.05(2H,m), 4.51–4.58(1H,m), 4.67(2H,s), 5.25–5.36(2H,m), 5.77–5.90(1H,m), 5.95(1H,brs), 6.73–6.81(2H,m), 6.54–6.97(1H,m), 7.23–7.37(5H,m), 7.63(1H,brs) HR-MS: C$_{27}$H$_{29}$Cl$_2$N$_5$O$_5$ Calcd.: 572.1467. Found: 572.1417. [α]$_D^{20}$: −55.8° (c=0.04, MeOH)

EXAMPLE 43

2-(((S)-3-acetylthiazolidin-4-carbonyl)amino)-3-((3-methyl-4-oxo-1-phenyl-1,3,8-triazaspiro[4.5]decane-8-carbonyl)amino)propionic acid methyl ester (43)

(43)

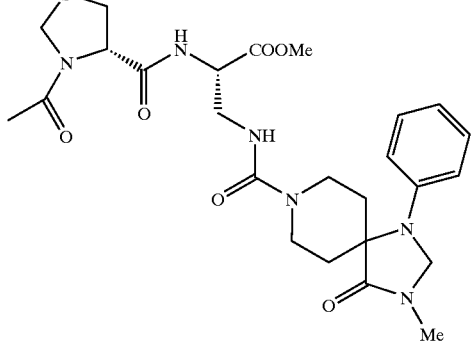

To a solution of 331 mg (0.85 mmol) of 2-amino-3-((3-methyl-4-oxo-1-phenyl-1,3,8-triazaspiro[4.5]decane-8-carbonyl)amino)propionic acid methyl ester in 8.5 ml of dichloromethane, 149 mg (0.85 mmol) of (S)-3-acetylthiazolidin-4-carboxylic acid, 376 mg (0.85 mmol) of BOP reagent and 0.16 ml (0.95 mmol) of N,N-diisopropylethylamine were added, and the resulting mixture was stirred overnight at room temperature. To the reaction mixture, 10 ml of semi-saturated saline was added, and the resulting mixture was extracted with ethyl acetate. Organic phases were combined, washed with 0.5M hydrochloric acid, with saturated aqueous sodium hydrogen carbonate solution and with saturated saline, dried over anhydrous sodium sulfate, and concentrated. The residue was purified by silica gel column chromatography (chloroform:methanol=100:1–10:1) to obtain 305 mg of 2-(((S)-3-acetylthiazolidin-4-carbonyl)amino)-3-((3-methyl-4-oxo-1-phenyl-1,3,8-triazaspiro[4.5]decane-8-carbonyl)amino)propionic acid methyl ester (yield: 65%).

LR-MS (m/z): 547 (M+H)$^+$IR(KBr): 3376, 1750, 1699, 1651, 1639, 1532, 1404, 1268, 1204, 1153, 1128, 1055, 986 cm$^{-1}$ NMR (300 MHz, CDCl$_3$, δ ppm): 8.07 (1H, d, J=6.2), 7.50–7.12 (3H, m), 6.87 (1H, t, J=7.1 Hz), 6.76 (2H, d, J=8.2), 5.15 (1H, t, J=5.5), 5.00 (1H, dd, J=7.0, 2.9), 4.73–4.42 (5H, m), 3.93–3.15 (12H, m), 3.02 (3H, s), 2.66–2.46 (2H, m), 2.17 (3H,s)

EXAMPLE 44

2-(((S)-3-acetylthiazolidine-4-carbonyl)amino)-3-((3-methyl-4-oxo-1-phenyl-1,3,8-triazaspiro[4.5] decane-8-carbonyl)amino)propionic acid (44)

(44)

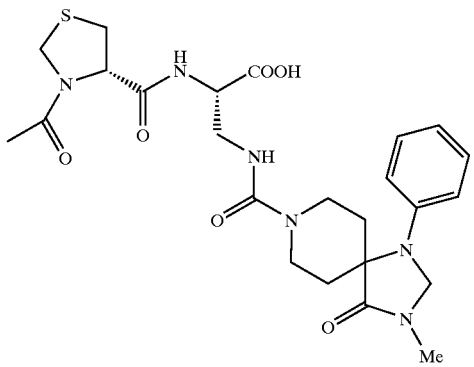

To a solution of 176 mg (0.32 mmol) of 2-(((S)-3-acetylthiazolidin-4-carbonyl)amino)-3-((3-methyl-4-oxo-1-phenyl-1,3,8-triazaspiro[4.5]decane-8-carbonyl)amino) propionic acid methyl ester in 4 ml of tetrahydrofuran, 4 ml of 0.1M aqueous lithium hydroxide solution was added, and the resulting mixture was stirred overnight at room temperature. To the reaction mixture, 0.1M hydrochloric acid was added, and the resulting mixture was extracted with ethyl acetate. Organic phases were combined, washed with saturated saline, dried over anhydrous sodium sulfate, and concentrated. The residue was reprecipitated from ether/chloroform to obtain 130 mg of 2-(3-acetylthiazolidine-4-carbonyl)amino)-3-((3-methyl-4-oxo-1-phenyl-1,3,8-triazaspiro[4.5]decane-8-carbonyl)amino)propionic acid (yield: 76%).

LR-MS (m/z): 533 (M+H)⁺ IR (KBr): 3374, 1689, 1633, 1533, 1407, 1268, 1198, 1155, 1087, 1056, 987 cm⁻¹ NMR (300 MHz, CDCl₃, δppm): 8.79 (1H, d, J=4.7), 7.48–7.13 (2H, m), 6.86 (1H, t, J=7.2), 6.73 (2H, d, J=7.2), 5.81 (1H, t, J6.2), 4.99 (1H, dd, J=6.8, 3.0), 4.68 (2H, s), 4.61 (1H, d, J=8.5), 4.54 (1H, d,J=8.5), 4.27 (1H, m), 3.95–3.54 (6H, m), 3.38–3.16 (2H, m), 3.01 (3H, s), 2.62–2.42 (2H, m), 2.21 (3H, s), 1.69 (2H, d, J=14.6)

EXAMPLE 45

2-(((R)-3-acetylthiazolidin-4-carbonyl)amino)-3-((3-methyl-4-oxo-1-phenyl-1,3,8-triazaspiro[4.5]decane-8-carbonyl)amino)propionic acid methyl ester (45)

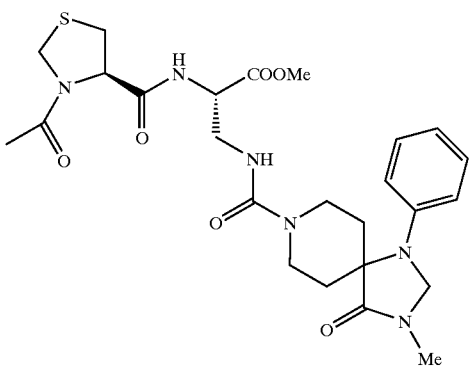

(45)

To a solution of 301 mg (0.77 mmol) of 2-amino-3-((3-methyl-4-oxo-1-phenyl-1,3,8-triazaspiro[4.5]decane-8-carbonyl)amino)propionic acid methyl ester in 7.5 ml of dichloromethane, 135 mg (0.77 mmol) of (R)-3-acetylthiazolidin-4-carboxylic acid, 342 mg (0.77 mmol) of BOP reagent and 0.15 ml (0.86 mmol) of N,N-diisopropylethylamine were added, and the resulting mixture was stirred overnight at room temperature. To the reaction mixture, 10 ml of semi-saturated saline was added, and the resulting mixture was extracted with ethyl acetate. Organic phases were combined, washed with 0.5M hydrochloric acid, with saturated aqueous sodium hydrogen carbonate solution and with saturated saline, dried over anhydrous sodium sulfate, and concentrated. The residue was purified by silica gel column chromatography (chloroform:methanol=100:1–10:1) to obtain 309 mg of 2-(((R)-3-acetylthiazolidin-4-carbonyl)amino)-3-((3-methyl-4-oxo-1-phenyl-1,3,8-triazaspiro[4.5]decane-8-carbonyl)amino)propionic acid methyl ester (yield: 73%).

LR-MS (m/z): 547 (M+H)⁺ IR (KBr): 3372, 1749, 1698, 1658, 1634, 1531, 1438, 1404, 1266, 1207, 1153, 1128, 1084, 1055, 986 cm⁻¹ NMR (300 MHz, CDCl₃, δ ppm): 8.98 (0.33H, d, J=5.3), 7.63 (0.67H, d, J=7.0), 7.48–7.13 (3H, m), 6.91–6.72 (3H, m), 5.45 (0.67H, t, J=6.2), 4.98–4.48 (6.33H, m), 4.00–3.32 (11H, m), 3.16 (1H, dd, J=11.5, 6.5 Hz), 3.01 (3H, s), 2.65–2.42 (2H, m), 2.18 (1H, s), 2.15 (2H, s)

EXAMPLE 46

Methyl 2-(((R)-3-acetylthiazolidin-4-carbonyl)amino)-3-((3-methyl-4-oxo-1-phenyl-1,3,8-triazaspiro[4.5]decane-8-carbonyl)amino)propionate (46)

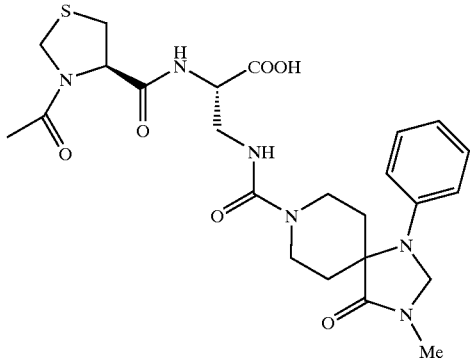

(46)

To a solution of 171 mg (0.31 mmol) of 2-(3-acetylthiazolidin-4-carbonyl)amino)-3-((3-methyl-4-oxo-1-phenyl-1,3,8-triazaspiro[4.5]decane-8-carbonyl)amino) propionic acid methyl ester in 4 ml of tetrahydrofuran, 4 ml of 0.1M aqueous lithium hydroxide solution was added, and the resulting mixture was stirred overnight at room temperature. To the reaction mixture, 0.1M hydrochloric acid was added, and the resulting mixture was extracted with ethyl acetate. Organic phases were combined, washed with saturated saline, dried over anhydrous sodium sulfate, and concentrated. The residue was reprecipitated from ether/chloroform to obtain 135 mg of 2-(3-acetylthiazolidin-4-carbonyl)amino)-3-((3-methyl-4-oxo-1-phenyl-1,3,8-triazaspiro[4.5]decane-8-carbonyl)amino)propionic acid (yield: 81%).

LR-MS (m/z): 533 (M+H)⁺ IR (KBr): 3367, 1693, 1633, 1532, 1408, 1267, 1204, 1154, 1124, 1056, 986 cm⁻¹ NMR (300 MHz, CDCl₃, δppm): 9.17 (0.25H, d, J=5.0), 8.38 (0.75H, d, J=5.0), 7.48–7.13 (2H, m), 6.87 (1H, t, J=7.3), 6.74 (2H, d, J=8.2), 5.82 (1H, m), 4.92–4.33 (6H, m), 3.88–3.54 (6H, m), 3.31 (1H, dd, J=11.9, 4.0), 3.20 (1H, dd, J=11.9, 6.9), 3.01 (3H, s), 2.62–2.42 (2H, m), 2.17 (3H, s), 1.68 (2H, d, J=13.2)

EXAMPLE 47

2-benzyloxycarbonylamino-3-((3-methyl-4-oxo-1-phenyl-1,3,8,-triazaspiro[4.5]decane-8-carbonyl)amino)propionic acid methyl ester (47)

(47)

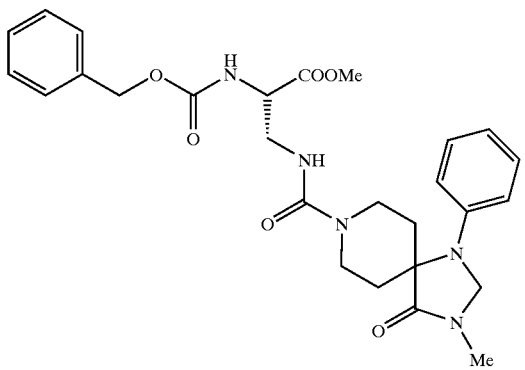

To a solution of 288 mg (0.74 mmol) of 2-amino-3-((3-methyl-4-oxo-1-phenyl-1,3,8-triazaspiro[4.5]decane-8-carbonyl)amino)propionic acid methyl ester in 4 ml of dichloromethane, 0.21 ml (1.48 mmol) of triethylamine and 0.1 ml (0.89 mmol) of benzyloxycarbonyl chloride were added, and the resulting mixture was stirred at room temperature for one day. To the reaction mixture, saturated aqueous sodium hydrogen carbonate solution was added, and the resulting mixture was extracted with chloroform. Organic phases were combined, washed with 10% aqueous citric acid solution and with saturated saline, dried over anhydrous sodium sulfate, and concentrated. The residue was purified by silica gel column chromatography (chloroform:methanol=60:1) to obtain 284 mg of 2-benzyloxycarbonylamino-3-((3-methyl-4-oxo-1-phenyl-1,3,8,-triazaspiro[4.5]decane-8-carbonyl)amino)propionic acid methyl ester (yield: 73%)

LR-MS (m/z): 524 (M+H)+NMR (300 MHz, CDCl$_3$, δ ppm): 7.40–7.22 (7H, m), 6.94 (1H, d, J=6.9), 6.74 (2H, d, J=8.2), 6.31 (1H, br d, J=6.6), 5.10 (1H, br s), 5.09 (2H, s), 3.92–3.57 (9H, m), 3.01 (3H, s), 2.62–2.48 (2H, m), 1.66 (2H, d, J=13.5)

EXAMPLE 48

2-benzyloxycarbonylamino-3-((3-methyl-4-oxo-1-phenyl-1,3,8,-triazaspiro[4.5]decane-8-carbonyl)amino)propionic acid (48)

(48)

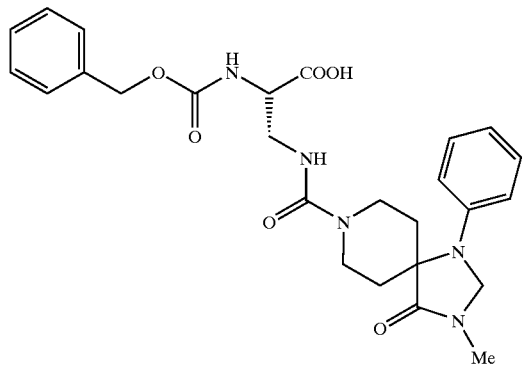

To a solution of 177 mg (0.34 mmol) of 2-benzyloxycarbonylamino-3-((3-methyl-4-oxo-1-phenyl-1,3,8,-triazaspiro[4.5]decane-8-carbonyl)amino)propionic acid methyl ester in 4 ml of tetrahydrofuran, 4 ml of 0.1M aqueous lithium hydroxide solution was added, and the resulting mixture was stirred overnight at 0° C. To the reaction mixture, 0.1M hydrochloric acid was added, and the resulting mixture was extracted with ethyl acetate. Organic phases were combined, washed with saturated saline, dried over anhydrous sodium sulfate, and concentrated. The residue was reprecipitated from ether/chloroform to obtain 143 mg of 2-benzyloxycarbonylamino-3-((3-methyl-4-oxo-1-phenyl-1,3,8,-triazaspiro[4.5]decane-8-carbonyl)amino)propionic acid (yield: 83%).

LR-MS (m/z): 510 (M+H)+NMR (300 MHz, CDCl$_3$, δppm): 7.38–7.20 (7H, m), 6.86 (1H, t, J=7.4), 6.73 (2H, d, J=8.2), 6.54 (1H, d, J=5.0), 5.66 (1H, br s), 5.09 (2H, s), 4.66 (2H, s), 4.24 (1H, br s), 3.90–3.60 (5H, m), 3.45 (1H, br d, J=12.3), 3.00 (3H, s), 2.60–2.40 (2H, m), 1.76–1.56 (2H, m)

EXAMPLE 49

2-(2,6-dichlorobenzylamino)-3-((3-methyl-4-oxo-1-phenyl-1,3,8-triazaspiro[4.5]decane-8-carbonyl)amino)propionic acid methyl ester (49)

(49)

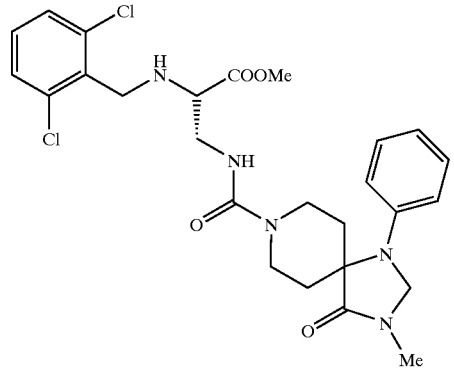

To a solution of 288 mg (0.74 mmol) of 2-amino-3-((3-methyl-4-oxo-1-phenyl-1,3,8-triazaspiro[4.5]decane-8-carbonyl)amino)propionic acid methyl ester in 4 ml of dichloromethane, 0.21 ml (1.48 mmol) of triethylamine and 214 mg (0.89 mmol) of 2,6-dichlorobenzyl bromide were added, and the resulting mixture was stirred at room temperature for one day. To the reaction mixture, saturated aqueous sodium hydrogen carbonate solution was added, and the resulting mixture was extracted with chloroform. Organic phases were combined, washed with saturated saline, dried over anhydrous sodium sulfate, and concentrated. The residue was purified by silica gel column chromatography (chloroform:methanol=60:1) to obtain 195 mg of 2-(2,6-dichlorobenzylamino)-3-((3-methyl-4-oxo-1-phenyl-1,3,8-triazaspiro[4.5]decane-8-carbonyl)amino)propionic acid methyl ester (yield: 48%).

LR-MS (m/z): 548 (M+H)+NMR (300 MHz, CDCl$_3$, δppm): 7.31–7.23 (4H, m), 7.11 (1H, dd, J=8.8, 7.3), 6.85 (1H, t, J=7.5 Hz), 6.73 (2H, d, J=7.9), 5.28 (1H, dd, J=6.1, 3.8), 4.68 (2H, s), 4.17 (1H, d, J=12.6), 3.99 (1H, d, J=12.6), 3.94–3.58 (5H, m), 3.72 (3H, s), 3.48 (1H, dd, J=7.6, 4.4), 3.26 (1H, ddd, J=13.2, 7.9, 3.8), 3.01 (3H, s), 2.60–2.46 (2H, m), 1.65 (2H, d, J=13.8)

EXAMPLE 50

2-(2,6-dichlorobenzylamino)-3-((3-methyl-4-oxo-1-phenyl-1,3,8-triazaspiro[4.5]decane-8-carbonyl)amino)propionic acid (50)

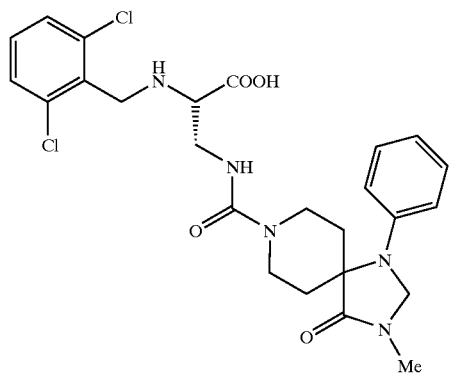
(50)

To a solution of 132 mg (0.24 mmol) of 2-(2,6-dichlorobenzylamino)-3-((3-methyl-4-oxo-1-phenyl-1,3,8-triazaspiro[4.5]decane-8-carbonyl)amino)propionic acid methyl ester in 3 ml of tetrahydrofuran, 2.6 ml of 0.1M aqueous lithium hydroxide solution was added, and the resulting mixture was stirred overnight at room temperature. To the reaction mixture, 0.1M hydrochloric acid was added, and the resulting mixture was extracted with chloroform. Organic phases were combined, washed with saturated saline, dried over anhydrous sodium sulfate, and concentrated. The residue was reprecipitated from ether/chloroform to obtain 103 mg of 2-(2,6-dichlorobenzylamino)-3-((3-methyl-4-oxo-1-phenyl-1,3,8-triazaspiro[4.5]decane-8-carbonyl)amino)propionic acid (yield: 81%).

LR-MS (m/z): 534 (M+H)$^+$NMR (300 MHz, CDCl$_3$, δppm): 7.40–7.24 (5H, m), 6.85 (1H, t, J=7.3), 6.73 (2H, d, J=7.9), 6.71 (1H, br s), 4.65 (2H, s), 4.47 (1H, d, J=13.5), 4.41 (1H, d, J=13.5), 4.01–3.56 (7H, m), 3.00 (3H, s), 2.56–2.40 (2H, m), 1.67 (2H, d, J=14.9)

EXAMPLE 51

Inhibitory Effect by Compounds Against Binding between CS-1 Peptide and VLA-4-IgG Chimera Protein In accordance with the teaching of a report (Humphrise, M. J. et al. J.Bio.Chem.,262,6886–6892(1987)), a conjugate between a peptide (Gys Leu His Gly Pro Glu Glu Ile Leu Asp Val Pro Ser Thr) containing CS-1 sequence and rabbit IgG (Sigma) was prepared. This was diluted with phosphate buffer (hereinafter referred to as "PBS(-)" for short), and the obtained solution was placed in the wells of a 96-well immunoplate (NUNC) in an amount of 100 μl/well, followed by leaving to stand the immunoplate at 4° C. for 16 hours to immobilize the conjugate.

The wells were then washed twice with PBS(-), and 1% BSA solution in PBS, which BSA was heated at 80° C. for 10 minutes, was placed in each well in an amount of 300 μl/well. The immunoplate was left to stand at 4° C. for 3 hours, and then the solution in each well was removed by suction.

Each compound and VLA-4-IgG chimera protein (100 μl) were preliminarily reacted at room temperature for 20 minutes, and then the resulting mixture was allowed to react with the CS-1peptide in each well at 30° C. for 3 hours. Thereafter, non-bound VLA-4-IgG chimera protein was removed by suction, and each well was washed twice with 0.1% BSA-containing TBS buffer (150 mM NaCl, 25 mM Tris-HCl, 1 mM MnCl$_2$, PH7.4). To the bound VLA-4-IgG chimera protein, biotin-labelled anti-human IgG antibody (Vector) as a primary antibody was added, and then avidin-labelled horse radish peroxidase (Sigma) as a secondary antibody was added, thereby allowing the reactions. Then o-phenylenediamine as a substrate was added to color the reaction solution, and the absorbance at 490 nm was measured. From this absorbance, the binding inhibitory activity of each compound was determined. The inhibitory activities of the representative compounds are shown in Table 1.

TABLE 1

| Compound No. | Inhibitory Activity (IC$_{50}$: nM) |
|---|---|
| 3 | 6.1 |
| 7 | 18 |
| 13 | 2.9 |
| 27 | 2.1 |
| 31 | 0.98 |

Industrial Field

The novel spiro derivatives according to the present invention have activities to inhibit cell adhesion via adhesion molecules, especially adhesion molecule VLA-4. Since the spiro acid derivatives according to the present invention are excellent in the effect of inhibiting cell adhesion via adhesion molecules, they are useful as therapeutic drugs against various inflammatory diseases.

What is claimed is:
1. A spiro derivative represented by the Formula I:

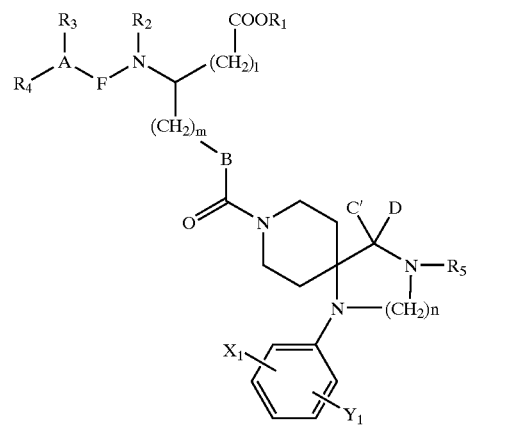
I (wherein 1 and m independently represent integers of 0 to 2; n represents; A represents an oxygen atom, —CH—, carbon having a double bond or a nitrogen atom (with the proviso that when A is an oxygen atom, R$_3$ does not exist); B represents —CH$_2$— or —NH—; C' and D represent hydrogen, or C' and D cooperatively represent O; X$_1$ and Y$_1$ independently represent hydrogen, halogen, C$_1$–C$_8$ alkyl, C$_1$–C$_8$ alkoxy, cyano, nitro, hydroxyl, amino or tetrazole; R$_1$ and R$_2$ independently represent hydrogen or C$_1$–C$_6$ linear alkyl; R$_3$ and R$_4$ independently represent hydrogen, C$_1$–C$_6$ linear alkyl, C$_3$–C$_8$ branched alkyl, or phenyl or benzyl, this phenyl or benzyl being substituted with 0 to 2 substituents selected from the group consisting of halogen, C$_1$–C$_8$ alkyl, $C_1$–$C_8$ alkoxy, cyano, nitro, hydroxyl, amino and tetrazole; F represents —$CH_2$— or —C(O)—;

when A is a nitrogen atom, $R_3$, A and R4 may cooperatively represent (i) Formula II:

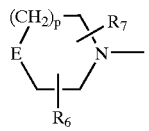

II (wherein p represents an integer of 0 to 4; E represents a carbon atom or a nitrogen atom; $R_6$ and $R_7$ independently represent hydrogen, $C_1$–$C_6$ linear alkyl, $C_3$–$C_8$ branched alkyl, $C_1$–$C_6$ linear acyl, $C_3$–$C_8$ branched acyl, pyrrolidinecarbonyl, piperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, $C_1$–$C_8$ alkyl, $C_1$–$C_8$ alkoxy, cyano, nitro, hydroxyl, amino and tetrazole, or Formula III:

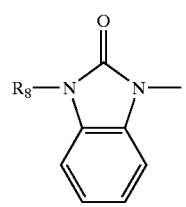

III (wherein $R_8$ represents hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, halogen, $C_1$–$C_8$ alkyl, $C_1$–$C_8$ alkoxy, cyano, nitro, hydroxyl, amino and tetrazole), (ii) Formula IV:

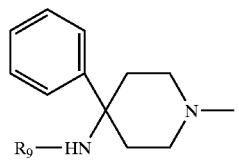

IV (wherein $R_9$ represents $C_1$–$C_6$ linear alkyl, $C_3$–$C_8$ branched alkyl, $C_1$–$C_6$ linear acyl, $C_3$–$C_8$ branched acyl, $C_5$–$C_7$ cycloalkylcarbonyl, $C_1$–$C_6$ linear alkylsulfonyl, $C_3$–$C_8$ branched alkylsulfonyl, or benzoyl, phenylsulfonyl or benzyl, this benzoyl, phenylsulfonyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole)

(iii) Formula V:

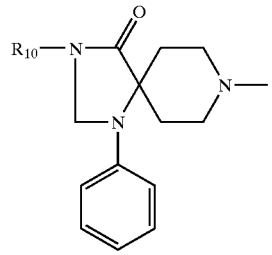

V (wherein $R_{10}$ represents hydrogen, $C_1$–$C_6$ linear alkyl, $C_3$–$C_8$ branched alkyl, $C_6$–$C_{10}$ alkylcycloalkyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole);

When A is —CH— or carbon having a double bond, $R_3$, A and $R_4$ may cooperatively form adamantyl, or Formula VI:

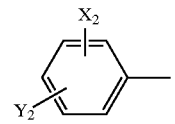

VI (wherein definitions of $X_2$ and $Y_2$ are the same as those of $X_1$ and $Y_1$, respectively)

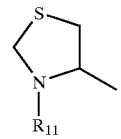

VII or Formula VII:
(wherein definition of $R_{11}$ is the same as that of $R_9$);
$R_5$ represents hydrogen, $C_1$–$C_6$ linear alkyl, $C_3$–$C_8$ branched alkyl, allyl, homoallyl, $C_6$–$C_{10}$ alkylcycloalkyl, or phenyl, benzyl, phenethyl, styryl or naphthylmethyl, this phenyl, benzyl, phenethyl, styryl or naphthylmethyl being substituted with 0 to 2 substituents selected from the group consisting of halogen, $C_1$–$C_8$ alkyl, $C_1$–$C_8$ alkoxy, cyano, nitro, hydroxyl, amino and or a pharmaceutically acceptable salt thereof.

2. The spiro derivative or the pharmaceutically acceptable salt thereof according to claim 1, wherein F represents —C(O)—; A represents —CH—, carbon having a double bond or nitrogen atom, B represents —$CH_2$— or —NH—; C' and D represent hydrogen or C' and D cooperatively represent O; X and Y independently represent hydrogen, halogen, methyl, methoxy, cyano, nitro, hydroxyl, amino or tetrazole; $R_1$ and $R_2$ independently represent hydrogen or $C_1$–$C_6$ linear alkyl; $R_3$ and $R_4$ independently represent hydrogen, $C_1$–$C_6$ linear alkyl or $C_3$–$C_8$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole;

when A is a nitrogen atom, $R_3$, A and $R_4$ may cooperatively represent (i) said Formula II (wherein p represents an integer of 0 to 4; E represents carbon atom or nitrogen atom; $R_6$ and $R_7$ independently represent hydrogen, $C_1$–$C_6$ linear alkyl, $C_3$–$C_8$ branched alkyl, $C_1$–$C_6$ linear acyl, $C_3$–$C_8$ branched acyl, pyrrolidinecarbonyl, piperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, methyl, methoxy, cyano, nitro, hydroxyl, amino and tetrazole, or said Formula III (wherein $R_8$ represents hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole), (ii) said Formula IV (wherein $R_9$ represents $C_1$–$C_6$ linear alkyl, $C_3$–$C_8$ branched alkyl, $C_1$–$C_6$ linear acyl, $C_3$–$C_8$ branched acyl, $C_5$–$C_7$ cycloalkylcarbonyl, $C_1$–$C_6$ linear alkylsulfonyl, $C_3$–$C_8$ branched alkylsulfonyl, or benzoyl, phenylsulfonyl or benzyl, this benzoyl, phenylsulfonyl or benzyl being substituted with 0 to 2 substituents selected from the group consisting of halogen, methyl, methoxy, cyano, nitro, hydroxyl, amino and tetrazole), (iii) said Formula V:

(wherein $R_{10}$ represents hydrogen, $C_1$–$C_6$ linear alkyl, $C_3$–$C_8$ branched alkyl, $C_6$–$C_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole);

when A is —CH— or carbon having a double bond, $R_3$, A and $R_4$ may cooperatively represent adamantyl or said Formula VI (wherein $X_2$ and $Y_2$ represent the same definitions as described above); $R_5$ represents hydrogen, $C_1$–$C_6$ linear alkyl, $C_3$–$C_8$ branched alkyl, allyl, homoallyl, $C_6$–$C_{10}$ alkylcycloalkyl, or phenyl, benzyl, phenethyl, styryl or naphthylmethyl, this phenyl, benzyl, phenethyl, styryl or naphthylmethyl being substituted with 0 to 2 substituents selected from the group consisting of halogen, methyl, methoxy, cyano, nitro, hydroxyl, amino and tetrazole.

3. The spiro derivative or the pharmaceutically acceptable salt thereof according to claim 1 or 2, wherein A represents a nitrogen atom, $R_3$, A and $R_4$ cooperatively represent (i) said Formula II (wherein $R_6$ and $R_7$ independently represent hydrogen, $C_1$–$C_3$ linear alkyl, $C_3$–$C_6$ branched alkyl, $C_1$–$C_3$ linear acyl, $C_3$–$C_6$ branched acyl, pyrrolidinecarbonyl, piperidinecarbonyl, or phenyl, benzoyl, benzyl, indole or N-phenylamide, this phenyl, benzoyl, benzyl, indole or N-phenylamide being substituted with 0 to 2 substituents selected from the group consisting of halogen, methyl, methoxy, cyano, nitro, hydroxyl, amino and tetrazole), or said Formula III (wherein $R_8$ represents hydrogen, $C_1$–$C_3$ linear alkyl, $C_3$–$C_6$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole), (ii) said Formula IV (wherein $R_9$ represents $C_1$–$C_3$ linear alkyl, $C_3$–$C_6$ branched alkyl, $C_1$–$C_3$ linear acyl, $C_3$–$C_6$ branched acyl, $C_5$–$C_7$ cycloalkylcarbonyl, $C_1$–$C_3$ linear alkylsulfonyl, $C_3$–$C_8$ branched alkylsulfonyl, or benzoyl or benzyl, this benzoyl or benzyl being substituted with 0 to 2 substituents selected from the group consisting of halogen, methyl, methoxy, cyano, nitro, hydroxyl, amino and tetrazole), or (iii) said Formula V (wherein $R_{10}$ represents hydrogen, $C_1$–$C_3$ linear alkyl, $C_3$–$C_6$ branched alkyl, $C_6$–$C_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole), the definitions of the symbols other than mentioned above are the same as those described in claim 1 or 2.

4. The spiro derivative or the pharmaceutically acceptable salt thereof according to claim 1 or 2, wherein A represents a nitrogen atom, $R_3$, A and $R_4$ cooperatively represent (i) said Formula II (wherein $R_6$ and $R_7$ independently represent hydrogen, $C_1$–$C_3$ linear acyl, $C_3$–$C_6$ branched acyl, pyrrolidinecarbonyl, piperidinecarbonyl, or phenyl, benzoyl, benzyl, indole or N-phenylamide, this phenyl, benzoyl, benzyl, indole or N-phenylamide being substituted with 0 to 2 substituents selected from the group consisting of halogen, methyl, methoxy, cyano, nitro, hydroxyl, amino and tetrazole), or said Formula III (wherein $R_8$ represents hydrogen, $C_1$–$C_3$ linear alkyl, $C_3$–$C_6$ branched alkyl, or benzyl substituted with 0 to 2 substituents selected from the group consisting of halogen, methyl, methoxy, cyano, nitro, hydroxyl, amino and tetrazole), (ii) said Formula IV (wherein $R_9$ represents $C_1$–$C_3$ linear acyl, $C_3$–$C_6$ branched acyl, $C_5$–$C_7$ cycloalkylcarbonyl, or benzoyl or benzyl, this benzoyl or benzyl being substituted with 0 to 2 substituents selected from the group consisting of halogen, methyl, methoxy, cyano, nitro, hydroxyl, amino and tetrazole), or (iii) said Formula V (wherein $R_{10}$ represents hydrogen, $C_3$–$C_3$ linear alkyl, $C_3$–$C_6$ branched alkyl, $C_6$–$C_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole), the definitions of the symbols other than mentioned above are the same as those described in claim 1 or 2.

5. A pharmaceutical comprising said spiro derivative or a pharmaceutically acceptable salt thereof according to claim 1 or 2 as an effective ingredient and a carrier.

6. A method for inhibiting an VLA-4 adhesion molecule, comprising administering an effective amount of a spiro derivative or a pharmaceutically acceptable salt thereof, wherein the spiro derivative is represented by Formula I:

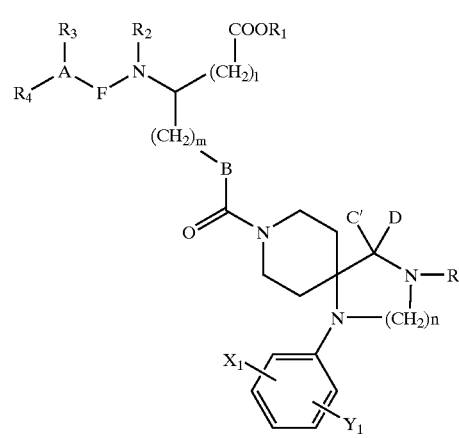

(wherein 1 and m independently represent integers of 0 to 2; n represents an integer of 1 to 3; A represents an oxygen atom, —CH—, carbon having a double bond or a nitrogen atom (with the proviso that when A is an oxygen atom, R3 does not exist); B represents —CH$_2$— or —NH—; C' and D represent hydrogen, or C' and D cooperatively represent O; $X_1$ and $Y_1$ independently represent hydrogen, halogen, $C_1$–$C_8$ alkyl, $C_1$–$C_8$ alkoxy, cyano, nitro, hydroxyl, amino or tetrazole; $R_1$ and $R_2$ independently represent hydrogen or $C_1$–$C_6$ linear alkyl; $R_3$ and $R_4$ independently represent hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole; F represents —CH$_2$— or —C(O)—;

when A is a nitrogen atom, $R_3$, A and $R_4$ may cooperatively represent (i) Formula II:

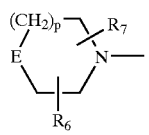

II (wherein p represents an integer of 0 to 4; E represents a carbon atom or a nitrogen atom; $R_6$ and $R_7$ independently represent hydrogen, $C_1$–$C_6$ linear alkyl, $C_3$–$C_8$ branched alkyl, $C_1$–$C_6$ linear acyl, $C_3$–$C_8$ branched acyl, pyrrolidinecarbonyl, piperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, $C_1$–$C_8$ alkyl, $C_1$–$C_8$ alkoxy, cyano, nitro, hydroxyl, amino and tetrazole, or Formula III:

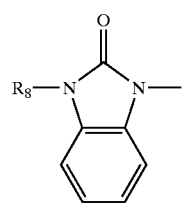

III (wherein $R_8$ represents hydrogen, $C_1$–$C_6$ linear alkyl, $C_3$–$C_8$ branched alkyl, or phenyl or benzyl, this phenyl or benzyl being substituted with 0 to 2 substituents selected from the group consisting of halogen, halogen, $C_1$–$C_8$ alkyl, $C_1$–$C_8$ alkoxy, cyano, nitro, hydroxyl, amino and tetrazole), (ii) Formula IV:

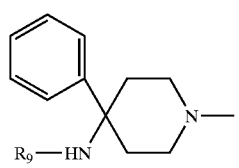

IV (wherein $R_9$ represents $C_1$–$C_6$ linear alkyl, $C_3$–$C_8$ branched alkyl, $C_1$–$C_6$ linear acyl, $C_3$–$C_8$ branched acyl, $C_5$–$C_7$ cycloalkylcarbonyl, $C_1$–$C_6$ linear alkylsulfonyl, $C_3$–$C_8$ branched alkylsulfonyl, or benzoyl, phenylsulfonyl or benzyl, this benzoyl, phenylsulfonyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole)

(iii) Formula V:

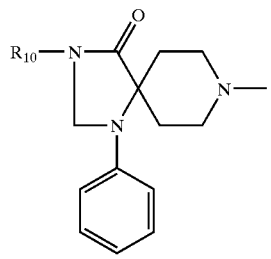

V (wherein $R_{10}$ represents hydrogen, $C_1$–$C_6$ linear alkyl, $C_3$–$C_8$ branched alkyl, $C_6$–$C_{10}$ alkylcycloalkyl, or phenyl or benzyl, this phenyl or benzyl being substituted with 0 to 2 substituents selected from the group consisting of halogen, $C_1$–$C_8$ alkyl, $C_1$–$C_8$ alkoxy, cyano, nitro, hydroxyl, amino and tetrazole);

When A is —CH— or carbon having a double bond, $R_3$, A and $R_4$ may cooperatively form adamantyl, or Formula VI:

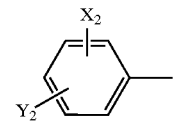

VI (wherein definitions of $X_2$ and $Y_2$ are the same as those of $X_1$ and $Y_1$, respectively)

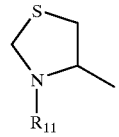

VII or Formula VII:

(wherein definition of $R_{11}$ is the same as that at $R_9$);

$R_5$ represents hydrogen, $C_1$–$C_6$ linear alkyl, $C_3$–$C_8$ branched alkyl, allyl, homoallyl, $C_6$–$C_{10}$ alkylcycloalkyl, or phenyl, benzyl, phenethyl, styryl or naphthylmethyl, this phenyl, benzyl, phenethyl, styryl or naphthylmethyl being substituted with 0 to 2 substituents selected from the group consisting of halogen, $C_1$–$C_8$ alkyl, $C_1$–$C_8$ alkoxy, cyano, nitro, hydroxyl, amino and tetrazole) or a pharmaceutically acceptable salt thereof.

7. The method according to claim 6, wherein said VLA-4 adhesion molecule is formed in connection with an allergic disease.

8. The method of claim 6, wherein the spiro derivative or pharmaceutically acceptable salt thereof is a compound, wherein F represents —C(O)—; A represents —CH—, carbon having a double bond or nitrogen atom, B represents —CH$_2$— or —NH—; C' and D represent hydrogen or C' and D cooperatively represent O; X and Y independently represent hydrogen, halogen, methyl, methoxy, cyano, nitro, hydroxyl, amino or tetrazole; R$_1$ and R$_2$ independently represent hydrogen or C$_1$–C$_6$ linear alkyl; R$_3$ and R$_4$ independently represent hydrogen, C$_1$–C$_6$ linear alkyl or C$_3$–C$_8$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole;

when A is a nitrogen atom, R$_3$, A and R$_4$ may cooperatively represent (i) said Formula II (wherein p represents an integer of 0 to 4; E represents carbon atom or nitrogen atom; R$_6$ and R$_7$ independently represent hydrogen, C$_1$–C$_6$ linear alkyl, C$_3$–C$_8$ branched alkyl, C$_1$–C$_6$ linear acyl, C$_3$–C$_8$ branched acyl, pyrrolidinecarbonyl, piperidinecarbonyl, or phenyl, phenylsulfonyl, benzoyl, benzyl, indole or N-phenylamide, this phenyl, phenylsulfonyl, benzoyl, benzyl, indole or N-phenylamide being substituted with 0 to 2 substituents selected from the group consisting of halogen, methyl, methoxy, cyano, nitro, hydroxyl, amino and tetrazole, or said Formula III (wherein R$_8$ represents hydrogen, C$_1$C$_6$ linear alkyl, C$_3$–C$_8$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole), (ii) said Formula IV (wherein R$_9$ represents C$_1$–C$_6$ linear alkyl, C$_3$–C$_8$ branched alkyl, C$_1$–C$_6$ linear acyl, C$_3$–C$_8$ branched acyl, C$_5$–C$_7$ cycloalkylcarbonyl, C$_1$–C$_6$ linear alkylsulfonyl, C$_3$–C$_8$ branched alkylsulfonyl, or benzoyl, phenylsulfonyl or benzyl, this benzoyl, phenylsulfonyl or benzyl being substituted with 0 to 2 substituents selected from the group consisting of halogen, methyl, methoxy, cyano, nitro, hydroxyl, amino and tetrazole), (iii) said Formula V:

(wherein R$_{10}$ represents hydrogen, C$_1$–C$_6$ linear alkyl, C$_3$–C$_8$ branched alkyl, C$_6$–C$_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole);

when A is —CH— or carbon having a double bond, R$_3$, A and R$_4$ may cooperatively represent adamantyl or said Formula VI (wherein X$_2$ and Y$_2$ represent the same definitions as described above); R$_5$ represents hydrogen, C$_1$–C$_6$ linear alkyl, C$_3$–C$_8$ branched alkyl, allyl, homoallyl, C$_6$–C$_{10}$ alkylcycloalkyl, or phenyl, benzyl, phenethyl, styryl or naphthylmethyl, this phenyl, benzyl, phenethyl, styryl or naphthylmethyl being substituted with 0 to 2 substituents selected from the group consisting of halogen, methyl, methoxy, cyano, nitro, hydroxyl, amino and tetrazole.

9. The method of claim 6, wherein the spiro derivative or pharmaceutically acceptable salt thereof is a compound, wherein A represents a nitrogen atom, R$_3$, A and R$_4$ cooperatively represent (i) said Formula II (wherein R$_6$ and R$_7$ independently represent hydrogen, C$_1$–C$_3$ linear alkyl, C$_3$–C$_6$ branched alkyl, C$_1$–C$_3$ linear acyl, C$_3$–C$_6$ branched acyl, pyrrolidinecarbonyl, piperidinecarbonyl, or phenyl, benzoyl, benzyl, indole or N-phenylamide, this phenyl, benzoyl, benzyl, indole or N-phenylamide being substituted with $_0$ to $_2$ substituents selected from the group consisting of halogen, methyl, methoxy, cyano, nitro, hydroxyl, amino and tetrazole), or said Formula III (wherein R$_8$ represents hydrogen, C$_1$–C$_3$ linear alkyl, C$_3$C$_6$ branched alkyl, or phenyl or benzyl, this phenyl or benzyl being substituted with 0 to 2 substituents selected from the group consisting of halogen, methyl, methoxy, cyano, nitro, hydroxyl, amino and tetrazole), (ii) said Formula IV (wherein R$_9$ represents C$_1$–C$_3$ linear alkyl, C$_3$–C$_6$ branched alkyl, C$_1$–C$_3$ linear acyl, C$_3$–C$_6$ branched acyl, C$_5$–C$_7$ cycloalkylcarbonyl, C$_1$–C$_3$ linear alkylsulfonyl, C$_3$–C$_8$ branched alkylsulfonyl, or benzoyl or benzyl, this benzoyl or benzyl being substituted with 0 to 2 substituents selected from the group consisting of halogen, methyl, methoxy, cyano, nitro, hydroxyl, amino and tetrazole), or (iii) said Formula V (wherein R$_{10}$ represents hydrogen, C$_1$–C$_3$ linear alkyl, C$_3$–C$_6$ branched alkyl, C$_6$C$_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole), the definitions of the symbols other than mentioned above are the same as those described in claim 1 or 2.

10. The method of claim 6, wherein the spiro derivative or pharmaceutically acceptable salt thereof is a compound, wherein A represents a nitrogen atom, R$_3$, A and R$_4$ cooperatively represent (i) said Formula II (wherein R$_6$ and R$_7$ independently represent hydrogen, C$_1$–C$_3$ linear acyl, C$_3$–C$_6$ branched acyl, pyrrolidinecarbonyl, piperidinecarbonyl, or phenyl, benzoyl, benzyl, indole or N-phenylamide, this phenyl, benzoyl, benzyl, indole or N-phenylamide being substituted with 0 to 2 substituents selected from the group consisting of halogen, methyl, methoxy, cyano, nitro, hydroxyl, amino and tetrazole), or said Formula III (wherein R$_8$ represents hydrogen, C$_1$–C$_3$ linear alkyl, C$_3$–C$_6$ branched alkyl, or benzyl substituted with 0 to 2 substituents selected from the group consisting of halogen, methyl, methoxy, cyano, nitro, hydroxyl, amino and tetrazole), (ii) said Formula IV (wherein R$_9$ represents C$_1$–C$_3$ linear acyl, C$_3$–C$_6$ branched acyl, C$_5$–C$_7$ cycloalkylcarbonyl, or benzoyl or benzyl, this benzoyl or benzyl being substituted with 0 to 2 substituents selected from the group consisting of halogen, methyl, methoxy, cyano, nitro, hydroxyl, amino and tetrazole), or (iii) said Formula V (wherein R$_{10}$ represents hydrogen, C$_1$–C$_3$ linear alkyl, C$_3$–C$_6$ branched alkyl, C$_6$-C$_{10}$ alkylcycloalkyl, or phenyl or benzyl, this phenyl or benzyl being substituted with 0 to 2 substituents selected from the group consisting of halogen, methyl, methoxy, cyano, nitro, hydroxyl, amino and tetrazole), the definitions of the symbols other than mentioned above are the same as those described in claim 1 or 2.

11. A pharmaceutical comprising said spiro derivative or a pharmaceutically acceptable salt thereof according to claim 3 as an effective ingredient and a carrier.

12. A pharmaceutical comprising said spiro derivative or a pharmaceutically acceptable salt thereof according to claim 4 as an effective ingredient and a carrier.

* * * * *